United States Patent
Coats et al.

(10) Patent No.: US 6,583,179 B2
(45) Date of Patent: Jun. 24, 2003

(54) SUBSTITUTED AMINOALKYLAMIDE DERIVATIVES AS ANTAGONISTS OF FOLLICLE STIMULATING HORMONE

(75) Inventors: Steven J. Coats, Quakertown, PA (US); Louis J. Fitzpatrick, Souderton, PA (US); Dennis J. Hlasta, Doylestown, PA (US); Carolina L. Lanter, Flemington, PA (US); Mark J. Macielag, Branchburg, NJ (US); Ke Pan, Phoenixville, PA (US); Ralph A. Rivero, Northwales, PA (US); Stephen S. Palmer, Plympton, MA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/745,283

(22) Filed: Dec. 21, 2000

(65) Prior Publication Data

US 2002/0058654 A1 May 16, 2002

Related U.S. Application Data

(60) Provisional application No. 60/173,139, filed on Dec. 27, 1999.

(51) Int. Cl.$^7$ .......................... A61K 31/18; A61P 5/34; C07D 401/00; C07C 311/00; C07C 233/00
(52) U.S. Cl. .......... 514/603; 514/217.03; 514/217.04; 514/252.12; 514/252.13; 514/316; 514/318; 514/327; 514/330; 514/311; 514/312; 514/314; 514/444; 514/445; 514/447; 514/459; 514/460; 540/597; 544/359; 544/361; 544/366; 546/152; 546/155; 546/156; 546/186
(58) Field of Search .............. 514/252.12, 253.01, 514/316, 318, 327, 330, 311, 312, 314, 444, 445, 447, 459, 460, 217.03, 217.04, 603; 544/359, 361, 366; 546/152, 155, 156, 186; 549/59, 62, 475, 483; 564/123, 86, 154–156; 540/597

(56) References Cited

U.S. PATENT DOCUMENTS

| 4,055,636 | A | * | 10/1977 | Okamoto et al. ............. 514/20 |
| 5,216,150 | A | * | 6/1993 | Hidaka et al. ............... 540/597 |
| 6,194,409 | B1 | * | 2/2001 | van Boeckel et al. ...... 514/243 |
| 6,200,963 | B1 | * | 3/2001 | Wrobel et al. ............. 514/150 |
| 6,355,633 | B1 | * | 3/2002 | Wrobel et al. ......... 514/212.01 |
| 6,376,538 | B1 | * | 4/2002 | Adams et al. ............... 514/466 |

FOREIGN PATENT DOCUMENTS

| WO | WO 93/05014 A | 3/1993 |
| WO | WO 97/12038 A | 4/1997 |
| WO | WO 00/58276 A1 | 10/2000 |
| WO | WO 00/58277 A1 | 10/2000 |

OTHER PUBLICATIONS

Rogers, John F. Synthesis of stilbene (bis) sulfonic acid, (bis) benzamides as FSH antagonists.Chemical Sciences, Wyeth–Ayerst Research, Radnor, PA, USA. Abstr. Pap.–Am. Chem. Soc. (2000), 220th MEDI–314. Coden: ACSRAI ISSN: 0065–7727. Journal; Meeting Abstract written in English. AN 2000:796313 CAPLUS.

M. Cardarelli et al.: Bioorg. Med. Chem. Lett., vol. 9, No. 14, 1999, pp. 2049–2052, XP004171635 table 1, compounds 26–34.

Y. Yhang et al.: Bioorg. Med. Chem. Lett., vol. 9, No. 19, 1999, pp. 2823–2826, XP004179171 tables 1–3.

* cited by examiner

*Primary Examiner*—Richard L. Raymond
*Assistant Examiner*—Tamthom N. Truong

(57) ABSTRACT

The present invention is directed to a series of novel substituted aminoalkylamide derivatives, pharmaceutical compositions containing them and their use in the treatment of reproductive disorders and affective conditions. Further, the compounds of the invention are antagonists of follicle stimulating hormone, a hormone associated with the human reproductive system.

38 Claims, No Drawings

SUBSTITUTED AMINOALKYLAMIDE DERIVATIVES AS ANTAGONISTS OF FOLLICLE STIMULATING HORMONE

CROSS REFERENCE TO RELATED APPLICATIONS

This application claims priority from U.S. provisional application Ser. No. 60/173,139, filed Dec. 27, 1999, the contents of which are hereby incorporated by reference.

FIELD OF THE INVENTION

This invention relates to novel substituted aminoalkylamide derivatives, pharmaceutical compositions containing them and their use in the treatment of reproductive disorders and affective conditions. The compounds of the invention are antagonists of follicle stimulating hormone, a hormone associated with the human reproductive system.

BACKGROUND OF THE INVENTION

Follicle stimulating hormone (FSH) belongs to a family of glycoprotein hormones, which includes lutenizing hormone (LH), thyrotropin (TSH) and chorionic gonadotropin (CG). Each of these hormones is composed of two different non-covalently bound subunits termed $\alpha$ and $\beta$. Within a species the amino acid sequence of the $\alpha$ subunits for these different hormones is identical, while the hormone specific $\beta$ subunits exhibit different amino acid sequences (Combarnous, Endocrine Review, 13:670–691 (1992).

In females, follicle stimulating hormone (FSH) stimulates follicular granulosa cell proliferation in the ovary and impacts synthesis of estrogen, a hormone which is integral to follicular maturation and ovulation. An antagonist of FSH therefore acts to limit proliferation of follicular granulosa cells in the ovary, acting as a contraceptive. The FSH antagonist may also delay the maturation of follicles within the ovary, thereby postponing the maturation of a limited number of follicles in women. Such treatments have the potential for increasing the possibility of natural fertilization and pregnancy later in life.

Because of the controlling function of FSH on estrogen synthesis, an FSH antagonist may also be effective in the treatment of estrogen related disorders such as uterine fibroids, endometriosis, polycystic ovarian disease, dysfunctional uterine bleeding, breast cancer and ovarian cancer.

An added advantage for an FSH antagonist would be its specific action on ovarian tissue without impact on peripheral tissues containing estrogen receptors. This would be expected to reduce the side effects associated with estrogen receptor antagonists.

Because the proliferation of follicular granulosa cells also impacts the health and development of the oocyte, FSH antagonists may be useful in preventing depletion of oocytes, a common side effect of chemotherapy or similar treatments designed to treat rapidly dividing cells.

In males, follicle stimulating hormone (FSH) is involved in the maturation of sperm cells. More specifically, FSH action in males is directed at the Sertoli cells, which are a recognized target of the hormone and which support the process of sperm maturation (spermatogenesis). FSH antagonists will therefore inhibit sperm maturation without affecting the production of androgens produced from Leydig cells under the control of luteinizing hormone (LH). In addition, FSH receptors have been reported in the epididymis in the male reproductive tract. Thus an FSH antagonist would be expected to affect the viability and motility of sperm by controlling functions of the epididymis.

FSH antagonists also have the potential to modify the rate of germ cell division in males. Because chemotherapy is known to deplete rapidly dividing cells such as spermatocytes, an FSH antagonist may be useful in a planned chemotherapy regimen to prevent spermatocyte depletion.

An FSH antagonist used as a female contraceptive could be used in contraceptive formulations alone or in combination with known contraceptive agents such as progesterone receptor modulators, estrogen receptor modulators, or androgen receptor modulators. An FSH antagonist used as a male contraceptive could be used alone or in combination with androgen receptor modulators, progesterone receptor modulators, or with estrogen receptor modulators. In addition, agents that affect the viability or motility or fertilizability of sperm by acting within the female genital tract may also be used in combination with FSH antagonists concomitantly, or as scheduled in a kit that prevents fertilization during the administration of an FSH antagonist. An example of such an agent is nonoxynol-9.

In recent years, peptide (based) FSH agonists and antagonists have been discovered and developed. Bono, G., et. al., in WO 97/12038 disclose novel amino acid residue peptide useful in stimulating FSH enhancement.

Amino acid based sulfonamide derivatives have also been developed for the treatment of a variety of conditions and disorders. Dumont, R. in WO 93/05014 discloses sulfonamide derivatives useful as inhibitors of $Ca^{+2}$ dependent enzymes.

The compounds of the present invention are non-peptide antagonists of FSH useful in the treatment of estrogen related disorders such as uterine fibroids, endometriosis, polycystic ovarian disease, dysfunctional uterine bleeding, breast cancer and ovarian cancer; prevention of depletion of oocytes (a common side effect of chemotherapy or similar treatment); female and male contraception; and prevention of spermatocyte depletion.

Additionally, the generation of chemical libraries on and off solid resins has proven to be a valuable resource for the pharmaceutical industry in their endeavors to discover new drugs using high throughput screening (HTPS) techniques. In creating the libraries, the compounds are ideally synthesized in situ in solution phase or on a solid support. However, relatively simple synthetic methods to produce a diverse collection of such derivatives in situ are often not available.

Pharmaceutical drug discovery relies heavily on studies of structure-activity relationships wherein the structure of "lead compounds" is typically altered to determine the effect of such alteration on activity. Alteration of the structure of the lead compounds permits evaluation of the effect of the structural alteration on activity.

Thus, libraries of compounds derived from a lead compound can be created by including derivatives of the lead compound and repeating the screening procedures. In this manner, compounds with the best biological profile, i.e., those that are most active and which have the most ideal pharmacologic and pharmacokinetic properties, can be identified from the initial lead compound.

SUMMARY OF THE INVENTION

The present invention is directed to compounds of the formula (I)

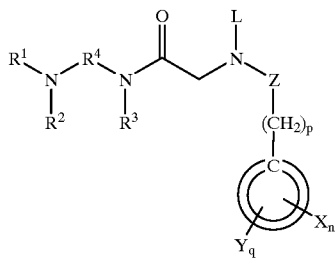

(I)

wherein

R¹ and R² are independently selected from the group consisting of hydrogen, $C_1$–$C_6$alkyl, $C_1$–$C_6$alkylcarbonyl, $C_1$–$C_6$perhaloalkyl, phenyl, phenyl$C_1$–$C_6$alkyl-, phenylcarbonyl-, pyridyl, pyridyl$C_1$–$C_6$alkyl-, pyridylcabonyl-, thienyl, thienyl$C_1$–$C_6$alkyl- and thienylcarbonyl, wherein the phenyl, pyridyl or thienyl is optionally substituted with one to three substituents independently selected from halogen, $C_1$–$C_6$alkyl, $C_1$–$C_6$alkoxy, trifluoromethyl, trifluoromethoxy or $NO_2$;

R³ is selected from the group consisting of hydrogen, $C_1$–$C_6$alkyl, $C_2$–$C_4$alkenyl and $C_2$–$C_4$alkynyl, where the $C_1$–$C_6$alkyl is optionally substituted with a phenyl, pyridyl, thienyl or furyl, wherein the phenyl, pyridyl, thienyl or furyl is optionally substituted with one to three substituents independently selected from halogen, $C_1$–$C_6$alkyl, $C_1$–$C_6$alkoxy, trifluoromethyl, trifluoromethoxy or $NO_2$;

R⁴ is selected from the group consisting of —$C_2$–$C_6$alkyl-, -cyclopentyl-, -cylcohexyl-, -cyclohexyl-$CH_2$—, —$CH_2$-cyclohexyl-$CH_2$—, —$CH_2$-phenyl-$CH_2$—, —C(O)—$CH_2$-phenyl-$CH_2$—, —C(O)—$C_1$–$C_6$alkyl- and -cyclohexyl-$CH_2$-cyclohexyl-;

where the R⁴ substituent is inserted into the compound of formula (I) from left to right, as defined;

alternately, R², R³, and R⁴ can be taken together with the two N atoms of the diamine portion of the molecule to form

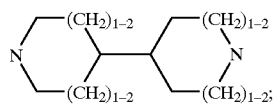

alternately, R³ can be taken together with R² as —$C_2$–$C_3$alkyl-, provided that R⁴ is —$C_2$–$C_6$alkyl-;

L is selected from the group consisting of —$C_3$–$C_6$cycloalkyl (wherein the cycloalkyl is substituted with R⁵ and R⁶), a bicyclic compound of the form

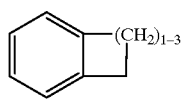

(wherein the point of the attachment of the bicyclic compound is any carbon atom of the alkyl portion and wherein the aromatic portion of the bicyclic compound is optionally substituted with one to three substituents independently selected from halogen, $C_1$–$C_6$alkyl, $C_1$–$C_6$alkoxy, trifluoromethyl, trifluoromethoxy, $NO_2$, acetamido, —$NH_2$, —NH($C_1$–$C_6$alkyl) or —N($C_1$–$C_6$alkyl)$_2$), and —$(CH_2)_m$-$CR^8R^5R^6$;

m is 0 to 3;

R⁵ is selected from the group consisting of phenyl, naphthyl, (wherein the phenyl and naphthyl may be optionally substituted with one to three substituents independently selected from halogen, $C_1$–$C_6$alkyl, $C_1$–$C_6$alkoxy, trifluoromethyl, trifluoromethoxy, $NO_2$, acetamido, —$NH_2$, —NH($C_1$–$C_6$alkyl), —N($C_1$–$C_6$alkyl)$_2$, $C_1$–$C_6$alkylcarbonylamino or $C_1$–$C_6$alkylsulfonylamino), bicyclo[4.2.0]octa-1,3,5-trienyl, 2,3-dihydro-1H-indolyl, N-methylpyrrolidinyl, 3,4-methylenedioxyphenyl, $C_3$–$C_6$cyloalkenyl, (wherein the cycloalkenyl group contains one or two double bonds), a six membered heteroaryl (wherein the six membered heteroaryl contains one to three N atoms), and a five membered heteroaryl (wherein the five membered heteroaryl contains one sulfur, oxygen or nitrogen, optionally contains one to three additional nitrogen atoms); wherein the point of attachment for the five or six membered heteroaryl is a carbon atom; and wherein the five or six membered heteroaryl is optionally substituted with one to three substituents independently selected from halogen, $C_1$–$C_6$alkyl, $C_1$–$C_6$alkoxy, trifluoromethyl, trifluoromethoxy or $NO_2$;

R⁶ is selected from the group consisting of hydrogen, $C_1$–$C_6$alkyl, $C_3$–$C_6$cycloalkyl, $C_1$–$C_6$alkoxy, hydroxy and phenyl, (wherein the phenyl may be optionally substituted with one to three substituents independently selected from halogen, $C_1$–$C_6$alkyl, $C_1$–$C_6$alkoxy, trifluoromethyl or trifluoromethoxyl); provided that R⁶ may be phenyl only when R⁵ is phenyl;

R⁸ is selected from the group consisting of hydrogen and $C_1$–$C_6$alkyl;

Z is selected from the group consisting of —$SO_2$—, —C(=O)—, and —C(=O)NH—;

p is 0 to 1;

is selected from the group consisting of phenyl, naphthyl, quinolinyl, thienyl, and furyl;

X is selected from the group consisting of halogen, $C_1$–$C_6$alkyl, $C_1$–$C_6$alkoxy, trifluoromethyl, trifluoromethoxy, $NO_2$, acetamido, —$NH_2$, —NH($C_1$–$C_6$alkyl) and —N($C_1$–$C_6$alkyl)$_2$;

n is 0 to 3;

Y is selected from the group consisting of phenyl, —O—phenyl, —NH—phenyl, naphthyl, (wherein the phenyl or naphthyl is optionally substituted with one to three substituents selected from halogen, $C_1$–$C_6$alkyl, $C_1$–$C_6$alkoxy, trifluoromethyl, trifluoromethoxy, $NO_2$, cyano, methylthio, acetamido, formyl, -amino, -aminocarbonyl, —NH—$C_1$–$C_6$alkyl, —N($C_1$–$C_6$alkyl)$_2$, —COOH, —COO($C_1$–$C_6$alkyl), —COO($C_1$–$C_6$alkylphenyl), $C_1$–$C_6$alkylcarbonylamino, $C_1$–$C_6$alkylaminocarbonyl, di($C_1$–$C_6$alkyl)aminocarbonyl, aminosulfonyl, $C_1$–$C_6$alkylaminosulfonyl or di($C_1$–$C_6$alkyl)aminosulfonyl), biphenyl, 3,4-methylenedioxyphenyl, dianthrenyl, dibenzothienyl, phenoxathiinyl, a six membered heteroaryl (wherein the six membered heteroaryl contains one to three nitrogen atoms), and a five membered heteroaryl (wherein the five membered heteroaryl contains one sulfur, oxygen or nitrogen atom, optionally contains one to three additional nitrogen atoms); wherein the point of attachment for the five or six membered heteroaryl is a carbon atom; and wherein the five or six membered heteroaryl is optionally substituted with one to three substituents selected from halogen, $C_1$–$C_6$alkyl, $C_1$–$C_6$alkoxy, trifluoromethyl, trifluoromethoxy, formyl, $NO_2$, cyano, methylthio, acetamido, -amino, -aminocarbonyl, —NH $C_1$–$C_6$alkyl, —N($C_1$–$C_6$alkyl)$_2$, —COOH, —COO ($C_1$–$C_6$alkyl), or —COO($C_1$–$C_6$alkylphenyl));

q is 0 to 1;

provided that when q is 1, n is 0;

and stereoisomers and pharmaceutically acceptable salts or esters thereof.

DETAILED DESCRIPTION OF THE INVENTION

The compounds of formula (I) that comprise this invention may be prepared using a process wherein the compound is synthesized on a solid support resin, followed by cleavage of the compound from the resin support, as a final isolation step. The various substituents described in formula (I) may be present initially on the reagents employed to prepare the compounds of formula (I). In some instances they may be conveniently added following cleavage. In those cases where the substituents are present on the reagents, care must be taken in the selection of the resin to insure that the substituents are compatible with the selected resin.

One method for producing the compounds of formula (I) involves synthesis, on resin, of three intermediates, followed by cleavage of the resin to yield the desired product, as outlined in Scheme 1.

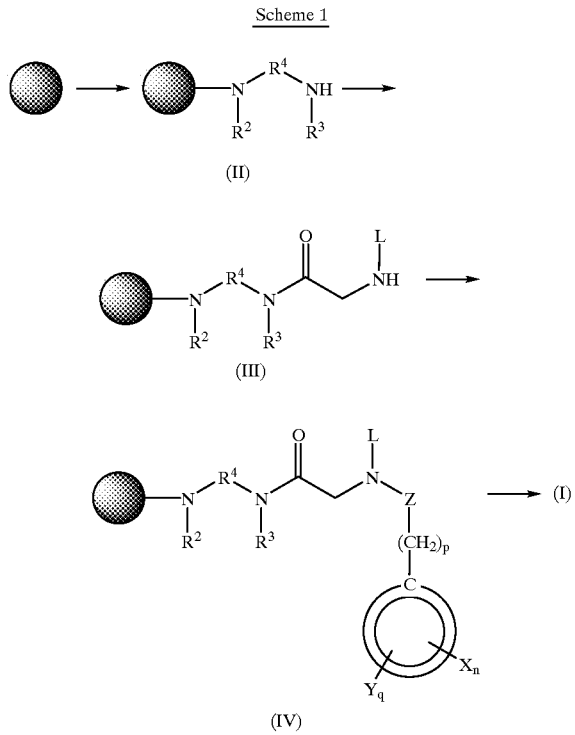

Scheme 1

The solid support resin, herein represented by the symbol ● is typically polystyrene, and is terminated with a reactive functional group. There are a number of commercially available resins, with a variety of terminating groups. Suitable examples of support resins for preparation of compounds of formula (I) include: Wang resin (Wang, S. S., J. Am. Chem. Soc., 95, 1328 (1973); Kiselov, A. S. and Amstrong, R. W., Tetrahedron Letter, 318, 6163 (1997)), [wherein the terminating group is —(p-phenyl)—$CH_2$—O—(p-phenyl)—$CH_2$—OH]; RAPP Tentagel SAM resin (Rotte, B., et.al., Collect. Czech. Chem. Commun., 61, 5304 (1996)), [wherein the terminating group is —(p-phenyl)—$CH_2$—O—(p-phenyl)—$CH_2$—$NH_2$]; vinylsulfonyl resin (Kroll, F. E., et. al., Tetrahedron Lett., 38, 8573, 1997), [wherein the terminating group is —(p-phenyl)—$CH_2$—$SO_2$—CH=$CH_2$]; rink amide resin (Rink, H., Tetrahedron Lett., 28, 3787, 1987; Brown, E. G. and Nuss, J. M., Tetrahedron Lett., 38, 8457, 1997), [wherein the terminating group is —$CH_2$—O—(p-phenyl)—$CH_2$(NH—Fmoc)-(2,4-dimethoxyphenyl)]; FMPB resin (4-(4-formyl-3-methoxyphenoxy)butyryl AM resin) (Bilodeau, M. T. & Cunningham, A. M., J. Org. Chem., 63, 2800, 1998; Kearny, P. T., et. al., J. Org. Chem., 63, 196, 1998) [wherein the terminating group is an aldehyde]; and the like. The appropriate selection of solid support resin and terminating group is based on the synthesis steps, reaction conditions and final compound substituents; and may be determined by one skilled in the art.

The selected resin and appropriate reactants are employed to prepare resin bound, substituted diamines of formula (II):

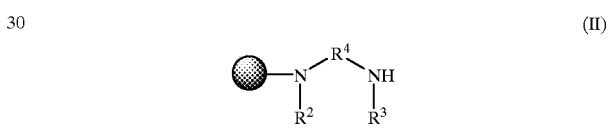

Broadly, there are three approaches described herein to obtain the resin bound substituted diamines of formula (II). In the first approach a commercial resin capable of direct coupling reactions to an appropriately substituted diamine is purchased and reacted to produce the compound of formula (II). In the second approach, a commercial resin is suitably activated to react with an appropriately substituted diamine. This approach is advantageously employed in those cases where the purchased resin is not amine terminated. In the third approach, a commercially available amine terminated resin is reacted with a substituted and protected amine alcohol to form the resin substituted diamine of formula (II). In this third approach, the terminal amine of the selected resin is incorporated into the end product compound.

Specifically, compounds of formula (II) wherein $R^2$ and $R^3$ are hydrogen; wherein $R^2$ and $R^3$ are taken together as —$C_2$–$C_3$alkyl and $R^4$ is other than C(O)—$CH_2$-phenyl-$CH_2$— or C(O)—$C_1$–$C_6$alkyl-; and wherein $R^2$, $R^3$ and $R^4$ are taken together with the two N atoms of the diamine portion of the molecule to form

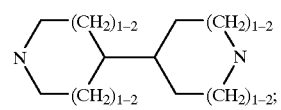

may be prepared as outlined in Scheme 2 below:

SCHEME 2

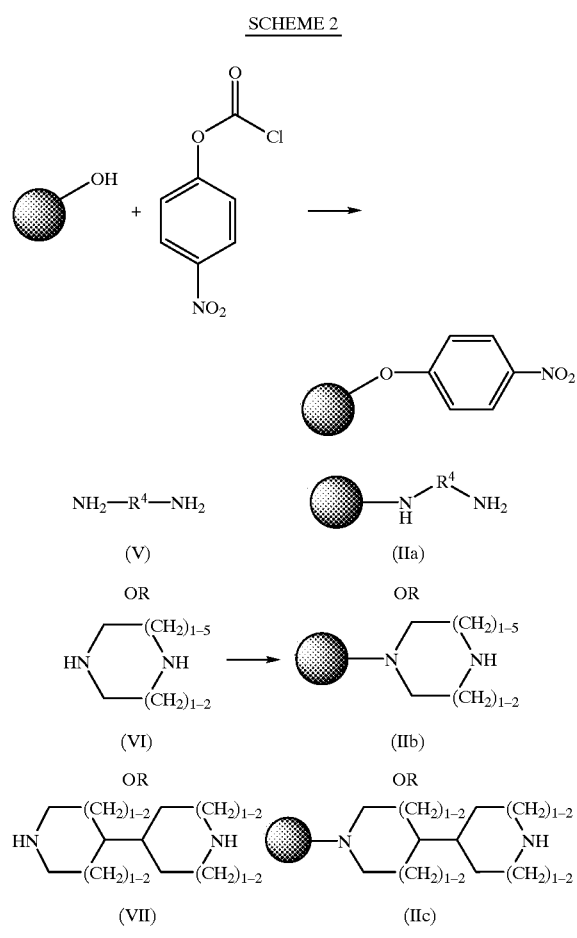

According to Scheme 2, a commercially available, OH terminated resin is coupled with 4-nitrophenyl chloroformate, in an organic solvent such as DCM, DCE, and the like, preferably DCM, in the presence of an amine base, such as pyridine, N-methylmorpholine (NMM), triethylamine (TEA), diisopropylethylamine (DIEA), and the like, preferably N-methylmorpholine (NMM), preferably at room temperature, to incorporate the —C(O)—O—(p-nitrophenyl)— group into the resin, to form the corresponding p-nitrophenol carbonate terminated resin.

The p-nitrophenol group on the p-nitrophenol carbonate terminated resin is next displaced with a suitably substituted linear diamine of formula (V), a suitably substituted cyclic diamine of formula (VI), or a suitably substituted bicyclic heterocyclyl diamine of formula (VII), in an organic solvent such as DMF, DMAC, DCM, DCE, and the like, preferably at room temperature, to form the corresponding resin bound substituted diamine of formula (IIa), (IIb) or (IIc), respectively.

Alternately, compounds of formula (II), wherein $R^2$ and $R^3$ are hydrogen may be prepared according to the process outlined in Scheme 3.

SCHEME 3

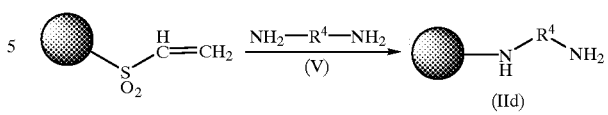

Accordingly, a commercially available, vinylsulfonyl terminated resin is coupled with a suitably substituted linear diamine of formula (V), in an organic solvent such as DMF, overnight, at room temperature, to produce the resin bound substituted diamine of formula (IId). In this approach, the amine group is coupled directly to the terminal methylene group of the vinylsulfonyl terminated resin.

Compounds of formula (II) wherein $R^3$ is hydrogen and $R^4$ is selected from C(O)—CH$_2$-phenyl-CH$_2$— or C(O)—C$_1$–C$_6$alkyl- may be prepared according to the process outlined in Scheme 4.

SCHEME 4

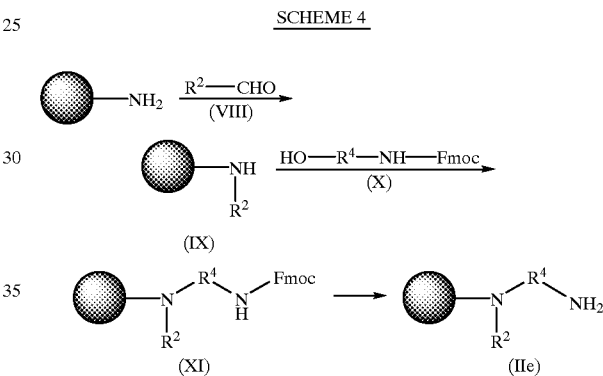

When $R^2$ is other than hydrogen, a commercially available amine terminated resin is reacted with a suitably substituted aldehyde of formula (VIII), in an organic solvent such as DCM, DCE, and the like, in the presence of a catalyst such as sodium cyanoborohydride, sodium triacetoxyborohydride and the like, preferably sodium triacetoxyborohydride, preferably at room temperature, to produce the corresponding substituted amine terminated resin of formula (IX).

The substituted amine terminated resin of formula (IX) is coupled with a suitably substituted Fmoc-protected amine alcohol, a compound of formula (X), in an organic solvent such as DMF, DMAC, DCM, and the like, preferably DMF, preferably at room temperature, to produce the corresponding resin bound Fmoc-protected, substituted diamine of formula (XI). The Fmoc protecting group on the resin bound substituted diamine of formula (XI) is then removed using 20% piperidine in DMF, preferably at room temperature, to produce the corresponding resin bound, substituted diamine of formula (IIe).

Compounds of formula (II) wherein $R^3$ is other than hydrogen may be prepared according to the process outlined in Scheme 5.

SCHEME 5

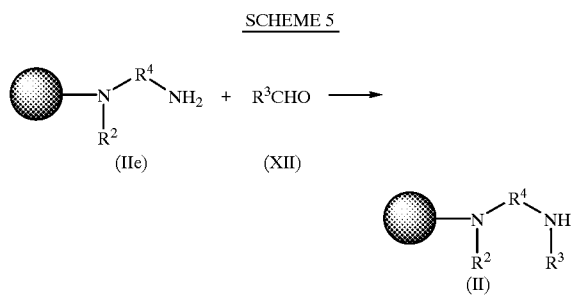

A resin bound substituted diamine of formula (IIe) is coupled with a suitably substituted aldehyde of formula (XII), in the presence of a reducing agent such as sodium cyanoborohydride, sodium triacetoxyborohydride, and the like, preferably triacetoxyborohydride, in an organic solvent such as DCM, DCE, and the like, preferably DCE, preferably at room temperature, to produce the corresponding resin bound substituted diamine of formula (II).

The resin bound, substituted diamines of formula (II) are next reacted with suitably substituted reagents to produce the corresponding resin bound, substituted secondary amine of formula (III):

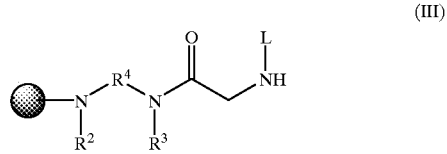

In a general approach to producing the resin bound substituted triamine of formula (III), bromoacetic acid is initially coupled to the diamine for formula (II), followed by coupling of a suitably substituted amine.

More specifically, in this approach, compounds of formula (III) may be prepared according to the process outlined in Scheme 6. This approach is also particularly advantageous in the preparation of compounds of formula (I) wherein L is —$C_3$–$C_6$cycloalkyl.

SCHEME 6

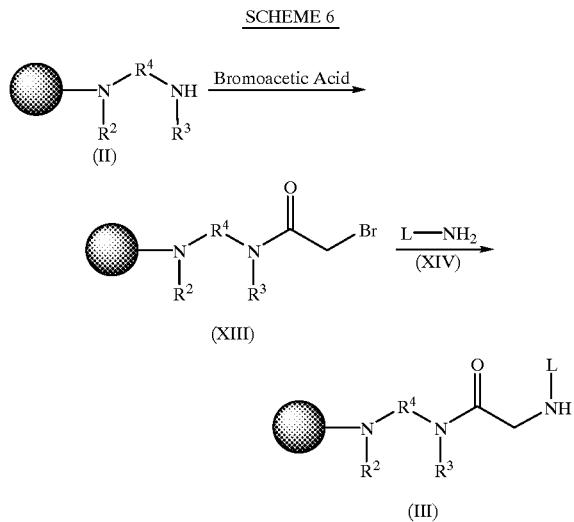

Accordingly, a resin bound, substituted diamine of formula (II) is coupled with bromoacetic acid, using a coupling agent such as diisopropyl carbodiimide, 1,1'-carbonyldiimidazole, N,N'-dicyclohexylcarbodiamide, and the like, preferably diisopropylcarbodiamide, in a solvent such as DMF, DMAC, and the like, preferably DMF, preferably at room temperature, to form the corresponding resin bound, bromoacetylated alkylcarbonyl diamine of formula (XIII).

The bromine on the resin bound, bromoacetylated alkylcarbonyl diamine of formula (XIII) is then displaced with a suitably substituted amine of formula (XIV), in a solvent such as DMSO, preferably at room temperature, to form the corresponding resin bound, substituted secondary amine of formula (III).

The resin bound, substituted secondary amine of formula (III) is subsequently reacted with suitably substituted reagents to produce the corresponding resin bound, compound of formula (IV):

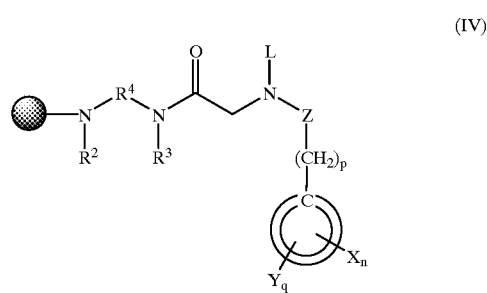

The resin bound compound of formula (IV) may be prepared via two processes. In the first process, the resin bound, substituted secondary amine of formula (III) is directly coupled with a suitably substituted sulfonyl chloride, suitably substituted carbonyl chloride or suitably substituted isocyanate reagent to prepared the end product compound. In the second process, the resin bound, substituted secondary amine of formula (III) is first coupled with a halogen substituted aryl or heteroaryl sulfonyl chloride, followed by displacement of the halogen with a suitably substituted aryl or heteroaryl substituted boronic acid, to yield the end product compound.

More particularly, in the first process, the resin bound compound of formula (IV) is prepared as outlined in Scheme 7.

Scheme 7

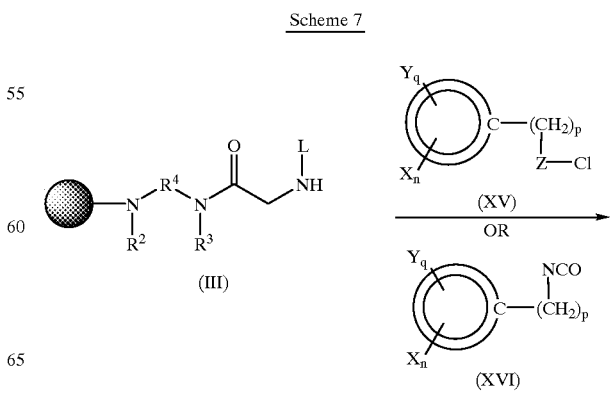

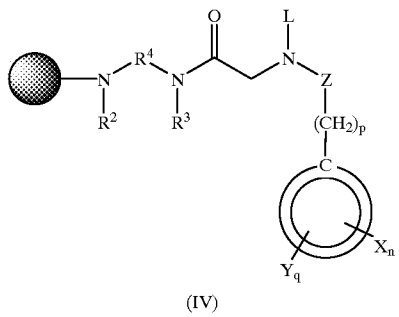

(IV)

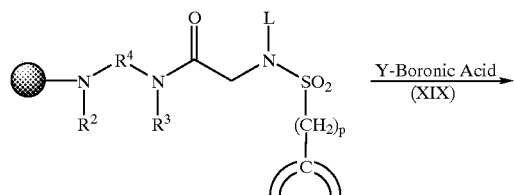

(XVIII)

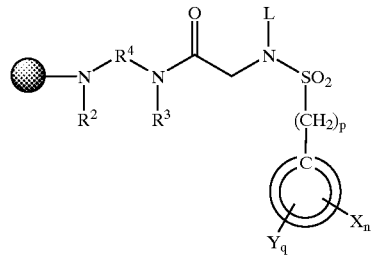

(IVa)

According to the first process, the resin bound, substituted secondary amine of formula (III) is coupled with a suitably substituted chloride of formula (XV), or a suitably substituted isocyanate of formula (XVI), in a solvent such as DCM, DCE, chloroform, and the like, preferably DCM, in the presence of an amine base such as pyridine, N-methylmorpholine (NMM), triethyl amine (TEA), diisopropylethylamine (DIEA), and the like, preferably pyridine, preferably at room temperature, to form the corresponding resin bound compound of formula (IV).

The second process is particularly advantageous for preparation of compounds of formula (I) wherein Z is sulfonyl, n is 0, q is 1 and the

substituent is phenyl, napthyl, thienyl or furyl. The second process is also particularly advantageous for preparation of compounds of formula (I) wherein $R^2$ and $R^3$ are taken together as $C_2$–$C_3$alkyl and Z is sulfonyl; and wherein $R^2$, $R^3$, and $R^4$ are taken together with the two N atoms of the diamine portion of the molecule to form

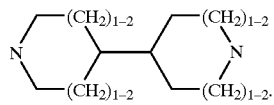

In the second process, the resin bound compound of formula (IV) is prepared via the process outlined in Scheme 8.

Scheme 8

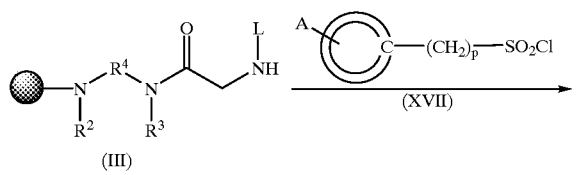

The resin bound, substituted secondary amine of formula (III) is coupled with a suitably substituted aryl or heteroaryl sulfonyl chloride of formula (XVII), wherein A represents a halogen selected from chlorine, bromine or iodine, preferably bromine, in a solvent such as DCM, DCE, chloroform, and the like, preferably DCM, in the presence of an amine base such as pyridine, N-methylmorpholine, triethylamine (TEA), diisopropylethylamine (DIEA), and the like, preferably pyridine, preferably at room temperature, to form the corresponding resin bound, substituted sulfonyl compound of formula (XVIII).

On the resin bound, substituted sulfonyl of formula (XVIII), the halogen represented by A is next displaced with a suitably substituted boronic acid of formula (XIX), using Suzuki conditions (in a solvent such as dimethoxyethane (DME), dioxane, and the like, in the presence of a base such as 2M sodium carbonate, tetramethylguanadine (TMG), and the like, under a $N_2$ atmosphere, at a temperature in the range of about 80–100° C., in the presence of a catalyst, such as palladium tetrakistriphenylphosphine), to form the corresponding resin bound, substituted sulfonamide formula (IVa).

The resin bound compound of formula (IV), may next be treated to yield the corresponding compound of formula (I) by cleaving the solid support resin, using a cleaving cocktail, such as 90:10 TFA:water, preferably at room temperature, to produce the corresponding compound of formula (I).

A resin bound compound of formula (IVa) may alternatively be further reacted with a suitably substituted compound of formula (XX) and/or formula (XXI), wherein J is bromine or iodine, to incorporate $R^1$ and $R^2$ substituents, wherein $R^1$=$R^2$ and are other than hydrogen. For this process, the preferred resin is the vinylsulfonyl terminated resin, $R^4$ is other than —C(O)—$CH_2$-phenyl- or —C(O)-$C_1$–$C_6$alkyl-, and the $R^1$ and $R^2$ substituents are incorporated according to the process outlined in Scheme 9.

Scheme 9

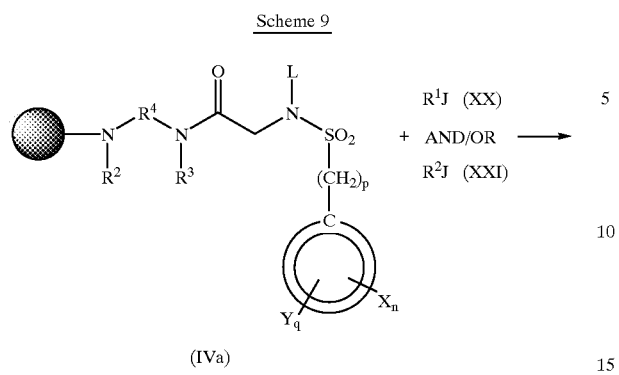

(IVa)

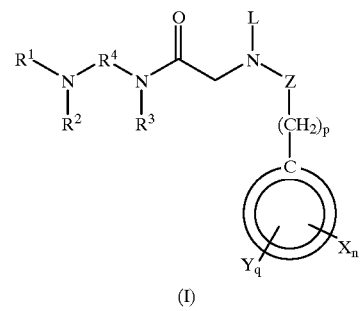

(I)

A compound of formula (Ia), wherein $R^1$ and $R^2$ are hydrogen, is treated with a suitably substituted aldehyde of formula (XXIII), preferably in the amount of at least one molar equivalent, in an organic solvent such as TMOF, and the like, in the presence of a reducing agent such as sodium triacetoxyborohydride, and the like, preferably at room temperature, and then with a suitably substituted aldehyde of formula (XXIV), preferably in the amount of at least one molar equivalent, in an organic solvent such as TMOF, and the like, in the presence of a reducing agent such as sodium triacetoxyborohydride, and the like, preferably at room temperature, to produce the corresponding compound of formula (I).

(XXII)

Accordingly, a resin bound compound of formula (IVa) is reacted with a suitably substituted compound of formula (XX) and/or formula (XXI), wherein J is bromine or iodine, preferably at room temperature, to produce the corresponding resin bound, quaternary amine of formula (XXII).

The resin bound quaternary amine of formula (XXVI) is then treated to yield the desired corresponding compound of formula (I) by cleaving the solid support resin, using a cleaving cocktail, such as 20% DIEA in DMF, preferably at room temperature, to produce the corresponding compound of formula (I).

In an alternative scheme for producing compounds of formula (I) wherein $R^1$ and/or $R^2$ are other than hydrogen, the $R^1$ and $R^2$ substituents may be introduced following cleavage of the resin bound compound of formula (IV). More particularly, such a process is as outlined in Scheme 10.

In an alternative method of Scheme 10, compounds of formula (I), wherein $R^1$ and $R^2$ are the same and other than hydrogen, are produced by treating the compound of formula (Ia) with at least two molar equivalents of a suitably substituted aldehyde of formula (XXIII) or (XXIV), to produce the corresponding product of formula (I).

In another alternative method of Scheme 10, compounds of formula (I), wherein one of $R^1$ or $R^2$ is hydrogen, the compound of formula (Ia) is treated with at least one molar equivalent of a suitably substituted aldehyde of formula (XXIII) or (XXIV), to yield the desired corresponding compound of formula (I).

Compounds of formula (I), wherein $R^1$ and/or $R^2$ is alkylcarbonyl may be prepared according to the process outlined in Scheme 11.

Scheme 10

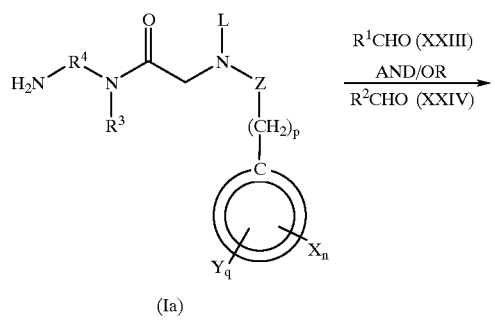

(Ia)

Scheme 11

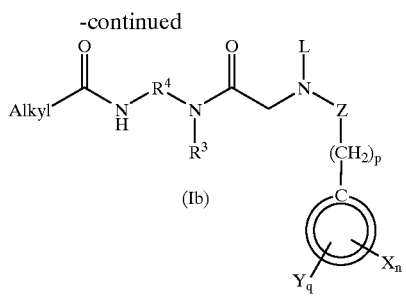

(Ib)

Accordingly, a suitably substituted compound of formula (Ia), wherein $R^1$ and $R^2$ are each hydrogen, is treated with a suitably substituted acid chloride of formula (XXV), preferably in the amount of at least one molar equivalent, in an organic solvent such as chloroform, DCM, and the like, in the presence of a organic base such as TEA, and the like, preferably at room temperature, to yield the corresponding compound of formula (Ib). Alternatively, a suitably substituted compound of formula (Ia), wherein $R^1$ and $R^2$ are each hydrogen, is treated with a suitably substituted carboxylic acid of formula (XXVI), preferably in the amount of at least one molar equivalent, in an organic solvent such as DMF, and the like, in the presence of a coupling agent such as DIC, and the like, preferably at room temperature, to yield the corresponding compound of formula (Ib).

As used herein, unless otherwise noted, "alkyl" whether used alone or as part of a substituent group, shall include straight and branched chains containing 1 to 6 carbon atoms. For example, alkyl radicals include methyl, ethyl, propyl, isopropyl, butyl, isobutyl, sec-butyl, t-butyl, pentyl, 2-methyl-3-butyl, hexyl and the like. Similarly, the term "cycloalkyl" shall include saturated alkyl ring structures containing 3 to 6 carbon atoms. Suitable examples include cyclopropyl, cyclobutyl, cyclopentyl and cylcohexyl.

As used herein, unless otherwise noted, "alkenyl" and "alkynyl" shall include straight and branched chain alkene and alkyne having 1 to 6 carbon atoms, for example allyl, vinyl, 2-propenyl, 2-propynyl, and the like.

As used herein, unless otherwise noted, "alkoxy" shall denote an oxygen ether radical of the above described straight or branched chain alkyl groups. For example, methoxy, ethoxy, propoxy, sec-butoxy, t-butoxy, 2-methyl-3-bytoxy and the like.

As used herein the terms "aromatic and aryl" shall denote phenyl and naphthyl.

Suitable "six membered heteroaryls containing one to three nitrogen atoms" include pyridyl, pyridizanyl, pyrimidinyl, pyrazinyl, 1,3,5-triazinyl, 1,2,4-triazinyl and 1,2,3-triazinyl.

Suitable "five membered heteroaryl containing one sulfur, oxygen or nitrogen atom, optionally containing one to three additional nitrogen atoms" include thienyl, furyl, pyrrolyl, thiazolyl, isothiazolyl, thiadiazolyl, oxazolyl, isoxazolyl, 1,2,3-oxadiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, imidazolyl, pyrazolyl, 1,2,3-triazolyl, 1,2,4-triazolyl, and the like.

As used herein, unless otherwise noted, "halogen" shall denote chlorine, bromine, fluorine and iodine.

As used herein, unless otherwise noted, "*" represents the presence of a stereogenic center.

Under standard nomenclature used throughout this disclosure, the terminal portion of the designated side chain is described first, followed by the adjacent functionality toward the point of attachment. Thus, for example, a "phenyl$C_1$–$C_6$alkylamido$C_1$–$C_6$alkyl" substituent refers to a group of the formula

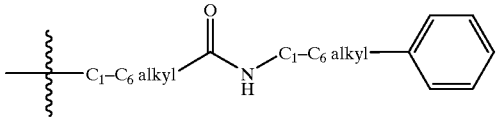

In a preferred embodiment of the present invention are compounds of the formula (I) wherein $R^1$ and $R^2$ are independently selected from the group consisting of hydrogen, methyl, ethyl, methylcarbonyl, trifluoromethyl, phenyl, benzyl, phenylcarbonyl, pyridyl, pyridylcarbonyl, thienyl, thienylmethyl and thienylcarbonyl (where the phenyl, pyridyl or thienyl is optionally substituted with one to two substituents independently selected from halogen, $C_1$–$C_3$alkyl, $C_1$–$C_3$alkoxy, trifluoromethyl, trifluoromethoxy or nitro); and $R^3$ is selected from the group consisting of hydrogen, methyl, —CH=CH— (optionally substituted with phenyl, pyridyl or thienyl; wherein the phenyl, pyridyl or thienyl is further optionally substituted with one to two substituents independently selected from the group consisting of halogen, $C_1$–$C_3$alkyl, $C_1$–$C_3$alkoxy, trifluoromethyl, trifluoromethoxy and nitro), —C≡C—, (optionally substituted with phenyl, pyridyl or thienyl; wherein the phenyl, pyridyl or thienyl is further optionally substituted with one to two substituents independently selected from the group consisting of halogen, $C_1$–$C_3$alkyl, $C_1$–$C_3$alkoxy, trifluoromethyl, trifluoromethoxy and nitro).

More preferably, $R^1$, $R^2$, and $R^3$ are the same; most preferably $R^1$, $R^2$ and $R^3$ are the same and are hydrogen.

In another preferred embodiment of the present invention are compounds of the formula (I) wherein $R^2$ and $R^3$ are taken together as $C_2$–$C_3$alkyl, more preferably 1,2-ethyl; and $R^4$ is $C_2$–$C_6$alkyl, more preferably 1,2-ethyl or 1,3-n-propyl.

In another preferred embodiment of the present invention are compounds of the formula (I) wherein $R^2$, $R^3$, and $R^4$ are taken together with the two N atoms of the diamine portion of the molecule to form

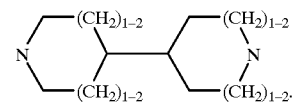

Preferred $R^4$ substituents include —$C_2$–$C_6$alkyl, -cyclohexyl, —$CH_2$-cyclohexyl—$CH_2$, -cyclohexyl—$CH_2$-cyclohexyl and —$CH_2$-phenyl—$CH_2$.

In another preferred embodiment of the invention are compounds of the formula (I) wherein $R^2$, $R^3$, and $R^4$ may be taken together with the two N atoms of the diamine portion of the molecule to form 4,4'-bipiperidinyl.

Preferred L substituents include -cyclopropyl-, cyclohexyl-, (wherein the cylcopropyl or cyclohexyl is substituted with $R^5$ and $R^6$),

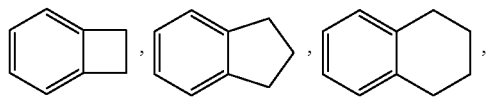

and $(CH_2)_m$—$CR^8R^5R^6$.

Preferred $R^5$ substituents include phenyl (wherein the phenyl is optionally substituted with one to two substituents independently selected from halogen, $C_1$–$C_3$alkyl, $C_1$–$C_3$alkoxy, trifluoromethyl, trifluoromethoxy, methylcarbonylamino, methylsulfonylamino, nitro, acetomido, amino, $C_1$–$C_3$alkylamino or di($C_1$–$C_3$alkyl)amino), N-methylpyrrolidinyl, 3,4-methylenedioxyphenyl, bicyclo[4.2.0]octa-1,3,5-trienyl, 2,3-dihydro-1H-indolyl, $C_3$–$C_6$cycloalkenyl (wherein the cycloalkenyl contains one or two double bonds), thienyl, furyl, pyrrolyl, oxazolyl, imidazolyl, pyrazolyl, triazolyl, pyridyl, pyrimidyl, pyrazinyl and triazinyl.

Preferred $R^6$ substituents include hydrogen, $C_1$–$C_3$alkyl, cyclopropyl, cyclobutyl, cyclohexyl, $C_1$–$C_3$alkoxy, hydroxy and phenyl (wherein the phenyl is optionally substituted with one to two substituents independently selected from halogen, $C_1$–$C_3$alkyl, $C_1$–$C_3$alkoxy, trifluoromethyl or trifluoromethoxy); provided that $R^6$ is phenyl only when $R^5$ is phenyl.

Preferred $R^8$ substituents include hydrogen and $C_1$–$C_3$alkyl.

Preferably Z is selected from the group consisting of $SO_2$, $C(=O)$ and $-C(=O)-NH-$.

Preferred

substituents include phenyl, naphthyl, quinolinyl and thienyl.

Preferably n is 0 to 2.

Preferred X substituents include halogen, $C_1$–$C_6$alkyl, $C_1$–$C_4$alkoxy, trifluoromethyl, trifluoromethoxy, nitro, acetamido, amino, $C_1$–$C_3$alkylamino and di($C_1$–$C_3$alkyl)amino.

Preferred Y substituents include phenyl, naphthyl, (wherein the phenyl or naphthyl is optionally substituted with one to three substituents independently selected from halogen, $C_1$–$C_3$alkyl, $C_1$–$C_3$alkoxy, trifluoromethyl, trifluoromethoxy, formyl, nitro, cyano, methylthio, acetamido, amino, aminocarbonyl, $C_1$–$C_3$alkylamino, di($C_1$–$C_3$alkyl)amino, carboxy, $-COO(C_1$–$C_3$alkyl), $-COO(C_1$–$C_3$alkylphenyl), $C_{1-4}$alkylaminosulfonyl, $C_1$–$C_4$alkylcarbonylamino), biphenyl, 3,4-methylenedioxyphenyl, dianthryl, dibenzothienyl, phenoxathiinyl, a five membered heteroaryl (wherein the five membered heteroaryl contains one nitrogen, oxygen or sulfur atom and optionally contains an additional nitrogen or oxygen atom) and a six membered heteroaryl (wherein the six membered heteroaryl contains one nitrogen atom and optionally contains an additional nitrogen or oxygen atom); wherein the five or six membered heteroaryl is optionally substituted with one to two substituents independently selected from halogen, $C_1$–$C_3$alkyl, $C_1$–$C_3$alkoxy, trifluoromethyl, trifluoromethoxy, formyl, nitro, cyano, methylthio, acetamido, amino, aminocarbonyl, $C_1$–$C_3$alkylamino or di($C_1$–$C_3$alkyl)amino; and wherein the point of attachment for the five or six membered heteroaryl is a carbon atom.

Particularly preferred compounds of the present invention are listed in Table 1, below.

TABLE 1

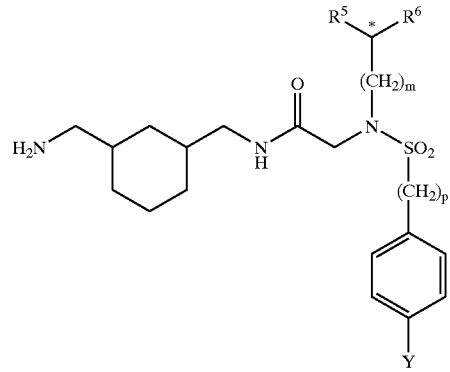

| Cmpd # | m | $R^5$ | $R^6$ | Stereo | p | Y |
| --- | --- | --- | --- | --- | --- | --- |
| 336 | 1 | 2-methoxyphenyl | H | — | 0 | 2-methylphenyl |
| 337 | 1 | 2-methoxyphenyl | H | — | 0 | 2-chlorophenyl |
| 338 | 1 | 2-methoxyphenyl | H | — | 0 | 2-methoxyphenyl |
| 339 | 1 | 2-methoxyphenyl | H | — | 0 | 2,4-dichlorophenyl |
| 340 | 0 | 2-methoxyphenyl | H | — | 0 | 2-methylphenyl |
| 341 | 0 | 2-methoxyphenyl | H | — | 0 | 2-chlorophenyl |
| 342 | 0 | 2-methoxyphenyl | H | — | 0 | 2-methoxyphenyl |
| 343 | 0 | 2-methoxyphenyl | H | — | 0 | 2,4-dichlorophenyl |
| 384 | 1 | phenyl | $CH_3$ | R | 0 | 2-methylphenyl |
| 385 | 1 | phenyl | $CH_3$ | R | 0 | 2-chlorophenyl |
| 386 | 1 | phenyl | $CH_3$ | R | 0 | 3-fluorophenyl |
| 387 | 1 | phenyl | $CH_3$ | S | 0 | 2-methylphenyl |
| 388 | 1 | phenyl | $CH_3$ | S | 0 | 2-chlorophenyl |
| 389 | 1 | phenyl | $CH_3$ | S | 0 | 3-fluorophenyl |

TABLE 1-continued

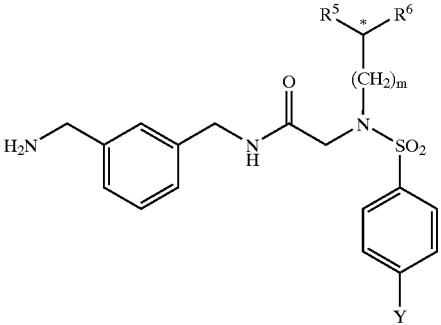

| | | | | | | |
|---|---|---|---|---|---|---|
| 344 | 1 | 2-methoxyphenyl | H | — | 0 | 2-methylphenyl |
| 345 | 1 | 2-methoxyphenyl | H | — | 0 | 2-chlorophenyl |
| 346 | 1 | 2-methoxyphenyl | H | — | 0 | 2-methoxyphenyl |
| 347 | 1 | 2-methoxyphenyl | H | — | 0 | 2,4-dichlorophenyl |
| 348 | 0 | 2-methoxyphenyl | H | — | 0 | 2-methyl |
| 349 | 0 | 2-methoxyphenyl | H | — | 0 | 2-chlorophenyl |
| 350 | 0 | 2-methoxyphenyl | H | — | 0 | 2-methoxyphenyl |
| 351 | 0 | 2-methoxyphenyl | H | — | 0 | 2,4-dichlorophenyl |
| 390 | 1 | phenyl | $CH_3$ | R | 0 | 2-methylphenyl |
| 391 | 1 | phenyl | $CH_3$ | R | 0 | 2-chlorophenyl |
| 392 | 1 | phenyl | $CH_3$ | R | 0 | 3-fluorophenyl |
| 393 | 1 | phenyl | $CH_3$ | S | 0 | 2-methylphenyl |
| 394 | 1 | phenyl | $CH_3$ | S | 0 | 2-chlorophenyl |
| 395 | 1 | phenyl | $CH_3$ | S | 0 | 3-fluorophenyl |

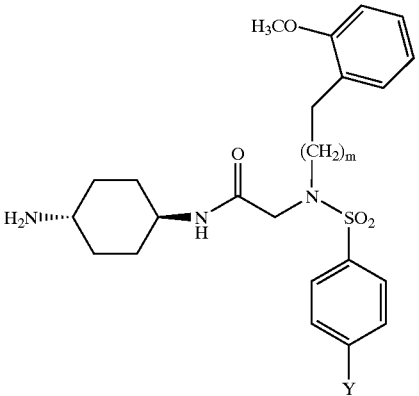

| Cmpd# | m | Y |
|---|---|---|
| 74 | 0 | 2-methylphenyl |
| 75 | 0 | 3-thienyl |
| 76 | 0 | 2-methoxyphenyl |
| 77 | 0 | 4-fluorophenyl |
| 78 | 0 | 2,3-dimethoxyphenyl |
| 79 | 0 | 4-methoxyphenyl |
| 80 | 0 | 4-methylphenyl |
| 81 | 0 | 1-napthyl |
| 82 | 0 | 2-chlorophenyl |
| 83 | 0 | 3-pyridyl |
| 84 | 0 | 2-thienyl |
| 85 | 0 | 3-aminocarbonylphenyl |
| 86 | 0 | phenyl |
| 87 | 0 | 4-chlorophenyl |
| 88 | 0 | 4-[3,5-dimethylisoxazolyl] |
| 89 | 0 | 2-furyl |
| 90 | 0 | 4-cyanophenyl |
| 91 | 0 | 4-pyridyl |
| 92 | 0 | 3-methoxyphenyl |
| 93 | 0 | 4-aminophenyl |
| 94 | 1 | 2-methylphenyl |
| 95 | 1 | 3-thienyl |
| 96 | 1 | 2-methoxyphenyl |
| 97 | 1 | 4-fluorophenyl |
| 98 | 1 | 2,3-dimethyoxyphenyl |

TABLE 1-continued

| | | |
|---|---|---|
| 99 | 1 | 4-methoxyphenyl |
| 100 | 1 | 4-methylphenyl |
| 101 | 1 | 1-napthyl |
| 102 | 1 | 2-chlorophenyl |
| 103 | 1 | 3-pyridyl |
| 104 | 1 | 2-thienyl |
| 105 | 1 | 3-aminocarbonylphenyl |
| 106 | 1 | phenyl |
| 107 | 1 | 4-chlorophenyl |
| 108 | 1 | 4-[3,4-dimethylisoxazolyl] |
| 109 | 1 | 2-furyl |
| 110 | 1 | 4-cyano phenyl |
| 111 | 1 | 4-pyridyl |
| 112 | 1 | 3-methoxyphenyl |
| 113 | 1 | 4-aminophenyl |

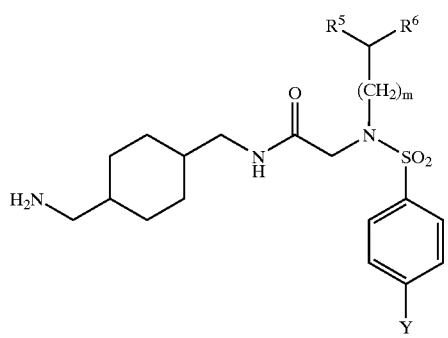

| Cmpd# | m | $R^5$ | $R^6$ | Y |
|---|---|---|---|---|
| 1 | 0 | 2-methoxyphenyl | H | 4-chlorophenyl |
| 2 | 0 | 2-methoxyphenyl | H | 3-trifluoromethylphenyl |
| 3 | 0 | 2-methoxyphenyl | H | 2-chlorophenyl |
| 4 | 0 | 2-methoxyphenyl | H | 2-methylphenyl |
| 5 | 0 | 2-methoxyphenyl | H | 2-methoxyphenyl |
| 6 | 0 | 2-methoxyphenyl | H | 2,4-dichlorophenyl |
| 7 | 0 | 2-methoxyphenyl | H | 3,5-di(trifluoromethyl)phenyl |
| 8 | 0 | 2-methoxyphenyl | H | 3-chloro-4-fluorophenyl |
| 9 | 0 | 2-methoxyphenyl | H | 4-methoxyphenyl |
| 20 | 0 | 3-methoxyphenyl | H | 3-trifluoromethylphenyl |
| 21 | 0 | 3-methoxyphenyl | H | 2-methoxyphenyl |
| 22 | 0 | 3-methoxyphenyl | H | 2,4-dichlorophenyl |
| 23 | 0 | 3-methoxyphenyl | H | 3-fluorophenyl |
| 24 | 0 | 3-methoxyphenyl | H | 3-methoxyphenyl |
| 25 | 0 | 3-methoxyphenyl | H | 4-methylphenyl |
| 26 | 0 | 3-methoxyphenyl | H | 4-fluorophenyl |
| 27 | 0 | 3-methoxyphenyl | H | 3-chloro-4-fluorophenyl |
| 28 | 0 | 3-methoxyphenyl | H | 4-methoxyphenyl |
| 29 | 1 | 2-methoxyphenyl | H | 3-trifluoromethyl phenyl |
| 30 | 1 | 2-methoxyphenyl | H | 3-nitrophenyl |
| 31 | 1 | 2-methoxyphenyl | H | 2-chlorophenyl |
| 32 | 1 | 2-methoxyphenyl | H | 2-methylphenyl |
| 33 | 1 | 2-methoxyphenyl | H | 2-methoxyphenyl |
| 34 | 1 | 2-methoxyphenyl | H | 2,4-dichlorophenyl |
| 35 | 1 | 2-methoxyphenyl | H | phenyl |
| 36 | 1 | 2-methoxyphenyl | H | 3-chlorophenyl |
| 37 | 1 | 2-methoxyphenyl | H | 4-fluorophenyl |
| 38 | 1 | 2-methoxyphenyl | H | 2-trifluoromethyl phenyl |

TABLE 1-continued

| Cmpd# | R⁵ | R⁶ | p | C | X |
|---|---|---|---|---|---|
| 39 | 2-methoxyphenyl | H | 0 | phenyl | — |
| 40 | 2-methoxyphenyl | H | 0 | 2-thienyl | 5-chloro |
| 41 | 2-methoxyphenyl | H | 0 | 1-phenyl | 3-trifluoromethyl |
| 42 | 2-methoxyphenyl | H | 0 | 1-phenyl | 2-trifluoromethyl |
| 43 | 2-methoxyphenyl | H | 0 | 1-phenyl | 3-chloro |
| 44 | 2-methoxyphenyl | H | 0 | 1-phenyl | 3,4-dichloro |
| 45 | 2-methoxyphenyl | H | 0 | 2-napthyl | — |
| 46 | 2-methoxyphenyl | H | 0 | 1-phenyl | 2-chloro |
| 47 | 2-methoxyphenyl | H | 0 | 1-phenyl | 4-chloro |
| 48 | 2-methoxyphenyl | H | 0 | 3-thienyl | 2,5-dichloro |
| 49 | 2-methoxyphenyl | H | 0 | 1-phenyl | 2,4-dichloro |
| 50 | 2-methoxyphenyl | H | 0 | 1-phenyl | 2,6-dichloro |
| 51 | 2-methoxyphenyl | H | 0 | 1-phenyl | 3,5-dichloro |
| 52 | 2-methoxyphenyl | H | 0 | 1-phenyl | 2,5-dichloro |
| 53 | 2-methoxyphenyl | H | 0 | 1-phenyl | 2,3-dichloro |
| 54 | 2-methoxyphenyl | H | 1 | phenyl | — |
| 55 | 2-methoxyphenyl | H | 0 | 1-phenyl | 4-methyl |
| 56 | 2-methoxyphenyl | H | 0 | 1-phenyl | 4-methoxy |
| 57 | 2-methoxyphenyl | H | 0 | 1-napthyl | — |
| 58 | 2-methoxyphenyl | H | 0 | 1-phenyl | 4-fluoro |
| 59 | 2-methoxyphenyl | H | 0 | 1-phenyl | 3,4-dimethoxy |
| 60 | 2-methoxyphenyl | H | 0 | 1-phenyl | 2,5-dimethoxy |
| 61 | 2-methoxyphenyl | H | 0 | 1-phenyl | 2-nitro |
| 62 | 2-methoxyphenyl | H | 0 | 1-phenyl | 4-nitro |
| 63 | 2-methoxyphenyl | H | 0 | 1-phenyl | 3-nitro |
| 64 | 2-methoxyphenyl | H | 0 | 1-phenyl | 4-iodo |
| 65 | 2-methoxyphenyl | H | 0 | 1-phenyl | 4-tert-butyl |
| 66 | 2-methoxyphenyl | H | 0 | 1-phenyl | 2-nitro-4-methoxy |
| 67 | 2-methoxyphenyl | H | 0 | 1-phenyl | 3-methyl-4-methoxy |
| 68 | 2-methoxyphenyl | H | 0 | 1-phenyl | 2-nitro-4-trifluoromethyl |
| 69 | 2-methoxyphenyl | H | 0 | 1-phenyl | 3-fluoro |
| 70 | 2-methoxyphenyl | H | 0 | 1-phenyl | 2-fluoro |
| 71 | 2-methoxyphenyl | H | 0 | 1-phenyl | 4-trifluoromethyl |
| 72 | 2-methoxyphenyl | H | 0 | 1-phenyl | 4-trifluoromethoxy |
| 402 | 2-methoxyphenyl | H | 0 | 1-phenyl | 2,3-dichloro |
| 403 | 3,4-methylene dioxyphenyl | H | 0 | 8-quinolinyl | — |

TABLE 1-continued

| Cmpd # | Stereo | Y |
|---|---|---|
| 372 | R | 2-methylphenyl |
| 373 | R | 2-chlorophenyl |
| 374 | R | 3-fluorophenyl |
| 375 | S | 2-methylphenyl |
| 376 | S | 2-chlorophenyl |
| 377 | S | 3-fluorophenyl |

| Cmpd# | $R^5$ | $R^6$ | Stereo | X | Y |
|---|---|---|---|---|---|
| 10 | 2-methoxyphenyl | H | — | 1,4-phenyl | 3-nitrophenyl |
| 11 | 2-methoxyphenyl | H | — | 1,4-phenyl | 2-chlorophenyl |
| 12 | 2-methoxyphenyl | H | — | 1,4-phenyl | 2-methylphenyl |
| 13 | 2-methoxyphenyl | H | — | 1,4-phenyl | 2-methoxyphenyl |
| 14 | 2-methoxyphenyl | H | — | 1,4-phenyl | 3-fluorophenyl |
| 15 | 2-methoxyphenyl | H | — | 1,4-phenyl | phenyl |
| 16 | 2-methoxyphenyl | H | — | 1,4-phenyl | 3-methoxyphenyl |
| 17 | 2-methoxyphenyl | H | — | 1,4-phenyl | 4-fluorophenyl |
| 18 | 2-methoxyphenyl | H | — | 1,4-phenyl | 2-trifluoromethylphenyl |
| 19 | 2-methoxyphenyl | H | — | 1,4-phenyl | 3-chloro-4-fluorophenyl |
| 197 | phenyl | H | R | 1,4-phenyl | phenyl |
| 207 | phenyl | H | S | 1,4-phenyl | phenyl |
| 208 | phenyl | H | S | 1,4-phenyl | 2-chlorophenyl |
| 209 | phenyl | H | S | 1,4-phenyl | 3-chlorophenyl |
| 210 | phenyl | H | S | 1,4-phenyl | 2-methoxyphenyl |
| 211 | phenyl | H | S | 1,4-phenyl | 3-methoxyphenyl |
| 212 | phenyl | H | S | 1,4-phenyl | 4-methoxyphenyl |
| 213 | phenyl | H | S | 1,4-phenyl | 3-fluorophenyl |
| 214 | phenyl | H | S | 1,4-phenyl | 4-fluorophenyl |
| 215 | phenyl | H | S | 1,4-phenyl | 2-methylphenyl |
| 216 | phenyl | H | S | 1,4-phenyl | 4-methylphenyl |
| 217 | 2-methoxyphenyl | H | — | 1,2-phenyl | 2-thienyl |
| 218 | 2-methoxyphenyl | H | — | 1,2-phenyl | 2-methylphenyl |
| 219 | 2-methoxyphenyl | H | — | 1,2-phenyl | 3-thienyl |
| 220 | 2-methoxyphenyl | H | — | 1,2-phenyl | 2-methoxyphenyl |
| 221 | 2-methoxyphenyl | H | — | 1,2-phenyl | 4-fluorophenyl |
| 222 | 2-methoxyphenyl | H | — | 1,2-phenyl | 4-methoxyphenyl |

TABLE 1-continued

| | | | | |
|---|---|---|---|---|
| 223 | 2-methoxyphenyl | H | — | 1,2-phenyl | 4-methylphenyl |
| 224 | 2-methoxyphenyl | H | — | 1,2-phenyl | 1-napthyl |
| 225 | 2-methoxyphenyl | H | — | 1,2-phenyl | 4-chlorophenyl |
| 226 | 2-methoxyphenyl | H | — | 1,2-phenyl | 3-methoxy phenyl |
| 227 | 2-methoxyphenyl | H | — | 1,2-phenyl | 3-aminophenyl |
| 228 | 2-methoxyphenyl | H | — | 1,2-phenyl | 3-fluorophenyl |
| 229 | 2-methoxyphenyl | H | — | 1,2-phenyl | 2-fluorophenyl |
| 230 | 2-methoxyphenyl | H | — | 1,2-phenyl | 1-(3,4-methylene dioxyphenyl) |
| 232 | 2-methoxyphenyl | H | — | 1,2-phenyl | phenyl |
| 233 | 2-methoxyphenyl | H | — | 1,2-phenyl | 4-(3,5-dimethyl isoxazole) |
| 234 | 2-methoxyphenyl | H | — | 1,2-phenyl | 4-cyanophenyl |
| 235 | 2-methoxyphenyl | H | — | 1,2-phenyl | 4-pyridyl |
| 236 | 2-methoxyphenyl | H | — | 1,2-phenyl | 2,3,4-trimethoxyphenyl |
| 237 | 2-methoxyphenyl | H | — | 1,2-phenyl | 3-cyanophenyl |
| 238 | 2-methoxyphenyl | H | — | 1,2-phenyl | 2,5-dimethoxy phenyl |
| 239 | 2-methoxyphenyl | H | — | 1,2-phenyl | 2,4-dichloro phenyl |
| 240 | 2-methoxyphenyl | H | — | 1,2-phenyl | 3-trifluoro methylphenyl |
| 241 | 2-methoxyphenyl | H | — | 1,2-phenyl | 4-trifluoro methylphenyl |
| 242 | 2-methoxyphenyl | H | — | 1,2-phenyl | 2-trifluoro methylphenyl |
| 243 | 2-methoxyphenyl | H | — | 1,2-phenyl | 3-methylphenyl |
| 244 | 2-methoxyphenyl | H | — | 1,3-phenyl | 2-methylphenyl |
| 245 | 2-methoxyphenyl | H | — | 1,3-phenyl | 3-thienyl |
| 246 | 2-methoxyphenyl | H | — | 1,3-phenyl | 2-methoxyphenyl |
| 247 | 2-methoxyphenyl | H | — | 1,3-phenyl | 4-fluorophenyl |
| 248 | 2-methoxyphenyl | H | — | 1,3-phenyl | 4-methoxyphenyl |
| 249 | 2-methoxyphenyl | H | — | 1,3-phenyl | 4-methoxyphenyl |
| 250 | 2-methoxyphenyl | H | — | 1,3-phenyl | 1-napthyl |
| 252 | 2-methoxyphenyl | H | — | 1,3-phenyl | 3-pyridyl |
| 253 | 2-methoxyphenyl | H | — | 1,3-phenyl | 4-chlorophenyl |
| 254 | 2-methoxyphenyl | H | — | 1,3-phenyl | 3-methoxyphenyl |
| 255 | 2-methoxyphenyl | H | — | 1,3-phenyl | 3-aminophenyl |
| 256 | 2-methoxyphenyl | H | — | 1,3-phenyl | 3-fluorophenyl |
| 257 | 2-methoxyphenyl | H | — | 1,3-phenyl | 2-fluorophenyl |
| 258 | 2-methoxyphenyl | H | — | 1,3-phenyl | 1-(3,4-methylene dioxyphenyl) |
| 259 | 2-methoxyphenyl | H | — | 1,3-phenyl | 3-chlorophenyl |
| 260 | 2-methoxyphenyl | H | — | 1,3-phenyl | phenyl |
| 261 | 2-methoxyphenyl | H | — | 1,3-phenyl | 4-(3,5-dimethyl isoxazole) |
| 262 | 2-methoxyphenyl | H | — | 1,3-phenyl | 4-cyanophenyl |
| 263 | 2-methoxyphenyl | H | — | 1,3-phenyl | 4-pyridyl |
| 264 | 2-methoxyphenyl | H | — | 1,3-phenyl | 2,3,4-trimethoxyphenyl |
| 265 | 2-methoxyphenyl | H | — | 1,3-phenyl | 4-cyanophenyl |
| 266 | 2-methoxyphenyl | H | — | 1,3-phenyl | 2,5-dimethoxy phenyl |
| 267 | 2-methoxyphenyl | H | — | 1,3-phenyl | 3-trifluoro methylphenyl |
| 268 | 2-methoxyphenyl | H | — | 1,3-phenyl | 4-trifluoro methylphenyl |
| 269 | 2-methoxyphenyl | H | — | 1,3-phenyl | 2-trifluoro methylphenyl |
| 270 | 2-methoxyphenyl | H | — | 1,3-phenyl | 3-methylphenyl |
| 271 | 2-methoxyphenyl | H | — | 2,5-thienyl | 2-thienyl |
| 272 | 2-methoxyphenyl | H | — | 2,5-thienyl | 2-methylphenyl |
| 273 | 2-methoxyphenyl | H | — | 2,5-thienyl | 3-thienyl |
| 274 | 2-methoxyphenyl | H | — | 2,5-thienyl | 2-methoxyphenyl |
| 275 | 2-methoxyphenyl | H | — | 2,5-thienyl | 4-fluorophenyl |
| 276 | 2-methoxyphenyl | H | — | 2,5-thienyl | 4-methoxyphenyl |
| 277 | 2-methoxyphenyl | H | — | 2,5-thienyl | 4-methylphenyl |
| 279 | 2-methoxyphenyl | H | — | 2,5-thienyl | 2-chlorophenyl |
| 280 | 2-methoxyphenyl | H | — | 2,5-thienyl | 3-pyridyl |
| 281 | 2-methoxyphenyl | H | — | 2,5-thienyl | 4-chlorophenyl |
| 282 | 2-methoxyphenyl | H | — | 2,5-thienyl | 3-methoxyphenyl |
| 283 | 2-methoxyphenyl | H | — | 2,5-thienyl | 3-aminophenyl |
| 284 | 2-methoxyphenyl | H | — | 2,5-thienyl | 3-fluorophenyl |
| 285 | 2-methoxyphenyl | H | — | 2,5-thienyl | 2-fluorophenyl |
| 287 | 2-methoxyphenyl | H | — | 2,5-thienyl | 3-chlorophenyl |
| 288 | 2-methoxyphenyl | H | — | 2,5-thienyl | phenyl |

TABLE 1-continued

| | | | | |
|---|---|---|---|---|
| 289 | 2-methoxyphenyl | H | — | 2,5-thienyl | 4-(3,5-dimethyl isoxazole) |
| 290 | 2-methoxyphenyl | H | — | 2,5-thienyl | 4-cyanophenyl |
| 291 | 2-methoxyphenyl | H | — | 2,5-thienyl | 4-pyridyl |
| 292 | 2-methoxyphenyl | H | — | 2,5-thienyl | 2,3,4,-trimethoxyphenyl |
| 293 | 2-methoxyphenyl | H | — | 2,5-thienyl | 3-cyanophenyl |
| 294 | 2-methoxyphenyl | H | — | 2,5-thienyl | 2-furyl |
| 295 | 2-methoxyphenyl | H | — | 2,5-thienyl | 2,5-dimethoxy phenyl |
| 296 | 2-methoxyphenyl | H | — | 2,5-thienyl | 2,4-dichloro phenyl |
| 297 | 2-methoxyphenyl | H | — | 2,5-thienyl | 3-trifluoro methylphenyl |
| 298 | 2-methoxyphenyl | H | — | 2,5-thienyl | 4-trifluoro methylphenyl |
| 299 | 2-methoxyphenyl | H | — | 2,5-thienyl | 2-trifluoro methylphenyl |
| 300 | 2-methoxyphenyl | H | — | 2,5-thienyl | 3-methylphenyl |

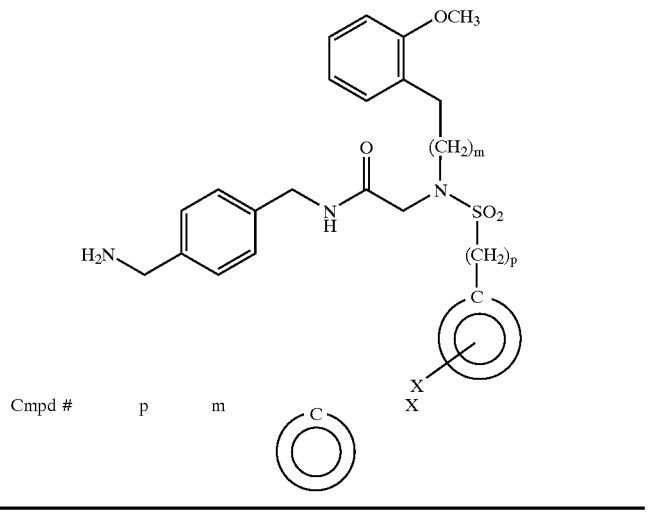

| Cmpd # | p | m | C | X |
|---|---|---|---|---|
| 114 | 0 | 1 | 2-thienyl | 5-chloro |
| 115 | 0 | 1 | phenyl | 3-trifluoromethyl |
| 116 | 0 | 1 | phenyl | 2-trifluoromethyl |
| 117 | 0 | 1 | phenyl | 3-chloro |
| 118 | 0 | 1 | phenyl | 3,4-dichloro |
| 119 | 0 | 1 | 2-napthyl | — |
| 120 | 0 | 1 | phenyl | 2-chloro |
| 121 | 0 | 1 | phenyl | 2,5-dimethoxy |
| 122 | 0 | 1 | phenyl | 2,4-dichloro |
| 123 | 0 | 1 | phenyl | 2,6-dichloro |
| 124 | 0 | 1 | phenyl | 2,5-dichloro |
| 125 | 0 | 1 | phenyl | 3,5-dichloro |
| 126 | 0 | 1 | 2-thienyl | 4,5-dichloro |
| 127 | 1 | 1 | phenyl | — |
| 128 | 0 | 1 | phenyl | 4-methoxy |
| 129 | 0 | 1 | 1-napthyl | — |
| 130 | 0 | 1 | phenyl | 4-fluoro |
| 131 | 0 | 1 | phenyl | 3-fluoro |
| 132 | 0 | 1 | phenyl | 2-fluoro |
| 133 | 0 | 1 | phenyl | 3,4-dimethoxy |
| 134 | 0 | 1 | phenyl | 2-nitro |
| 135 | 0 | 1 | phenyl | 3-nitro |
| 136 | 0 | 1 | phenyl | 4-nitro |
| 137 | 0 | 1 | phenyl | 4-iodo |
| 138 | 0 | 1 | phenyl | 4-t-butyl |
| 139 | 0 | 1 | phenyl | 2-nitro-4-methoxy |
| 140 | 0 | 1 | phenyl | 2-methoxy-5-methyl |
| 141 | 0 | 1 | 2-thienyl | 4-nitro-5-chloro |
| 142 | 0 | 1 | phenyl | 2-nitro-4-trifluoro methyl |
| 143 | 0 | 1 | phenyl | 4-trifluoromethyl |
| 144 | 0 | 1 | phenyl | 4-trifluoromethoxy |
| 147 | 0 | 1 | 2-thienyl | — |
| 148 | 0 | 1 | phenyl | 4-methyl |
| 149 | 0 | 1 | phenyl | 4-chloro |

TABLE 1-continued

| | | | | |
|---|---|---|---|---|
| 150 | 0 | 1 | phenyl | — |
| 404 | 0 | 0 | 1-phenyl | 2,3-dichloro |

| Cmpd# | $R^5$ | | | Y |
|---|---|---|---|---|
| 73 | 2-methoxyphenyl | 2,-thienyl | | 5-(2-methylthio-pyrimidyl) |
| 405 | 3,4-methylene dioxyphenyl | 8-quinolinyl | | — |

| Cmpd # | $R^6$ | $R^5$ | Stereo | Z | | Y |
|---|---|---|---|---|---|---|
| 145 | 2-methoxy phenyl | H | — | $SO_2$ | 2,5-thienyl | 2-pyridyl |
| 146 | 2-methoxy phenyl | H | — | $SO_2$ | 2,5-thienyl | 5-(2-methylthio-pyrimidyl) |
| 198 | phenyl | $CH_3$ | R | $SO_2$ | 1,4-phenyl | 2-chlorophenyl |
| 199 | phenyl | $CH_3$ | R | $SO_2$ | 1,4-phenyl | 3-chlorophenyl |
| 200 | phenyl | $CH_3$ | R | $SO_2$ | 1,4-phenyl | 2-methoxyphenyl |
| 201 | phenyl | $CH_3$ | R | $SO_2$ | 1,4-phenyl | 3-methoxyphenyl |
| 202 | phenyl | $CH_3$ | R | $SO_2$ | 1,4-phenyl | 4-methoxyphenyl |
| 203 | phenyl | $CH_3$ | R | $SO_2$ | 1,4-phenyl | 3-fluorophenyl |
| 204 | phenyl | $CH_3$ | R | $SO_2$ | 1,4-phenyl | 4-fluorophenyl |
| 205 | phenyl | $CH_3$ | R | $SO_2$ | 1,4-phenyl | 2-methylphenyl |
| 206 | phenyl | $CH_3$ | R | $SO_2$ | 1,4-phenyl | 4-methylphenyl |
| 231 | 2-methoxy phenyl | H | — | $SO_2$ | 1,2-phenyl | 3-chlorophenyl |
| 251 | 2-methoxy phenyl | H | — | $SO_2$ | 1,3-phenyl | 2-chlorophenyl |
| 278 | 2-methoxy phenyl | H | — | $SO_2$ | 2,5-thienyl | 1-naphthyl |
| 286 | 2-methoxy phenyl | H | — | $SO_2$ | 2,5-thienyl | 1-(3,4-methylene dioxyphenyl) |
| 301 | phenyl | $CH_3$ | R | $SO_2$ | 1,4-phenyl | 2-fluorophenyl |
| 302 | phenyl | $CH_3$ | R | $SO_2$ | 1,4-phenyl | 2,6-dichlorophenyl |
| 303 | phenyl | $CH_3$ | R | $SO_2$ | 1,4-phenyl | 2,4-dichlorophenyl |
| 304 | phenyl | $CH_3$ | R | $SO_2$ | 1,4-phenyl | 2-trifluoromethyl phenyl |
| 305 | phenyl | $CH_3$ | R | $SO_2$ | 1,4-phenyl | 2,4,6-trimethyl phenyl |
| 306 | phenyl | $CH_3$ | S | $SO_2$ | 1,4-phenyl | 2-fluorophenyl |
| 307 | phenyl | $CH_3$ | S | $SO_2$ | 1,4-phenyl | 2,6-difluorophenyl |
| 308 | phenyl | $CH_3$ | S | $SO_2$ | 1,4-phenyl | 2,4-dichlorophenyl |
| 309 | phenyl | $CH_3$ | S | $SO_2$ | 1,4-phenyl | 2-trifluoromethyl phenyl |

TABLE 1-continued

| | | | | | | |
|---|---|---|---|---|---|---|
| 310 | phenyl | CH₃ | S | SO₂ | 1,4-phenyl | 2,4,6-trimethylphenyl |
| 311 | phenyl | CH₃ | Mix | SO₂ | 1,4-phenyl | 2-methylphenyl |
| 312 | phenyl | CH₃ | Mix | SO₂ | 1,4-phenyl | 2-chlorophenyl |
| 313 | phenyl | CH₃ | Mix | SO₂ | 1,4-phenyl | 3-fluorophenyl |
| 314 | 4-chloro phenyl | CH₃ | Mix | SO₂ | 1,4-phenyl | 2-methylphenyl |
| 315 | 4-chloro phenyl | CH₃ | Mix | SO₂ | 1,4-phenyl | 2-chlorophenyl |
| 316 | 4-chloro phenyl | CH₃ | Mix | SO₂ | 1,4-phenyl | 3-fluorophenyl |
| 317 | 4-chloro phenyl | cyclopropyl | — | SO₂ | 1,4-phenyl | 2-methylphenyl |
| 318 | 4-chloro phenyl | cyclopropyl | — | SO₂ | 1,4-phenyl | 2-chlorophenyl |
| 319 | 4-chloro phenyl | cyclopropyl | — | SO₂ | 1,4-phenyl | 3-fluorophenyl |
| 323 | phenyl | H | — | SO₂ | 1,4-phenyl | 2-methylphenyl |
| 324 | phenyl | H | — | SO₂ | 1,4-phenyl | 2-chlorophenyl |
| 325 | phenyl | H | — | SO₂ | 1,4-phenyl | 3-fluorophenyl |
| 412 | phenyl | CH₃ | R | SO₂ | 1,4-phenyl | phenyl |
| 413 | phenyl | CH₃ | R | SO₂ | 1,4-phenyl | 3-nitrophenyl |
| 414 | phenyl | CH₃ | R | SO₂ | 1,4-phenyl | 4-fluorophenyl |
| 415 | phenyl | CH₃ | R | SO₂ | 1,4-phenyl | 2-methylphenyl |
| 416 | phenyl | CH₃ | R | SO₂ | 1,4-phenyl | 3-trifluoromethyl phenyl |
| 417 | phenyl | CH₃ | R | SO₂ | 1,4-phenyl | 4-trifluoromethyl phenyl |
| 418 | phenyl | CH₃ | R | SO₂ | 1,4-phenyl | 3-chlorophenyl |
| 419 | phenyl | CH₃ | R | SO₂ | 1,4-phenyl | 3-methoxy phenyl |
| 420 | phenyl | CH₃ | R | SO₂ | 1,4-phenyl | 2-trifluoromethyl phenyl |
| 421 | phenyl | CH₃ | R | SO₂ | 1,4-phenyl | 2-methoxy phenyl |
| 422 | phenyl | CH₃ | R | SO₂ | 1,4-phenyl | 4-trifluoro methoxyphenyl |
| 423 | phenyl | CH₃ | R | SO₂ | 1,4-phenyl | 3-fluorophenyl |
| 424 | phenyl | CH₃ | R | SO₂ | 1,4-phenyl | 2-naphthyl |
| 425 | phenyl | CH₃ | R | SO₂ | 1,4-phenyl | 3-chloro-4-fluorophenyl |
| 426 | phenyl | CH₃ | R | SO₂ | 1,4-phenyl | 3-bromophenyl |
| 427 | phenyl | CH₃ | R | SO₂ | 1,4-phenyl | 4-chlorophenyl |
| 428 | phenyl | CH₃ | R | SO₂ | 1,4-phenyl | 3,5-dichloro phenyl |
| 429 | phenyl | CH₃ | R | SO₂ | 1,4-phenyl | 2,4-dichloro phenyl |
| 430 | phenyl | CH₃ | R | SO₂ | 1,4-phenyl | 3,5-ditrifluoro methylphenyl |
| 432 | phenyl | CH₃ | R | SO₂ | 1,4-phenyl | 2-benzofuryl |
| 433 | phenyl | CH₃ | R | SO₂ | 1,4-phenyl | 2-(t-butylamino sulfonyl)phenyl |
| 434 | phenyl | CH₃ | R | SO₂ | 1,4-phenyl | 4-cyanophenyl |
| 435 | phenyl | CH₃ | R | SO₂ | 1,4-phenyl | 3-cyanophenyl |
| 436 | phenyl | CH₃ | R | SO₂ | 1,4-phenyl | 3-carboxyphenyl |
| 437 | phenyl | CH₃ | R | SO₂ | 1,4-phenyl | 2[(di-i-propyl) aminocarbonyl] phenyl |
| 438 | phenyl | CH₃ | R | SO₂ | 1,4-phenyl | 4-(3,5-dimethyl) isoxazolyl |
| 439 | phenyl | CH₃ | R | SO₂ | 1,4-phenyl | 2-methoxy-5-formylphenyl |
| 440 | phenyl | CH₃ | R | SO₂ | 1,4-phenyl | 4-pyridyl |
| 441 | phenyl | CH₃ | R | SO₂ | 1,4-phenyl | 2,3,4-tri methoxyphenyl |
| 442 | phenyl | CH₃ | R | SO₂ | 1,4-phenyl | phenoxathiinyl |
| 443 | phenyl | CH₃ | R | SO₂ | 1,4-phenyl | 2-(5-formyl)furyl |
| 444 | phenyl | CH₃ | R | SO₂ | 1,4-phenyl | 2-(4-methyl) thienyl |
| 446 | phenyl | CH₃ | R | SO₂ | 1,4-phenyl | dibenzothienyl |
| 447 | phenyl | CH₃ | R | SO₂ | 1,4-phenyl | dianthrenyl |
| 448 | phenyl | CH₃ | R | SO₂ | 1,4-phenyl | dibenzothienyl |
| 449 | phenyl | CH₃ | R | SO₂ | 1,4-phenyl | 3-benzothienyl |
| 450 | phenyl | CH₃ | R | SO₂ | 1,4-phenyl | 3,4-dimethoxy phenyl |
| 451 | phenyl | CH₃ | R | SO₂ | 1,4-phenyl | 2-fluorophenyl |
| 452 | phenyl | CH₃ | R | SO₂ | 1,4-phenyl | 1-naphthyl |
| 453 | phenyl | CH₃ | R | SO₂ | 1,4-phenyl | 4-methoxy phenyl |
| 454 | phenyl | CH₃ | R | SO₂ | 1,4-phenyl | 3-fluoro-4-chlorophenyl |
| 455 | phenyl | CH₃ | R | SO₂ | 1,4-phenyl | 2-nitrophenyl |

TABLE 1-continued

| Cmpd # | | | | | |
|---|---|---|---|---|---|
| 456 | phenyl | CH$_3$ | R | SO$_2$ | 1,4-phenyl | 3-biphenyl |
| 457 | phenyl | CH$_3$ | R | SO$_2$ | 1,4-phenyl | 2-(t-butylcarbonyl amino)-3-methoxy phenyl |
| 458 | phenyl | CH$_3$ | R | SO$_2$ | 1,4-phenyl | 2-(t-butyl carbonyl amino)-5-methoxy phenyl |
| 459 | phenyl | CH$_3$ | R | SO$_2$ | 1,4-phenyl | 2-(5-formyl)furyl |
| 460 | phenyl | CH$_3$ | R | SO$_2$ | 1,4-phenyl | 2,5-dimethoxy phenyl |
| 461 | phenyl | CH$_3$ | R | SO$_2$ | 1,4-phenyl | 2-(di(i-propyl) aminocarbonyl)-3-methoxyphenyl |
| 462 | phenyl | CH$_3$ | R | SO$_2$ | 1,4-phenyl | 4-methylthio phenyl |
| 463 | phenyl | CH$_3$ | R | SO$_2$ | 1,4-phenyl | 2,4,6-tri methylphenyl |
| 464 | phenyl | CH$_3$ | R | SO$_2$ | 1,4-phenyl | 3-methylphenyl |
| 465 | phenyl | CH$_3$ | R | SO$_2$ | 1,4-phenyl | 4-methylphenyl |
| 466 | phenyl | CH$_3$ | R | SO$_2$ | 1,4-phenyl | 3-pyridyl |
| 467 | phenyl | CH$_3$ | R | SO$_2$ | 1,4-phenyl | 3-aminophenyl |
| 468 | phenyl | CH$_3$ | R | SO$_2$ | 1,4-phenyl | 3-methylcarbonyl aminophenyl |
| 477 | phenyl | CH$_3$ | R | C(O) | 1,4-phenyl | 2-chlorophenyl |
| 478 | phenyl | CH$_3$ | R | C(O) | 1,4-phenyl | 2-methylphenyl |
| 479 | phenyl | CH$_3$ | R | C(O) | 1,4-phenyl | 3-fluorophenyl |
| 480 | phenyl | CH$_3$ | R | C(O) | 1,4-phenyl | 2-bromophenyl |
| 481 | phenyl | CH$_3$ | R | C(O) | 1,4-phenyl | 2,5-dichloro phenyl |
| 521 | phenyl | CH$_3$ | R | SO$_2$ | 1,4-phenyl | 2-methyl-3-chlorophenyl |
| 522 | phenyl | CH$_3$ | R | SO$_2$ | 1,4-phenyl | 2-chloro-5-methylphenyl |
| 523 | phenyl | CH$_3$ | R | SO$_2$ | 1,4-phenyl | 2-methyl-5-chlorophenyl |
| 524 | phenyl | CH$_3$ | R | SO$_2$ | 1,4-phenyl | 3-chloro-4-methylphenyl |
| 525 | phenyl | CH$_3$ | R | SO$_2$ | 1,4-phenyl | 2-chloro-6-methylphenyl |
| 526 | phenyl | CH$_3$ | R | SO$_2$ | 1,4-phenyl | 2-chloro-4-methylphenyl |
| 550 | 3-trifluoro methyl phenyl | H | — | SO$_2$ | 1,4-phenyl | phenyl |
| 590 | phenyl | CH$_3$ | R | C(O)NH | 1,4-phenyl | phenyl |
| 591 | phenyl | CH$_3$ | S | C(O)NH | 1,4-phenyl | phenyl |

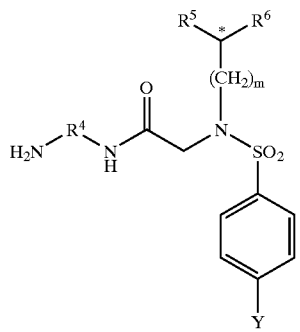

| Cmpd # | R$^4$ | m | R$^5$ | R$^6$ | Stereo | Y |
|---|---|---|---|---|---|---|
| 378 | 1,5-n-pentyl | 1 | phenyl | CH$_3$ | R | 2-methylphenyl |
| 379 | 1,5-n-pentyl | 1 | phenyl | CH$_3$ | R | 2-chlorophenyl |
| 380 | 1,5-n-pentyl | 1 | phenyl | CH$_3$ | R | 3-fluorophenyl |
| 381 | 1,5-n-pentyl | 1 | phenyl | CH$_3$ | S | 2-methylphenyl |
| 382 | 1,5-n-pentyl | 1 | phenyl | CH$_3$ | S | 2-chlorophenyl |
| 383 | 1,5-n-pentyl | 1 | phenyl | CH$_3$ | S | 3-fluorophenyl |
| 352 | 1,5-n-pentyl | 1 | 2-methoxyphenyl | H | — | 2-methylphenyl |
| 353 | 1,6-n-hexyl | 1 | 2-methoxyphenyl | H | — | 2-chlorophenyl |
| 354 | 1,6-n-hexyl | 1 | 2-methoxyphenyl | H | — | 2-methoxyphenyl |
| 355 | 1,6-n-hexyl | 1 | 2-methoxyphenyl | H | — | 2,4-dichlorophenyl |
| 356 | 1,6-n-hexyl | 0 | 2-methoxyphenyl | H | — | 2-methylphenyl |
| 357 | 1,6-n-hexyl | 0 | 2-methoxyphenyl | H | — | 2-chlorophenyl |
| 358 | 1,6-n-hexyl | 0 | 2-methoxyphenyl | H | — | 2-methoxyphenyl |

TABLE 1-continued

| | | | | | |
|---|---|---|---|---|---|
| 359 | 1,6-n-hexyl | 0 | 2-methoxyphenyl | H | — | 2,4-dichlorophenyl |
| 396 | 1,6-n-hexyl | 1 | phenyl | CH$_3$ | R | 2-methylphenyl |
| 397 | 1,6-n-hexyl | 1 | phenyl | CH$_3$ | R | 2-chlorophenyl |
| 398 | 1,6-n-hexyl | 1 | phenyl | CH$_3$ | R | 3-fluorophenyl |
| 399 | 1,6-n-hexyl | 1 | phenyl | CH$_3$ | S | 2-methylphenyl |
| 400 | 1,6-n-hexyl | 1 | phenyl | CH$_3$ | S | 2-chlorophenyl |
| 401 | 1,6-n-hexyl | 1 | phenyl | CH$_3$ | S | 3-fluorophenyl |

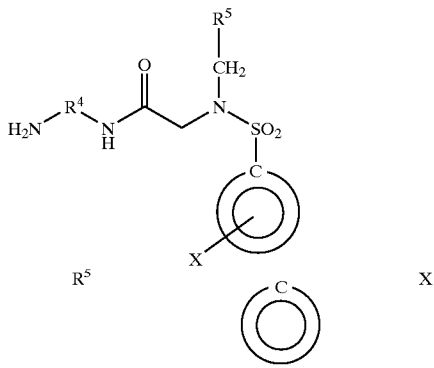

| Cmpd # | R$^4$ | R$^5$ | C | X |
|---|---|---|---|---|
| 406 | 1,4-n-butyl | 2-methoxyphenyl | 1-phenyl | 2,3-dichloro |
| 407 | 1,6-n-hexyl | 2-methoxyphenyl | 1-phenyl | 2,3-dichloro |
| 408 | 1,4-n-butyl | 3,4-methylene dioxyphenyl | 8-quinolinyl | — |
| 409 | 1,6-n-hexyl | 3,4-methylene dioxyphenyl | 8-quinolinyl | — |

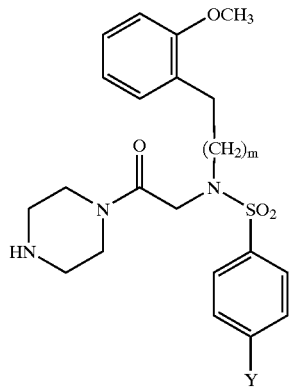

| Cmpd # | m | Y |
|---|---|---|
| 151 | 1 | 2-methylphenyl |
| 152 | 1 | 3-thienyl |
| 153 | 1 | 2-methoxyphenyl |
| 154 | 1 | 4-fluorophenyl |
| 155 | 1 | 2,4-dimethoxyphenyl |
| 156 | 1 | 4-methoxyphenyl |
| 157 | 1 | 4-methylphenyl |
| 158 | 1 | 1-napthyl |
| 159 | 1 | 2-chlorophenyl |
| 160 | 1 | 3-pyridyl |
| 161 | 1 | 2-thienyl |
| 162 | 1 | 3-acetamidophenyl |
| 163 | 1 | phenyl |
| 164 | 1 | 4-chlorophenyl |
| 165 | 1 | 4-[3,5-dimethylisoxazolyl] |
| 166 | 1 | 3-chlorophenyl |
| 167 | 1 | 4-cyanophenyl |
| 168 | 1 | 4-pyridyl |
| 169 | 1 | 3-methoxyphenyl |
| 170 | 1 | 3-aminophenyl |
| 171 | 1 | 3-fluorophenyl |
| 172 | 1 | 2-fluorophenyl |
| 173 | 1 | 3,4-methylenedioxyphenyl |
| 174 | 0 | 2-methylphenyl |

TABLE 1-continued

| | | |
|---|---|---|
| 175 | 0 | 3-thienyl |
| 176 | 0 | 2-methoxyphenyl |
| 177 | 0 | 4-fluorophenyl |
| 178 | 0 | 2,4-dimethoxyphenyl |
| 179 | 0 | 4-methoxyphenyl |
| 180 | 0 | 4-methylphenyl |
| 181 | 0 | 1-napthyl |
| 182 | 0 | 2-chlorophenyl |
| 183 | 0 | 3-pyridyl |
| 184 | 0 | 2-thienyl |
| 185 | 0 | 3-acetamidophenyl |
| 186 | 0 | phenyl |
| 187 | 0 | 4-chlorophenyl |
| 188 | 0 | 4-[3,5-dimethylisoxazolyl] |
| 189 | 0 | 3-chlorophenyl |
| 190 | 0 | 4-cyanophenyl |
| 191 | 0 | 4-pyridyl |
| 192 | 0 | 3-methoxyphenyl |
| 193 | 0 | 3-aminophenyl |
| 194 | 0 | 3-fluorophenyl |
| 195 | 0 | 2-fluorophenyl |
| 196 | 0 | 3,4-methylenedioxyphenyl |

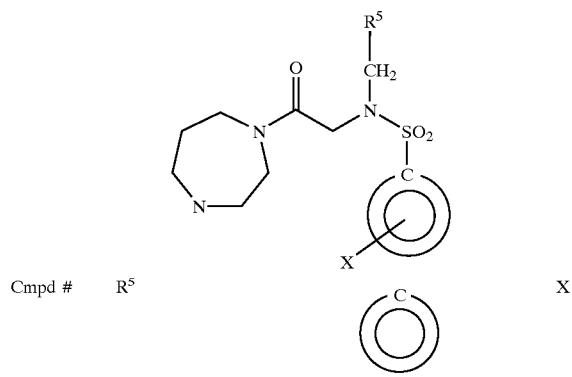

| Cmpd # | $R^5$ | C | X |
|---|---|---|---|
| 410 | 2-methoxyphenyl | 1-phenyl | 2,3-dichloro |
| 411 | 3,4-methylenedioxyphenyl | 8-quinolinyl | — |

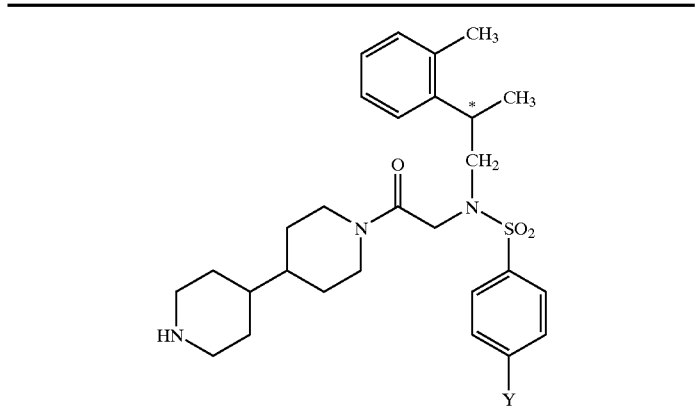

| Cmpd # | Stereo | Y |
|---|---|---|
| 366 | R | 2-methylphenyl |
| 367 | R | 2-chlorophenyl |
| 368 | R | 3-fluorophenyl |
| 369 | S | 2-methylphenyl |
| 370 | S | 2-chlorophenyl |
| 371 | S | 3-fluorophenyl |

TABLE 1-continued

| Cmpd # | Y |
|---|---|
| 320 | 2-methylphenyl |
| 321 | 2-chlorophenyl |
| 322 | 3-fluorophenyl |

| Cmpd # | Stereo | n | X |
|---|---|---|---|
| 431 | R | 1 | 4-n-butyl |
| 445 | R | 0 | — |
| 469 | R | 1 | 4-bromo |
| 470 | S | 1 | 4-bromo |
| 551 | R | 1 | 4-methoxy |
| 552 | R | 1 | 4-trifluoromethyl |
| 553 | R | 1 | 4-isopropyl |
| 554 | R | 1 | 4-n-propyl |
| 555 | R | 1 | 4-t-butyl |
| 556 | R | 1 | 4-n-pentyl |
| 557 | R | 1 | 3-methoxy |
| 558 | S | 1 | 4-methoxy |
| 559 | S | 1 | 4-trifluoromethyl |
| 560 | S | 1 | 4-isopropyl |
| 561 | S | 1 | 4-n-propyl |
| 562 | S | 1 | 4-t-butyl |
| 563 | S | 1 | 4-n-pentyl |
| 564 | S | 1 | 3-methoxy |

TABLE 1-continued

[Structure diagram: R¹R²N-CH₂-(1,4-phenyl)-CH₂-NH-C(O)-CH₂-N(SO₂-C₆H₄-Y)-CH₂-CH(CH₃)-phenyl with stereocenter marked *]

| Cmpd # | R¹ | R² | Stereo | Y |
|---|---|---|---|---|
| 471 | methyl | methyl | R | 2-chlorophenyl |
| 472 | ethyl | ethyl | R | 2-chlorophenyl |
| 473 | H | methylcarbonyl | R | 2-chlorophenyl |
| 474 | methyl | methyl | S | 2-methylphenyl |
| 475 | ethyl | ethyl | S | 2-methylphenyl |
| 476 | H | methylcarbonyl | S | 2-methylphenyl |

[Structure diagram: H₂N-R⁴-NH-C(O)-CH₂-N(L)-SO₂-(4-biphenyl)-2'-Cl]

| Cmpd # | R⁴ | L |
|---|---|---|
| 483 | —CH₂-(1,4-phenyl)-CH₂— | 4-methyoxyphenylethyl |
| 484 | —CH₂-(1,4-phenyl)-CH₂— | 3,6-dimethoxyphenylethyl |
| 485 | —CH₂-(1,4-phenyl)-CH₂— | 2,3-dimethoxyphenylethyl |
| 486 | —CH₂-(1,4-phenyl)-CH₂— | 1-cyclohexenylethyl |
| 487 | —CH₂-(1,4-phenyl)-CH₂— | 3-bromo-4,5-dimethylphenylethyl |
| 488 | —CH₂-(1,4-phenyl)-CH₂— | 2-chlorphenylethyl |
| 489 | —CH₂-(1,4-phenyl)-CH₂— | 3-chlorophenylethyl |
| 490 | —CH₂-(1,4-phenyl)-CH₂— | 2,4-dichlorophenylethyl |
| 491 | —CH₂-(1,4-phenyl)-CH₂— | 2,6-dichlorophenylethyl |
| 492 | —CH₂-(1,4-phenyl)-CH₂— | 2-trifluoromethylphenylethyl |
| 493 | —CH₂-(1,4-phenyl)-CH₂— | 3,4-dimethylphenylethyl |
| 494 | —CH₂-(1,4-phenyl)-CH₂— | 3,5-dimethylphenylethyl |
| 495 | —CH₂-(1,4-phenyl)-CH₂— | 3-methoxyphenylethyl |
| 496 | —CH₂-(1,4-phenyl)-CH₂— | 3-(2-chlorophenyl)-4,5-dimethoxyphenylethyl |
| 501 | n-hexyl | 3,4-dimethoxyphenylethyl |
| 502 | n-hexyl | 4-methoxyphenylethyl |
| 503 | n-hexyl | 2,3-dimethoxyphenylethyl |
| 504 | n-hexyl | 3-bromo-4,5-dimethoxyphenylethyl |
| 505 | n-hexyl | 2-chlorophenylethyl |
| 506 | n-hexyl | 3-chlorophenylethyl |
| 507 | n-hexyl | 2,4-dichlorophenylethyl |
| 508 | n-hexyl | 2,6-dichlorophenylethyl |
| 509 | n-hexyl | 3,5-dimethoxyphenylethyl |
| 510 | n-hexyl | 3-methoxyphenylethyl |
| 511 | n-hexyl | 2,5-dimethoxyphenylethyl |
| 512 | n-hexyl | 1-cyclohexenylethyl |
| 513 | n-hexyl | 3-(2-chlorophenyl)-3,4-dimethoxyphenylethyl |

TABLE 1-continued

| | | |
|---|---|---|
| 514 | n-hexyl | 2-fluorophenylethyl |
| 515 | n-hexyl | 2-trifluoromethylphenylethyl |
| 527 | —CH$_2$-(1,4-phenyl)-CH$_2$— | 2-nitrophenylethyl |
| 528 | —CH$_2$-(1,4-phenyl)-CH$_2$— | 2-aminophenylethyl |
| 529 | —CH$_2$-(1,4-phenyl)-CH$_2$— | 2-dimethylaminophenylethyl |
| 530 | —CH$_2$-(1,4-phenyl)-CH$_2$— | 2-(methylcarbonylamino)phenylethyl |
| 531 | —CH$_2$-(1,4-phenyl)-CH$_2$— | 2-(methylsulfonylamino)phenylethyl |
| 532 | —CH$_2$-(1,4-phenyl)-CH$_2$— | CH$_2$—C(CH$_3$)$_2$-phenyl |
| 533 | —CH$_2$-(1,4-phenyl)-CH$_2$— | CH$_2$—C(OCH$_3$)-phenyl |
| 534 | —CH$_2$-(1,4-phenyl)-CH$_2$— | CH$_2$—CH(CH$_3$)-(2-methoxyphenyl) |
| 535 | —CH$_2$-(1,4-phenyl)-CH$_2$— | bicyclo[4.2.0]octa-1,3,5-triene |
| 536 | —CH$_2$-(1,4-phenyl)-CH$_2$— | CH$_2$—CH(cyclohexyl)-phenyl |
| 537 | —CH$_2$-(1,4-phenyl)-CH$_2$— | CH$_2$—CH(cyclobutyl)-phenyl |
| 538 | —CH$_2$-(1,4-phenyl)-CH$_2$— | CH$_2$—CH(ethyl)-phenyl |
| 539 | —CH$_2$-(1,4-phenyl)-CH$_2$— | 2,3-dihydro-1H-indene |
| 540 | —CH$_2$-(1,4-phenyl)-CH$_2$— | CH(phenyl)$_2$ |
| 541 | —CH$_2$-(1,4-phenyl)-CH$_2$— | 2-methylphenylethyl |
| 542 | —CH$_2$-(1,4-phenyl)-CH$_2$— | 3-fluorophenylethyl |
| 543 | —CH$_2$-(1,4-phenyl)-CH$_2$— | 3,4-methylenedioxyphenyl |
| 544 | —CH$_2$-(1,4-phenyl)-CH$_2$— | 2-pyridylethyl |
| 545 | —CH$_2$-(1,4-phenyl)-CH$_2$— | 2-thienylethyl |
| 546 | —CH$_2$-(1,4-phenyl)-CH$_2$— | 2-(N-methyl)-pyrrolidinylethyl |
| 547 | —CH$_2$-(1,4-phenyl)-CH$_2$— | phenylpropyl |
| 548 | —CH$_2$-(1,4-phenyl)-CH$_2$— | 2-ethoxyphenylethyl |
| 549 | —CH$_2$-(1,4-phenyl)-CH$_2$— | 3,4-dichlorophenylethyl |
| 572 | n-hexyl | CH$_2$—CH(OCH$_3$)-phenyl |
| 573 | n-hexyl | CH$_2$—CH(CH$_3$)—(2-methoxyphenyl) |
| 574 | n-hexyl | bicyclo[4.2.0]octa-1,3,5-triene |
| 575 | n-hexyl | CH$_2$—CH(cyclohexyl)-phenyl |
| 576 | n-hexyl | CH$_2$—CH(cyclobutyl)-phenyl |
| 577 | n-hexyl | CH$_2$—CH(ethyl)-phenyl |
| 578 | n-hexyl | 2,3-dihydro-1H-indene |
| 579 | n-hexyl | CH$_2$—CH(phenyl)$_2$ |
| 580 | n-hexyl | 2-methylphenylethyl |
| 581 | n-hexyl | 3-fluorophenylethyl |
| 582 | n-hexyl | 3,4-methylenedioxyphenyl |
| 583 | n-hexyl | 2-pyridylethyl |
| 584 | n-hexyl | 2-thienylethyl |
| 585 | n-hexyl | 2-(N-methylpyrrolidinyl)ethyl |
| 586 | n-hexyl | phenylpropyl |
| 587 | n-hexyl | 2-ethoxyphenylethyl |
| 588 | n-hexyl | 3,4-dichlorophenylethyl |
| 589 | n-hexyl | 3-trifluoromethylphenylethyl |

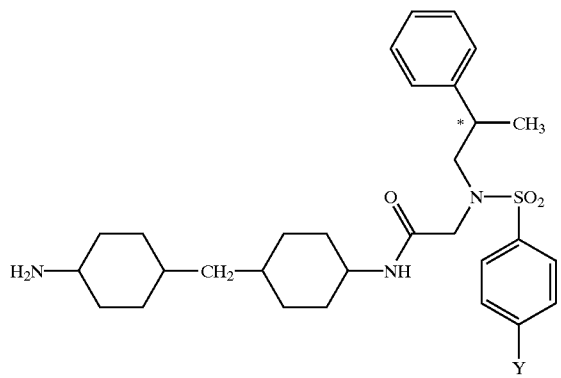

| Cmpd # | Stereo | Y |
|---|---|---|
| 497 | R | 2-chlorophenyl |
| 498 | R | 2-methylphenyl |
| 499 | R | 3-fluorophenyl |
| 500 | S | 2-chlorophenyl | and stereoisomers and pharmaceutically acceptable salts or esters thereof.

In a particularly preferred embodiment of the present invention are compounds of the formula (I) as enumerated in Table 2 below:

TABLE 2
(Structure and Compound #)
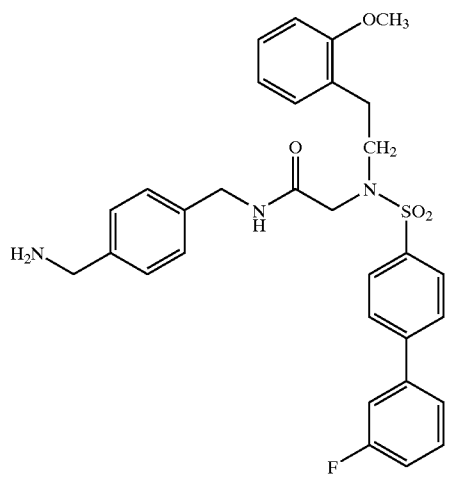
14
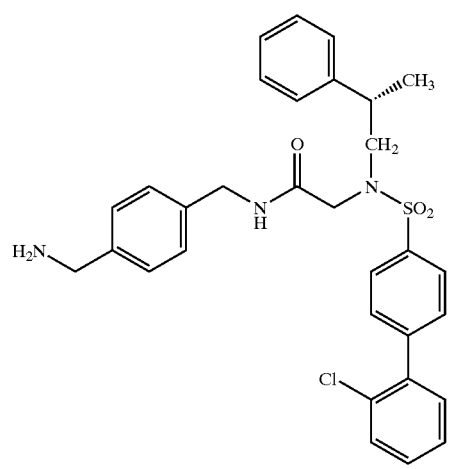
208
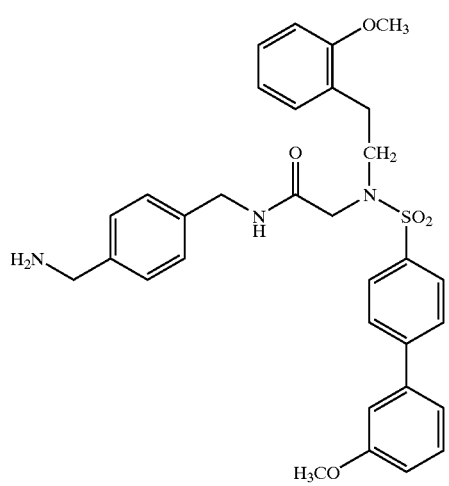
16
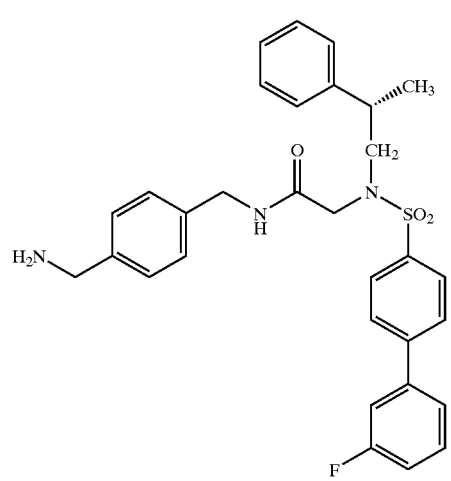
213
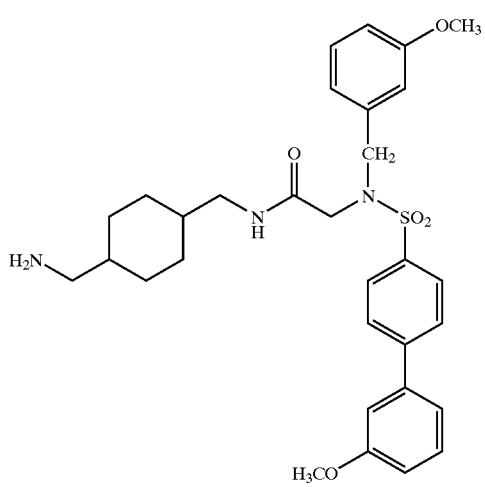
24
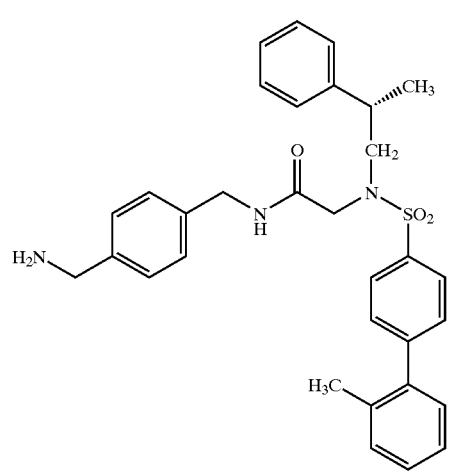
215

TABLE 2-continued
(Structure and Compound #)
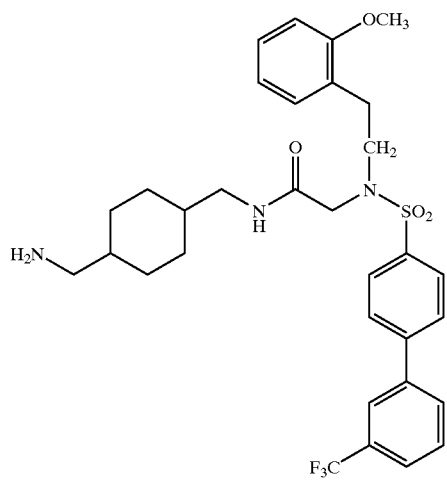
26
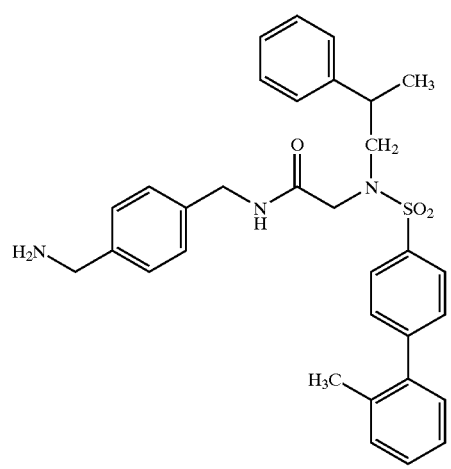
311
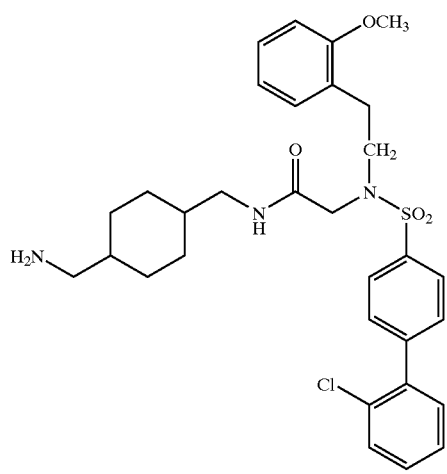
31
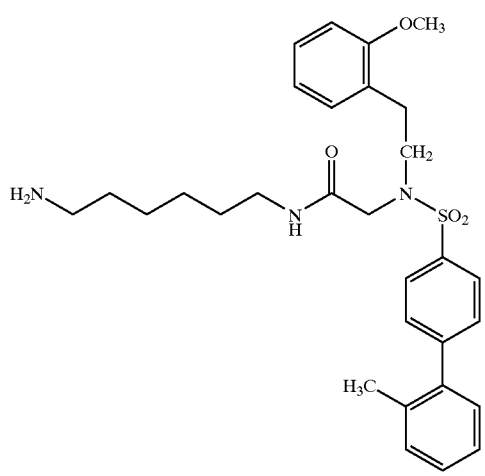
352
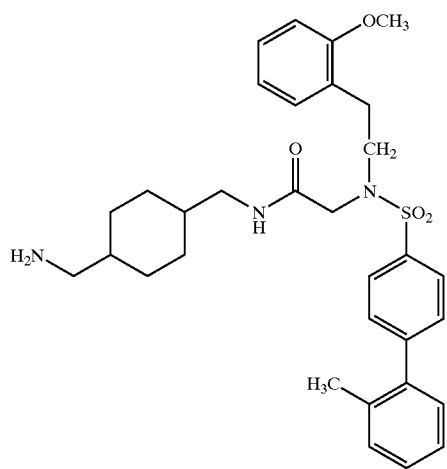
32
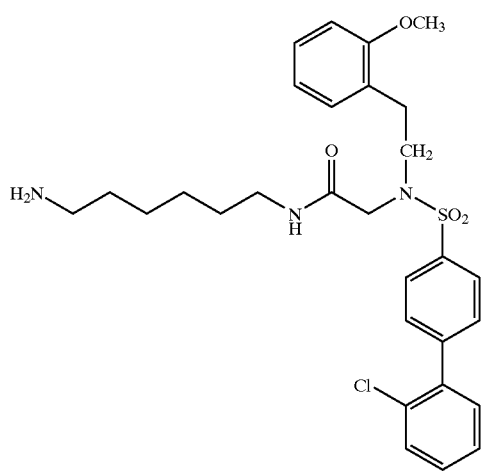
353

TABLE 2-continued
(Structure and Compound #)
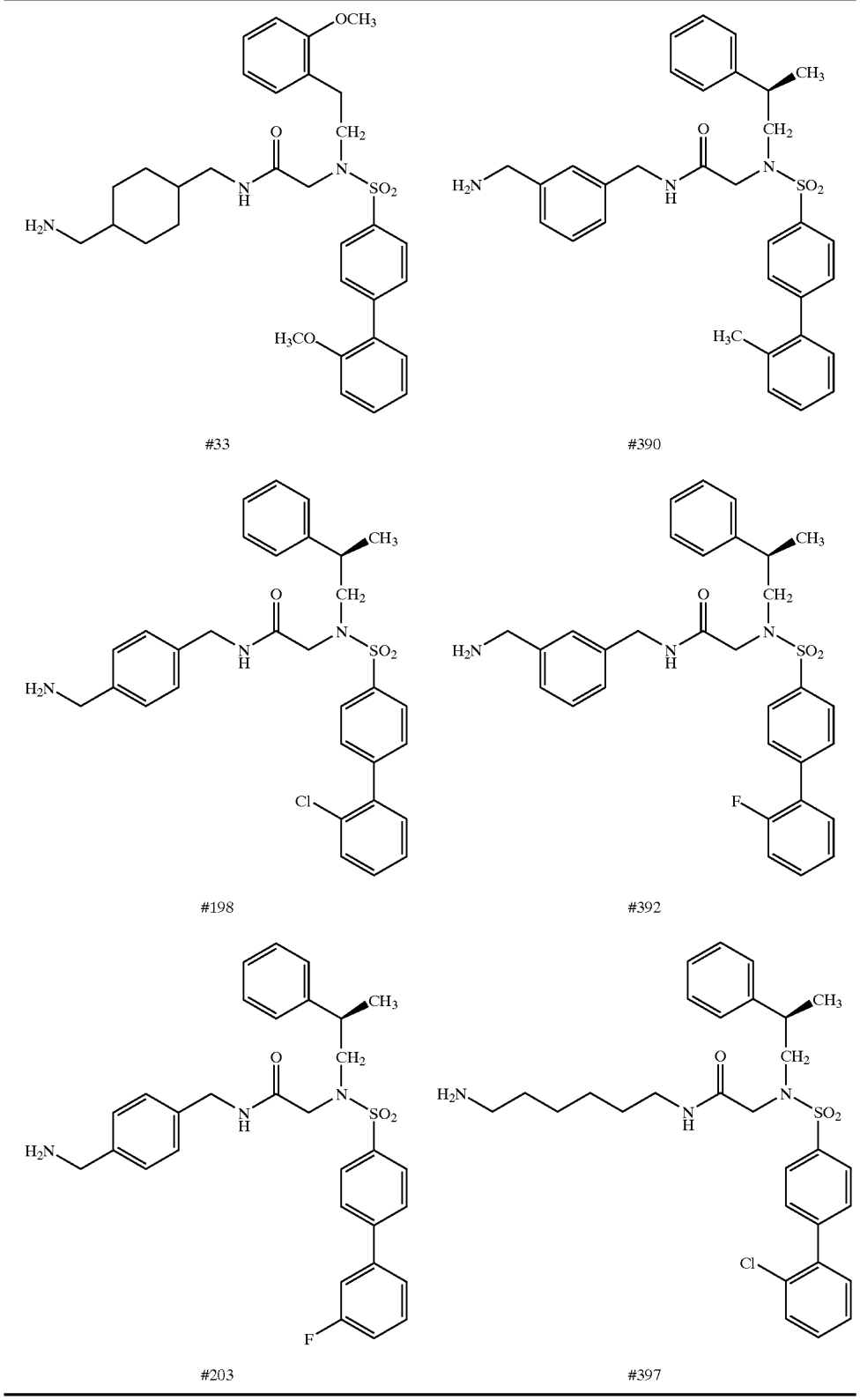
33
390
198
392
203
397
and stereoisomers and pharmaceutically acceptable salts or esters thereof.

For the compounds listed in Table 3 below, as well as all compounds listed in Table 1 and 2 above, structures were confirmed via molecular weight determination using an electro-spray mass spectrometer in positive mode and via HPLC retention time on a reversed phase column.

TABLE 3

| Cmpd # | Meas MW MH+ | HPLC RT (min) |
|---|---|---|
| 39 | 460.47 | |
| 40 | 500.13, 502.10 | |
| 41 | 528.56, 530.27 | |
| 42 | 528.48, 530.28 | |
| 43 | 494.43, 496.16 | |
| 44 | 528.05, 530.16 | |
| 45 | 510.29 | |
| 46 | 494.32, 496.16 | |
| 47 | 494.23, 496.16 | |
| 48 | 534.05, 536.12 | |
| 49 | 528.07, 530.11 | |
| 50 | 528.07, 530.12 | |
| 51 | 528.07, 530.13 | |
| 52 | 528.07, 530.14 | |
| 53 | 528.07, 530.15 | |
| 54 | 474.62, 476.30 | |
| 55 | 474.62, 476.31 | |
| 56 | 490.62, 492.37 | |
| 57 | 510.57, 512.37 | |
| 58 | 478.66, 480.23 | |
| 59 | 520.45, 522.37 | |
| 60 | 520.56, 522.33 | |
| 61 | 505.3 | |
| 62 | 505.3 | |
| 63 | 505.3 | |
| 64 | 586.45 | |
| 65 | 516.7 | |
| 66 | 535.41 | |
| 67 | 504.67, 506.39 | |
| 68 | 573.51 | |
| 69 | 478.68, 480.35 | |
| 70 | 478.68, 480.36 | |
| 71 | | 3.325 |
| 72 | | 3.348 |
| 73 | | 3.315 |
| 74 | 52.45, 524.28 | |
| 75 | 514.34, 516.29 | |
| 76 | 538.47, 540.32 | |
| 77 | 526.58, 528.32 | |
| 78 | 568.03 | |
| 79 | 538.42, 540.36 | |
| 80 | 522.57, 524.34 | |
| 81 | 558.56, 560.31 | |
| 82 | 542.26, 544.13 | |
| 83 | 509.14 | |
| 84 | 514.16 | |
| 85 | 565.5, 567.30 | |
| 86 | 508.47, 510.29 | |
| 87 | 542.19, 544.07 | |
| 88 | 527.44, 530.22 | |
| 89 | | 3.206 |
| 90 | 533.40, 535.30 | |
| 91 | 509.14 | |
| 92 | 538.46, 540.34 | |
| 93 | 523.16 | |
| 94 | 536.54 | |
| 95 | 528.31, 530.28 | |
| 96 | 552.48, 55434 | |
| 97 | 540.44, 542.34 | |
| 98 | 582.07 | |
| 99 | 552.67, 554.32 | |
| 100 | 536.53, 538.37 | |
| 101 | 572.43, 574.23 | |
| 102 | 556.25, 558.04 | |
| 103 | 523.16 | |
| 104 | 528.3 | |
| 105 | | 3.158 |
| 106 | 522.42 | |
| 107 | 556.20, 558.01 | |

TABLE 3-continued

| Cmpd # | Meas MW MH+ | HPLC RT (min) |
|---|---|---|
| 108 | 541.34, 543.37 | |
| 109 | | 3.293 |
| 110 | 547.22 | |
| 111 | 523.2 | |
| 112 | 552.37 | |
| 113 | 537.18 | |
| 114 | 508.0, 510.0 | |
| 115 | 536.1 | |
| 116 | 536.1 | |
| 117 | 502.1, 504.1 | |
| 118 | 536.0, 538.0 | |
| 119 | 518.1 | |
| 120 | 502.1, 504.1 | |
| 121 | 528.1 | |
| 122 | 536.0, 538.0 | |
| 123 | 536.0, 538.1 | |
| 124 | 536.0, 538.2 | |
| 125 | 536.0, 538.3 | |
| 126 | 541.9, 543.9 | |
| 127 | 482.2 | |
| 128 | 498.2 | |
| 129 | 518.1 | |
| 130 | 486.2 | |
| 131 | 486.2 | |
| 132 | 486.2 | |
| 133 | 528.1 | |
| 134 | 513.1 | |
| 135 | 513.1 | |
| 136 | 513.1 | |
| 137 | 594 | |
| 138 | 524.2 | |
| 139 | 543.1 | |
| 140 | 512.2 | |
| 141 | | 2.946 |
| 142 | 581 | |
| 143 | 536.1 | |
| 144 | 552 | |
| 145 | 551 | |
| 146 | 598.1 | |
| 147 | 474.1 | |
| 148 | 482.2 | |
| 149 | 502.1, 504.1 | |
| 150 | 468.1 | |
| 151 | 508.2 | |
| 152 | 500.1 | |
| 153 | 524.1 | |
| 154 | 512.1 | |
| 155 | 554.1 | |
| 156 | 524.1 | |
| 157 | 508.2 | |
| 158 | 544.1 | |
| 159 | 528.1, 530.1 | |
| 160 | 495.2 | |
| 161 | 500.1 | |
| 162 | 551.1 | |
| 163 | 494.2 | |
| 164 | 528.1 | |
| 165 | 513.1 | |
| 166 | 528.1, 530.0 | |
| 167 | 519.1 | |
| 168 | 495.2 | |
| 169 | 524.1 | |
| 170 | 509.1 | |
| 171 | 512.1 | |
| 172 | 512.1 | |
| 173 | 538.1 | |
| 174 | 494.2 | |
| 175 | 486.1 | |
| 176 | 510.1 | |
| 177 | 498.1 | |
| 178 | 540.1 | |
| 179 | 510.1 | |
| 180 | 494.2 | |
| 181 | 530.1 | |
| 182 | 514.1, 516.2 | |
| 183 | 481.1 | |

TABLE 3-continued

| Cmpd # | Meas MW MH⁺ | HPLC RT (min) |
|---|---|---|
| 184 | 486.1 | |
| 185 | 537.1 | |
| 186 | 480.2 | |
| 187 | 514.1, 516.0 | |
| 188 | 499.1 | |
| 189 | 514.1, 516.0 | |
| 190 | 505.1 | |
| 191 | 481.1 | |
| 192 | 510.1 | |
| 193 | 495.2 | |
| 194 | 498.1 | |
| 195 | 498.1 | |
| 196 | 524.1 | |
| 197 | 528.2 | |
| 198 | 562.1, 564.0 562.4, 564.4 | |
| 199 | 562.1, 564.1 | |
| 200 | 558.1 | |
| 201 | 558.1 | |
| 202 | 558.1 | |
| 203 | 546.1 | |
| 204 | 546.1 | |
| 205 | 542.1 | |
| 206 | 542.1 | |
| 207 | 528.1 | |
| 208 | 562.1, 564.0 | |
| 209 | 562.1, 564.1 | |
| 210 | 558.1 | |
| 211 | 558.1 | |
| 212 | 558.1 | |
| 213 | 546.1 | |
| 214 | 546.1 | |
| 215 | 542.1, 542.5 | |
| 216 | 542.1 | |
| 217 | | 3.418 |
| 218 | | 3.509 |
| 219 | | 3.403 |
| 220 | | 3.413 |
| 221 | | 3.450 |
| 222 | | 3.465 |
| 223 | | 3.539 |
| 224 | | 3.575 |
| 225 | 578.1, 580.1 | |
| 226 | 574.1 | |
| 227 | 559.1 | |
| 228 | 562.1 | |
| 229 | 562.1 | |
| 230 | 588.1 | |
| 231 | 578.1, 580.1 | |
| 232 | 544.1 | |
| 233 | 563.1 | |
| 234 | 569.1 | |
| 235 | 545.1 | |
| 236 | 634.3 | |
| 237 | 569.1 | |
| 238 | 604.2 | |
| 239 | 612.1, 614.1 | |
| 240 | 612.2 | |
| 241 | 612.2 | |
| 242 | 612.2 | |
| 243 | 558.1 | |
| 244 | 558.2 | |
| 245 | 550.1 | |
| 246 | 574.2 | |
| 247 | 562.1 | |
| 248 | 574.1 | |
| 249 | 558.2 | |
| 250 | 594.2 | |
| 251 | 578.1, 580.1 | |
| 252 | 545.2 | |
| 253 | 578.1, 580.1 | |
| 254 | 574.2 | |
| 255 | 559.2 | |
| 256 | 562.1 | |
| 257 | 562.1 | |
| 258 | 588.2 | |
| 259 | 578.1 | |
| 260 | 544.2 | |
| 261 | 563.2 | |
| 262 | 569.2 | |
| 263 | 545.2 | |
| 264 | 534.4 | |
| 265 | 569.1 | |
| 266 | 604.3, 605.3 | |
| 267 | 612.3 | |
| 268 | 612.3 | |
| 269 | 612.3 | |
| 270 | 558.2 | |
| 271 | 554.0, 556.1 | |
| 272 | 564.1 | |
| 273 | 556.1 | |
| 274 | 580.2 | |
| 275 | 568.1 | |
| 276 | 580.2 | |
| 277 | 564.1 | |
| 278 | 600.2 | |
| 279 | 584.1, 586.1 | |
| 280 | 551.1 | |
| 281 | 584.1, 586.1 | |
| 282 | 580.2 | |
| 283 | 565.1 | |
| 284 | 568.1 | |
| 285 | 568.1 | |
| 286 | 594.2 | |
| 287 | 584.1, 586.1 | |
| 288 | 550.1 | |
| 289 | 569.1 | |
| 290 | 575.1 | |
| 291 | 551.1 | |
| 292 | 640.4 | |
| 293 | 575.1 | |
| 294 | | 3.315 |
| 295 | 610.2 | |
| 296 | | 4.021 |
| 297 | 618.3 | |
| 298 | 618.2 | |
| 299 | 618.2 | |
| 300 | 564.1 | |
| 301 | 546 | |
| 302 | 564 | |
| 303 | 595.9, 597.9 | |
| 304 | 596 | |
| 305 | 570 | |
| 306 | 546 | |
| 307 | 564 | |
| 308 | 595.9, 597.9 | |
| 309 | 596 | |
| 310 | 570 | |
| 311 | 542 | |
| 312 | 561.9, 563.9 | |
| 313 | 546 | |
| 314 | 576.0, 578.0 | |
| 315 | 595.9, 597.9 | |
| 316 | 579.9, 581.9 | |
| 317 | 588.0, 590.0 | |
| 318 | 608.0, 610.0 | |
| 319 | 592.0, 594.0 | |
| 320 | 540 | |
| 321 | 559.9, 561.9 | |
| 322 | 544 | |
| 323 | 528 | |
| 324 | 548.0, 549.9 | |
| 325 | 532 | |
| 336 | 564.1 | |
| 337 | 584.1, 586.1 | |
| 338 | 580.1 | |
| 339 | 618.1, 620.1 | |
| 340 | 550.1 | |
| 341 | 570.0, 572.0 | |
| 342 | 566.1 | |
| 343 | 604.1, 606.1 | |
| 344 | 558.1 | |

TABLE 3-continued

| Cmpd # | Meas MW MH⁺ | HPLC RT (min) |
|---|---|---|
| 345 | 578.0, 580.0 | |
| 346 | 574.1 | |
| 347 | 612.1, 614.1 | |
| 348 | 544.1 | |
| 349 | 564.0, 566.0 | |
| 350 | 560.1 | |
| 351 | 598.0, 600.0 | |
| 352 | 538.2, 538.2 | |
| 353 | 558.1, 560.1 | |
| | 558.1, 560.1 | |
| 354 | 554.1 | |
| 355 | 592.0, 594.0 | |
| 356 | 524.2 | |
| 357 | 544.1, 546.1 | |
| 358 | 540.1 | |
| 359 | 578.0, 580.0 | |
| 366 | 574.2 | |
| 367 | 594.1, 596.1 | |
| 368 | 578.1 | |
| 369 | 574.1 | |
| 370 | 594.1, 596.1 | |
| 371 | 578.1 | |
| 372 | 548.2 | |
| 373 | 568.1, 570.1 | |
| | 568.1, 570.1 | |
| 374 | 552.1 | |
| 375 | 548.2 | |
| 376 | 568.1, 570.0 | |
| 377 | 552.1 | |
| 378 | 508.2 | |
| 379 | 526.1 | |
| 380 | 512.1 | |
| 381 | 508.2 | |
| 382 | 528.1, 530.1 | |
| 383 | 512.1 | |
| 384 | 548.2 | |
| 385 | 568.1, 570.0 | |
| 386 | 552.1 | |
| 387 | 548.1 | |
| 388 | 568 | |
| 389 | 552.1 | |
| 390 | 542.1, 542.1 | |
| 391 | 564 | |
| 392 | 546, 546.0 | |
| 393 | 542.1 | |
| 394 | 562.0, 564.0 | |
| 395 | 546 | |
| 396 | 522.2, 522.2 | |
| 397 | 542.1, 544.1 | |
| | 542.1, 544.1 | |
| 398 | 526.1, 526.1 | |
| 399 | 522.2 | |
| 400 | 542.1, 544.1 | |
| 401 | 526.1 | |
| 402 | 528.1, 530.2. | |
| 412 | 528.2 | |
| 413 | 573.1 | |
| 414 | 546.1 | |
| 415 | 542.2 | |
| 416 | 596.1 | |
| 417 | 596.1 | |
| 418 | 562.1 | |
| 419 | 558.1 | |
| 420 | 596.1 | |
| 421 | 558.1 | |
| 422 | 612.1 | |
| 423 | 546.1 | |
| 424 | 578.1 | |
| 425 | 580 | |
| 426 | 606 | |
| 427 | 562 | |
| 428 | 596 | |
| 429 | 596 | |
| 430 | 664 | |
| 431 | 508.1 | |
| 432 | 568.1 | |
| 433 | 663 | |
| 434 | 553.1 | |
| 435 | 553.1 | |
| 436 | 572 | |
| 437 | 655.1 | |
| 438 | 547.1 | |
| 439 | 586 | |
| 440 | 529.1 | |
| 441 | 618.1 | |
| 442 | 650 | |
| 443 | 532 | |
| 444 | 548.1 | |
| 445 | 452.1 | |
| 446 | 634.1 | |
| 447 | 666 | |
| 448 | 634.1 | |
| 449 | 584 | |
| 450 | 588.1 | |
| 451 | 546.1 | |
| 452 | 578.1 | |
| 453 | 558.1 | |
| 454 | 580 | |
| 455 | 573 | |
| 456 | 604.1 | |
| 457 | 657.1 | |
| 458 | 657.1 | |
| 459 | 546.1 | |
| 460 | 588.1 | |
| 461 | 685.2 | |
| 462 | 574 | |
| 463 | 570.1 | |
| 464 | 542.2 | |
| 465 | 542.1 | |
| 466 | 539.2 | |
| 467 | 543.2 | |
| 468 | 585.1 | |
| 469 | 530.31, 532.31 | |
| 470 | 530.31, 532.32 | |
| 471 | 590.54, 592.54 | |
| 472 | 618.59, 620.57 | |
| 473 | 604.52, 606.54 | |
| 474 | 570.59 | |
| 475 | 598.64 | |
| 476 | 584.57 | |
| 477 | 526.5, 528.5 | |
| 478 | 506.6 | |
| 479 | 510.6 | |
| 480 | 606.5, 608.5 | |
| 481 | 614.5, 616.5 | |
| 483 | 578.5, 580.4 | |
| 484 | 608.5, 610.5 | |
| 485 | 608.5, 610.5 | |
| 486 | 552.5, 554.5 | |
| 487 | 686.5, 688.5 | |
| 488 | 582.4, 584.4 | |
| 489 | 582.4, 584.4 | |
| 490 | 616.5, 618.5 | |
| 491 | 616.5, 618.4 | |
| 492 | 616.5, 618.5 | |
| 493 | 622.6, 624.6 | |
| 494 | 608.5, 610.5 | |
| 495 | 578.4, 580.4 | |
| 496 | 718.6, 720.6 | |
| 497 | 636.7 | |
| 498 | 616.7 | |
| 499 | 620.9 | |
| 500 | 636.7 | |
| 501 | 602.6, 604.5 | |
| 502 | 558.5, 560.5 | |
| 503 | 588.5, 590.5 | |
| 504 | 666.6, 668.6 | |
| 505 | 562.4, 564.4 | |
| 506 | 562.4, 564.4 | |
| 507 | 596.4, 598.4 | |
| 508 | 596.5, 598.5 | |
| 509 | 588.5, 590.5 | |

TABLE 3-continued

| Cmpd # | Meas MW MH+ | HPLC RT (min) |
|---|---|---|
| 510 | 558.5, 560.5 | |
| 511 | 588.5, 560.5 | |
| 512 | 532.5, 534.5 | |
| 513 | 698.7, 700.7 | |
| 514 | 546.5. 548.5 | |
| 515 | 596.5, 598.5 | |
| 521 | 576.5, 578.5 | |
| 522 | 576.5, 578.5 | |
| 523 | 576.5, 578.6 | |
| 524 | 576.5, 578.7 | |
| 525 | 576.5, 578.8 | |
| 526 | 576.5, 578.9 | |
| 527 | 592.9, 594.9 | |
| 528 | 563.0, 565.5 | |
| 529 | 590.9, 592.9 | |
| 530 | 604.9, 606.9 | |
| 531 | 640.9, 642.9 | |
| 532 | 576.0, 577.9 | |
| 533 | 578.0, 580.0 | |
| 534 | 592.0, 594.0 | |
| 535 | 560.0, 562.0 | |
| 536 | 616.0, 618.0 | |
| 537 | 587.9, 589.9 | |
| 538 | 576.0, 578.0 | |
| 539 | 560.0, 562.0 | |
| 540 | 623.9, 625.9 | |
| 541 | 562.0, 564.0 | |
| 542 | 566.0, 567.9 | |
| 543 | 591.9, 593.9 | |
| 544 | 549.0, 551.0 | |
| 545 | 554.0, 555.9 | |
| 546 | 555.0, 557.0 | |
| 547 | 562.0, 564.0 | |
| 548 | 591.9, 593.9 | |
| 549 | 615.8, 617.8 | |
| 550 | 582.6 | |
| 551 | 482.6 | |
| 552 | 520.5 | |
| 553 | 494.6 | |
| 554 | 494.6 | |
| 555 | 508.6 | |
| 556 | 522.6 | |
| 557 | 482.6 | |
| 558 | 482.6 | |
| 559 | 520.5 | |
| 560 | 494.5 | |
| 561 | 494.6 | |
| 562 | 508.6 | |
| 563 | 522.6 | |
| 564 | 482.5 | |
| 572 | 558.4, 560.0 | |
| 573 | 572.0, 574.0 | |
| 574 | 540.5, 542.1 | |
| 575 | 596.4, 598.0 | |
| 576 | 569.2, 571.0 | |
| 577 | 557.0, 559.1 | |
| 578 | 540.5, 542.1 | |
| 579 | 604.3 | |
| 580 | 542.4, 544.1 | |
| 581 | 547.1, 549.0 | |
| 582 | 572.0, 574.0 | |
| 583 | 529.0, 531.0 | |
| 584 | 534.0, 536.0 | |
| 585 | 535.1, 537.1 | |
| 586 | 542.5, 544.1 | |
| 587 | 572.0, 574.0 | |
| 588 | 596.0, 597.9 | |
| 589 | 596.3, 597.9 | |
| 590 | 507.6 | |
| 591 | 507.6 | |

The salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The pharmaceutically acceptable esters of the novel compounds of the present invention include such as would be readily apparent to a medicinal chemist, and include, for example, those described in detail in U.S. Pat. No. 4,309,43, Column 9, line 61 ot Column 12, line 51, which is incorporated herein by reference. Included within such pharmaceutically acceptable esters are those hydrolyzed under physiological conditions, such as pivaloyloxymethyl, acetoxymethyl, phthalidyl, indanyl and methoxymethyl, and those described I detail in U.S. Pat. No. 4,479,947, which is incorporated herein by reference.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Abbreviations used in the specification, particularly the Schemes and Examples, are as follows:

TABLE 4

| Abbreviation | Definition |
| --- | --- |
| BOC = | Butoxycarbonyl |
| Cmpd # = | Compound Number |
| DCE = | Dichloroethane |
| DCM = | Dichloromethane |
| DIEA = | Diisopropylethylamine |
| DMAC = | Dimethylacetamide |
| DMAP = | 4-Dimethylaminopyridine |
| DMF = | Dimethylformamide |
| DMSO = | Dimethylsulfoxide |
| EDTA = | Ethylenediamine-N,N,N",N"-tetraacetic acid |
| Fmoc = | 9-Fluorenyl methoxycarbonyl |
| h-FSHR = | human Follicle Stimulating Hormone Receptor |
| FMPB = | 4-(4-Formyl-3-methoxyphenyoxy)butyryl |
| HATU = | 2-(1H-Benzotriazol-1-yl)-1,1,3,3-tetramethyluronium hexafluorophosphate |
| HPLC RT = | High Pressure Liquid Chromatography Retention Time |
| Mol. Wt. = | Measured Molecular Weight |
| PBF = | 2,2,4,6,7-Pentamethyldihydrobenzofuran-5-sulfonyl |
| Stereo = | Optical Configuration of Stereogenic Center |
| TMOF = | Trimethylorthoformate |

The substituted aminoalkylamide derivatives of this invention are capable of inhibiting follicle stimulating hormone (FSH) to achieve the desired pharmacological effect. With an effective amount of the substituted aminoalkylamide derivative compounds dispersed in a pharmaceutical composition as an active ingredient, the pharmaceutical composition is introduced as a unit dose into an afflicted mammal.

The term "unit dosage" and its grammatical equivalent is used herein to refer to physically discrete units suitable as unitary dosages for human patients and other warm blooded mammals, each unit containing a predetermined effective, pharmacologic amount of the active ingredient calculated to produce the desired pharmacological effect in association with the required physiologically tolerable carrier, e.g., a diluent or a vehicle. The specifications for the novel unit dosage forms suitable for use herein are dictated by and are directly dependent on (a) the unique characteristics of the active ingredient, and (b) the limitations inherent in the art of compounding such an active ingredient for therapeutic use in humans and other mammals. Examples of suitable unit dosage form in accord with this invention are tablets, capsules, pills, powder packets, granules, wafers, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation and the like. The active ingredient is referred to herein as being dispersed in the carrier. The dispersion form can be a simple admixture, a non-settling dispersion as in the case of certain emulsions, or as an ultimate dispersion, a true solution.

The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligrams per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans. When the compounds are employed to treat FSH receptor mediated diseases or disorders the dosage range can be about 0.01 to about 200 mg/kg. The preferred dosage range is from about 0.5 to about 100 mg/kg.

Physiologically tolerable carriers are well known in the art. Carriers may be divided into liquid and solid carriers.

Exemplary of liquid carriers are aqueous solutions that contain no materials in addition to the substituted aminoalkylamide derivative compound, or contain a buffer such as sodium phosphate ay a physiological pH value, saline and the like. Liquid compositions can also contain liquid phases in addition to and to the exclusion of water. Exemplary of such additional liquid phases are glycerin and vegetable oils such as cottonseed oil.

Exemplary solid carriers (diluents) include those materials usually used in the manufacture of pills or tablets, and include corn starch, lactose, dicalcium phosphate, thickeners, such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET (aspartame) by G. D. Searle Co.

The pharmaceutical composition can be administered orally, topically or by injection, by means well known in the art. In preferred practice, the composition is administered orally as a tablet, capsule or aqueous dispersion. The pharmaceutical composition is maintained within the mammal until the substituted aminoalkylamide derivative compound is cleared from the mammal's body by natural means such as excretion or metabolism.

Compositions for injection may be prepared in unit dosage form in ampules or in multidose containers. The compositions may take such forms as suspensions, solutions, or emulsions in oily or aqueous vehicles, and may contain formulatory agents. Alternatively, the active ingredient may be in a powder form for reconstitution, at the time of delivery, with a suitable vehicle, such as sterile water. Topical formulations may be formulated in hydrophobic or hydrophilic bases as ointments, creams, lotions, paints, or powders.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Inasmuch as a pharmaceutical composition can be administered 3 to 4 times daily (per 24 hour period), the method of treating a disorder of condition mediated by FSH can include administering the pharmaceutical composition a plurality of times into the treated mammal over a time period of weeks, months and years.

Disorders or conditions mediated by the FSH receptor include uterine fibroids, endometriosis, polycystic ovarian disease, dysfunctional uterine bleeding, breast cancer and ovarian cancer; depletion of oocytes (a common side effect of chemotherapy or similar treatment); spermatocyte depletion; or for female and male contraception.

The following examples are set forth to aid in the understanding of the invention, and are not intended and should not be construed to limit in any way the invention set forth in the claims which follow thereafter.

EXAMPLE 1

COMPOUND #198

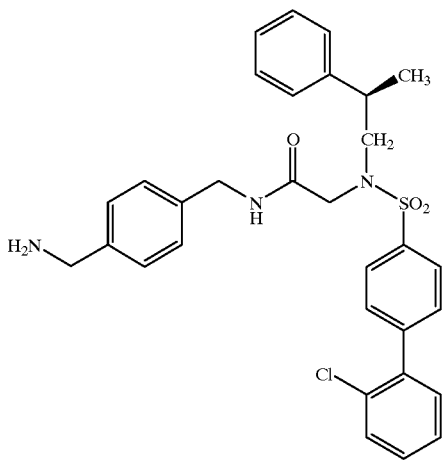

A. Preparation of Amino Carbamate Resin

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenyl-sulfonamide resin (from D) was split into 10 portions, each containing 0.133 millimole of resin. To one portion was added 2-chlorobenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 301–310 were prepared according to the above procedure with appropriate selection and substitution of suitably substituted benzeneboronic acid in Step E.

Compounds 311–319 were similarly prepared according to the procedure above with appropriate selection and substitution of a racemic mixture of suitably substituted phenethylamine in Step C and appropriate selection and substitution of suitably substituted benzeneboronic acid in Step E.

Compounds 412 through 468 may similarly be prepared according to the procedure described above, with appropriate selected and substitution of a suitably substituted boronic acid in Step E.

Compounds 469–470 were similarly prepared according to the procedure above, with appropriate selection and substitution of reagents. Compound 469 was prepared from the product of Step D, Compound 470 was prepared by substituting (S)-β-methylphenethylamine for (R)-β-methylphenethylamine in Step C.

Compounds 483–496 were similarly prepared according to the procedure above, with appropriate selection and substitution of suitably substituted phenethylamines in step C. Compounds 527–549 were similarly prepared according to the procedure above with appropriate selection and substitution of suitably substituted phenethylamines in step C.

Compounds 522–526 were similarly prepared according to the procedure above, with appropriate selection and substitution of reagents.

EXAMPLE 2

COMPOUND #272

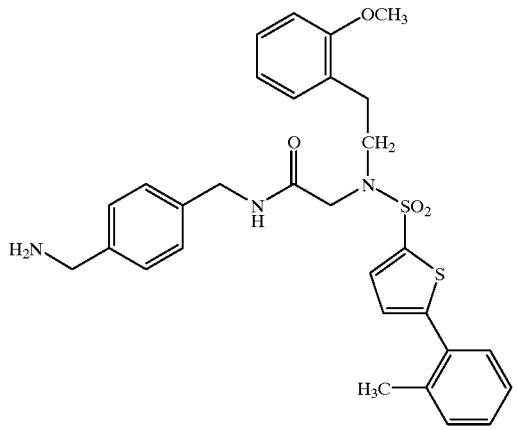

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-(2-methoxy)phenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of Sulfonamide Resin

The resin-bound secondary amine resin (from C) was swelled in DCM (200 mL). To the suspension was added pyridine (3.19 g) followed by 5-bromo-2-thiophenesulfonyl chloride (5.23 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 2-methylbenzeneboronic acid (0.089 g, 0.522 millimole). To the solution was then added palladium tetrakistriphenylphosphine (0.020 g, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 271, 273–300 were prepared according to the process above with appropriate selection and substitution of a suitably substituted boronic acid in Step E.

EXAMPLE 3

COMPOUND #205

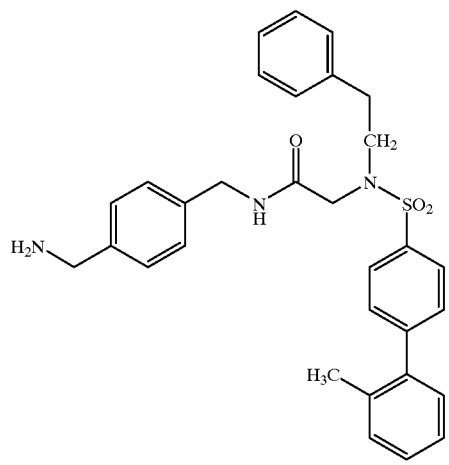

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine

The 2-bromoacetylated resin (from B) was swelled in DMSO (approximately 150 ml). To the suspension was added phenethylamine (6.045 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Bromophenylsulfonamide Resin

The resin-bound secondary amine (from C) was swelled in DCM (approximately 200 ml). To the suspension was added pyridine (3.19 g) followed by 4-bromophenylsulfonylchloride (5.1 g, 20 millimoles) and shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The resin-bound secondary amine (from D) was split into 10 portions, each containing 0.133 millimole of resin. To one portion was 2-methylbenzeneboronic acid (0.056 g, 0.399 millimoles). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 197, 199–204, 206–216 and 323–325 were prepared according to the above procedure, with appropriate selection and substitution of a suitably substituted benzeneboronic acid in Step E Compounds 412 through 468 may alternatively be prepared according to the procedure described in Example 3 above, with substitution of (R)-β-methylphenylethylamine in Step C and appropriate selected and substitution of a suitably substituted boronic acid in Step E.

EXAMPLE 4

COMPOUND #245

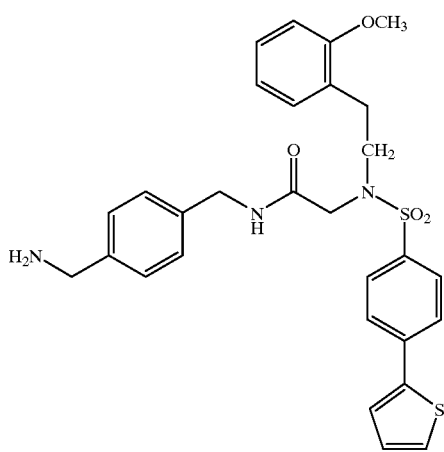

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine (Displacement of Bromide by 2-(2-methoxy)phenethylamine)

The 2-bromoacetylated resin (from B) was swelled in DMSO (approximately 150 ml). To the suspension was added 2-(2-methoxy)phenethylamine (6.045 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Bromophenylsulfonamide Resin

The resin-bound secondary amine (from C) was swelled in DCM (approximately 200 ml). To the suspension was added pyridine (3.19 g) followed by 3-bromophenylsulfonylchloride (5.1 g, 20 millimoles) and shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The 3-bromophenylsolfonamide resin (from D) was split into 30 portions, each containing 0.133 millimoles of resin. To one portion was added 2-thiopheneboronic acid (0.051 g, 0.399 millimoles). To the solution was then added palladium tetrakistriphenylphosphine (0.0154 g, 0.133 millimoles), DME (2.5 ml) and 2M sodium carbonate solution in water (0.830 ml). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 10–19, 145–146, 217, 219–244 and 246–270 were prepared according to the above procedure with appropriate selection and substitution of bromophenylsulfonyl chloride in step D and by appropriate selection and substitution of a suitably substituted boronic acid in step E.

EXAMPLE 5

COMPOUND #218

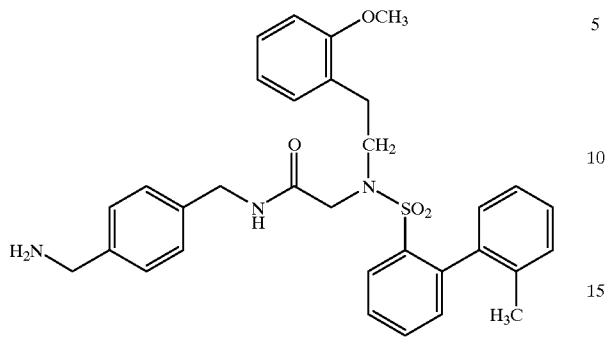

A. Preparation of Amino Carbamate Resin

Wang p-nitrophenylcarbonate resin (4.0 millimole) was swelled in DMF (200 mL). To the suspension was added 1,4-xylenediamine (5.45 g, 40.0 millimole) dissolved in DMF (75 mL). The mixture was shaken for 24 hours. The solvent was removed by filtration. The resin was washed with 3 portions of DMF, 3 portions of methanol, 3 portions of DCM/5% acetic acid, 3 portions of methanol, 3 portions of DCM/10% TEA, and 3 portions of methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxyphenethylamine (6.05 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 2-Bromophenylsulfonamide Resin

The resin-bound secondary amine resin (from C) was swelled in DCM (200 mL). To the suspension was added pyridine (3.19 g) followed by 2-bromophenylsulfonyl chloride (5.1 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 2-bromophenylsulfonamide resin (from D) was split into 23 portions, each containing 0.174 millimole of resin. To one portion was added 2-methylbenzneboronic acid (0.071 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

EXAMPLE 6

COMPOUND #114

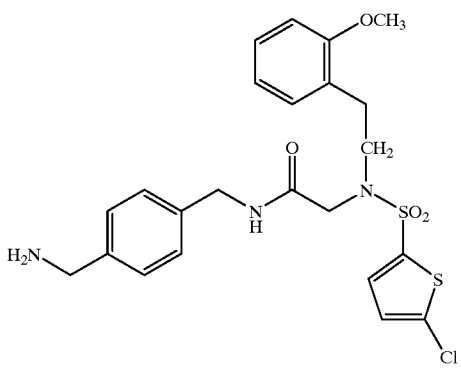

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic Acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine (Displacement of Bromide by 2-(2-methoxy)phenethylamine)

The 2-bromoacetylated resin (from B) was swelled in DMSO (approximately 150 ml). To the suspension was added 2-(2-methoxy)phenethylamine (6.045 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Sulfonamide Resin

The resin bound secondary amine (from C) was split into 36 portions each containing 0.111 millimole of resin. One portion was swelled in DCM (1.5 ml). To the suspension was added pyridine (0.089 g), followed by 5-chlorothiophene-2-sulfonyl chloride (0.121 g, 0.556 millimoles) and shaken overnight. The resin was filtered and washed with 3 portions of DCM, 3 portions of methanol, 3 portions of DCM, and 3 portions of methanol. The resin was dried in vacuo overnight.

E. Cleavage of the Resin Support

The product was cleaved from the resin using a cleaving cocktail solution of 90:10 TFA:water. The cleavage solution was evaporated. The product was purified by semi-preparative reversed phase HPLC on a 20×100 mm J'sphere H-80 YMC column using a gradient of 90:10:0.1 water:acetonitrile:TFA to 10:90:0.1 water:acetonitrile:TFA. The product wa lyophilized and analyzed by ES/MS and reversed phase HPLC.

Compounds 115–144 and 147–150 were prepared according the above procedure with appropriate selection and substitution of a suitably substituted sulfonyl chloride in Step D.

Compounds 550–564 were similarly prepared according to the procedure above with appropriate selection and substitution of suitably substituted phenethylamines in step C and appropriate selection and substitution of suitably substituted sulfonyl chlorides in step D.

EXAMPLE 7

COMPOUND #372

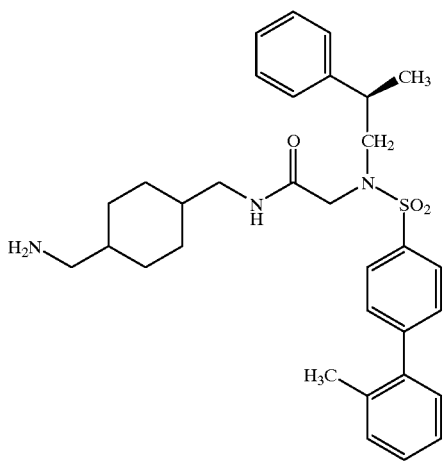

A. Preparation of Amino Carbamate Resin

Wang p-nitrophenylcarbonate resin (4.0 millimoles) was swelled in DMF (approximately 200 ml). To the suspension was added 1,4-cyclohexylmethylamine (5.69 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The N-(R)-β-methylphenthyl-4-bromophenylsulfonamide resin (from D) was split into 10 portions, each containing 0.133 millimole of resin. To one portion was 2-methylbenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 373–377 were prepared according to the procedure above with suitable selection and substitution of a suitably substituted benzeneboronic acid in Step E.

EXAMPLE 8

COMPOUND #29

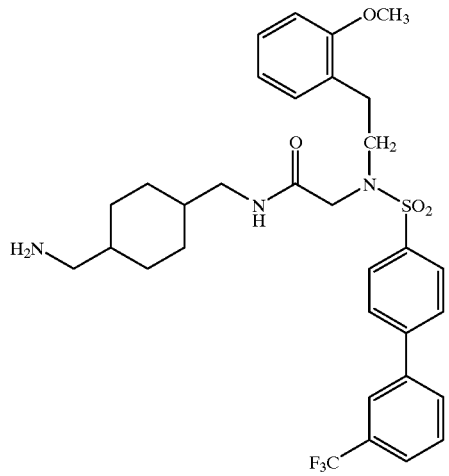

A. Preparation of Amino Carbamate Resin.

Wang p-nitrophenylcarbonate resin (4.0 millimoles) was swelled in DMF (approximately 200 ml). To the suspension was added 1,4-cyclohexylmethylamine (5.69 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine (Displacement of Bromide by 2-(2-methoxy)phenethylamine)

The 2-bromoacetylated resin (from B) was swelled in DMSO (approximately 150 ml). To the suspension was added 2-(2-methoxy)phenethylamine (6.045 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Bromophenylsulfonamide Resin

The resin-bound secondary amine (from C) was swelled in DCM (approximately 200 ml). To the suspension was added pyridine (3.19 g) followed by 4-bromophenylsulfonylchloride (5.1 g, 20 millimoles) and shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The 4-bromophenylsolfonamide resin (from D) was split into 30 portions, each containing 0.133 millimoles of resin. To one portion was added 3-trifluorobenzeneboronic acid (0.076 g, 0.399 millimoles). To the solution was then added palladium tetrakistriphenylphosphine (0.0154 g, 0.133 millimoles), DME (2.5 ml) and 2M sodium carbonate solution in water (0.830 ml). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 1–9, 20–28 and 30–38 were prepared according to the procedure above with appropriate selection and substitution of methoxybenzylamine or methoxyphenethylamine in Step C above, and appropriate selection and substitution of a suitably substituted benzeneboronic acid in Step E above.

EXAMPLE 9

COMPOUND #73

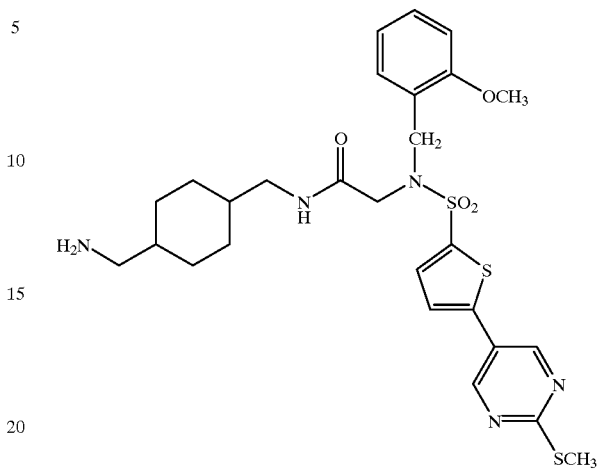

A. Preparation of Amino Carbamate Resin

Wang p-nitrophenylcarbonate resin (4.0 millimole) was swelled in DMF (200 mL). To the suspension was added 1,4-cyclohexylmethylamine (5.69 g, 40.0 millimole) dissolved in DMF (75 mL). The mixture was shaken for 24 hours. The solvent was removed by filtration. The resin was washed with 3 portions of DMF, 3 portions of methanol, 3 portions of DCM/5% acetic acid, 3 portions of methanol, 3 portions of DCM/10% TEA, and 3 portions of methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxybenzylamine (5.226 mL, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of Sulfonamide Resin

The resin-bound secondary amine resin (from C) was swelled in DCM (200 mL). To the suspension was added pyridine (3.19 g) followed by 5-bromo-2-thiophenesulfonyl chloride (5.23 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 5-(2-methylthiopyrimidyl)boronic acid (0.089 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 39–72 were similarly prepared according to the procedure above with appropriate selection and substitution of suitably substituted bromo-sulfonyl chloride in Step C above, and appropriate selection and substitution of a suitably substituted benzeneboronic acid in Step E above.

EXAMPLE 10

COMPOUND #94

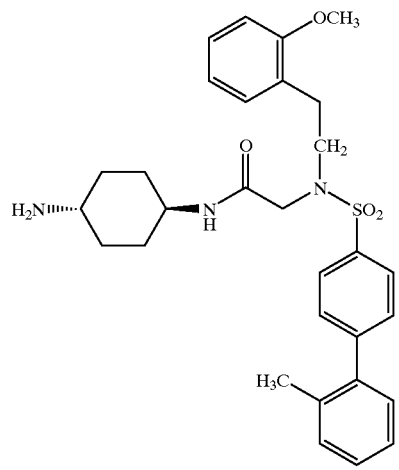

A. Preparation of Amino Carbamate Resin.

Wang p-nitrophenylcarbonate resin (4.0 millimoles) was swelled in DMF (approximately 200 ml). To the suspension was added trans-1,4-bisaminocyclohexane (4.57 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine (Displacement of Bromide by 2-(2-methoxy)phenethylamine)

The 2-bromoacetylated resin (from B) was swelled in DMSO (approximately 150 ml). To the suspension was added 2-(2-methoxy)phenethylamine (6.045 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Bromophenylsulfonamide Resin

The resin-bound secondary amine (from C) was swelled in DCM (approximately 200 ml). To the suspension was added pyridine (3.19 g) followed by 4-bromophenylsulfonylchloride (5.1 g, 20 millimoles) and shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The 4-bromophenylsolfonamide resin (from D) was split into 30 portions, each containing 0.133 millimoles of resin. To one portion was added 2-methylbenzeneboronic acid (0.054 g, 0.399 millimoles). To the solution was then added palladium tetrakistriphenylphosphine (0.0154 g, 0.133 millimoles), DME (2.5 ml) and 2M sodium carbonate solution in water (0.830 ml). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 74–93 and 95–113 were prepared according to the procedure above with appropriate selection and substitution 2-methoxyphenethylamine or 2-methoxybenzylamine in Step C above and appropriate selection and substitution of a suitably substituted boronic acid in Step E above.

EXAMPLE 11

COMPOUND #344

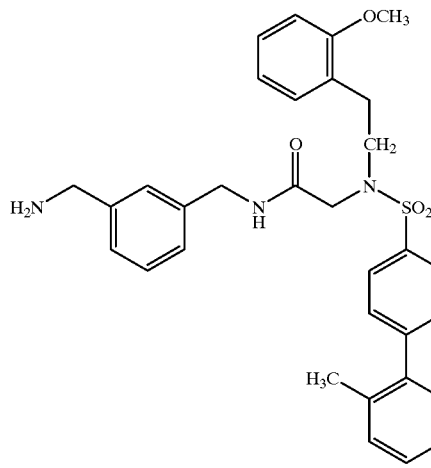

A. Preparation of Amino Carbamate Resin

Wang p-nitrophenylcarbonate resin (4.0 millimoles) was swelled in DMF (approximately 200 ml). To the suspension was added 1,3-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropyl-carbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxyphenethylamine (5.226 mL, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The resin-bound secondary amine resin (from C) was swelled in DCM (200 mL). To the suspension was added pyridine (3.19 g) followed by 4-bromophenylsulfonyl chloride (5.1 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 2-methylbenzeneboronic acid (0.071 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 345–351 were prepared according to the procedure above with appropriate selection and substitution of methoxybenzylamine or methoxyphenethylamine in Step C above and appropriate selection and substitution of a suitably substituted benzeneboronic acid in Step E above.

EXAMPLE 12

COMPOUND #392

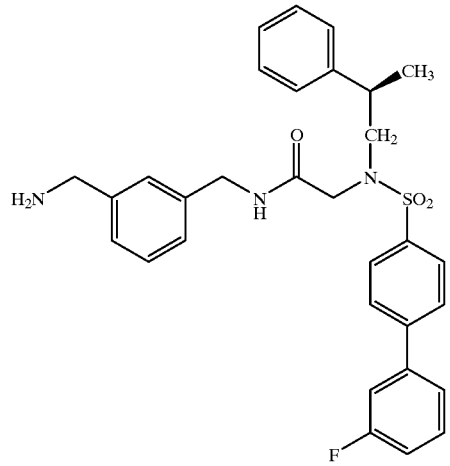

A. Preparation of Amino Carbamate Resin

Wang p-nitrophenylcarbonate resin (4.0 millimoles) was swelled in DMF (approximately 200 ml). To the suspension was added 1,3-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropyl-carbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenyl-sulfonamide resin (from D) was split into 10 portions, each containing 0.133 millimole of resin. To one portion was 3-fluorobenzeneboronic acid (0.056 g, 0.399 millimoles). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 390, 391, 393, 394 and 395 were prepared according to the procedure above with appropriate selection and substitution of a suitably substituted boronic acid in Step E.

EXAMPLE 13

COMPOUND #336

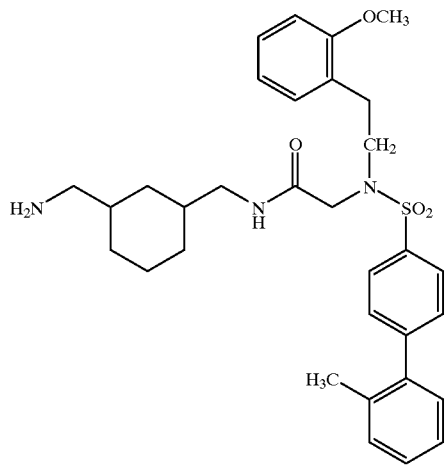

A. Preparation of Amino Carbamate Resin

Wang p-nitrophenylcarbonate resin (4.0 millimoles) was swelled in DMF (approximately 200 ml). To the suspension was added 1,3-bisaminomethylcyclohexane (5.69 g, 40 mmol) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxybenzylamine (5.226 mL, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The resin-bound secondary amine resin (from C) was swelled in DCM (200 mL). To the suspension was added pyridine (3.19 g) followed by 4-bromophenylsulfonyl chloride (5.1 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 2-methylbenzeneboronic acid (0.071 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 337–343 were similarly prepared according to the procedure above with suitable selection and substitution of a suitably substituted benzeneboronic acid in Step E.

EXAMPLE 14

COMPOUND #384

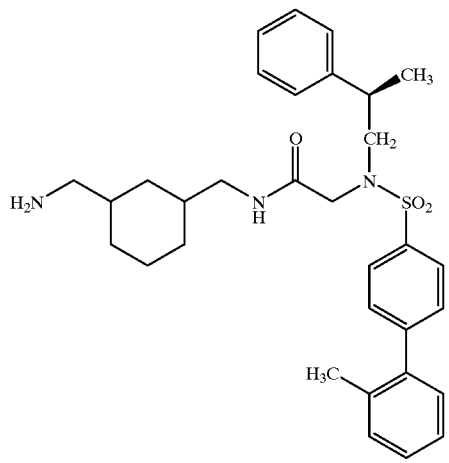

A. Preparation of Amino Carbamate Resin

Wang p-nitrophenylcarbonate resin (4.0 millimoles) was swelled in DMF (approximately 200 ml). To the suspension was added 1,3-bisaminomethylcyclohexane (5.69 g, 40 mmol) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

81

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The N-(R)-β-methylphenethyl-4-bromophenylsulfonamide resin (from D) was split into 10 portions, each containing 0.133 millimole of resin. To one portion was 2-methylbenzeneboronic acid (0.054 g, 0.399 mmol). To the solution was then added palladium tetrakistriphenylphosphine (0.0154, 0.0133 millimole), DME (2.5 mL) and 2M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 385–389 were similarly prepared according to the procedure above, by appropriate selection of optically pure methylphenethylamine in Step C above, and appropriate selection and substitution of a suitably substituted boronic acid in Step E.

82

EXAMPLE 15

COMPOUND #379

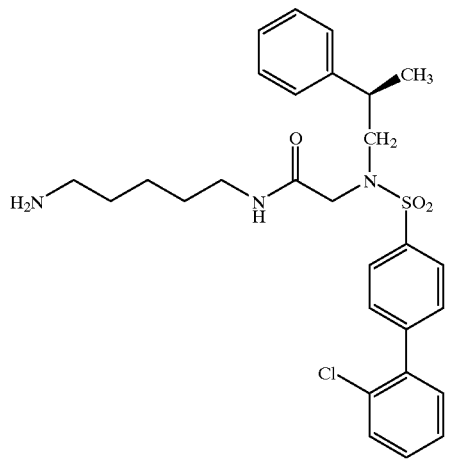

A. Preparation of Amino Carbamate Resin

Wang p-nitrophenylcarbonate resin (4.0 millimoles) was swelled in DMF (approximately 200 ml). To the suspension was added 15-pentanediamine (4.09 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenylsulfonamide resin (from D) was split into 10 portions, each containing 0.133 millimole of resin. To one portion was 2-chlorobenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 352, 378 and 380–383 were prepared according to the procedure above with appropriate selection and substitution of substituted benzeneboronic acid in Step E.

Compounds 353–359 and 396–401 were similarly prepared according to the procedure above with substitution of 1,6-n-hexyl diamine for the 1,5-n-pentyl diamine in step B and appropriate selection and substitution of suitably substituted benzeneboronic acid in Step E.

EXAMPLE 16

COMPOUND #151

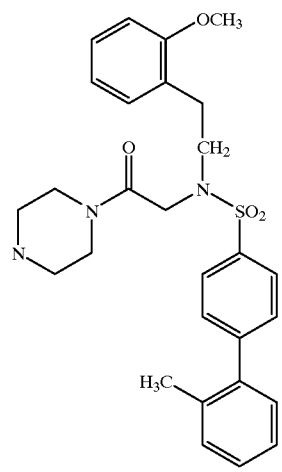

A. Preparation of Piperazino Carbamate Resin

Wang p-nitrophenylcarbonate resin (4.0 millimole) was swelled in DMF (200 mL). To the suspension was added piperazine (3.446 g, 40.0 millimole) dissolved in DMF (75 mL). The mixture was shaken for 24 hours. The solvent was removed by filtration. The resin was washed with 3 portions of DMF, 3 portions of methanol, 3 portions of DCM/5% acetic acid, 3 portions of methanol, 3 portions of DCM/10% TEA, and 3 portions of methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxybenzylamine (5.226 mL, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The resin-bound secondary amine resin (from C) was swelled in DCM (200 mL). To the suspension was added pyridine (3.19 g) followed by 4-bromophenylsulfonyl chloride (5.1 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 2-methylbenzeneboronic acid (0.071 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 152–173 were prepared according to the procedure above with appropriate selection and substitution of substituted boronic acid in step E.

EXAMPLE 17

COMPOUND #174

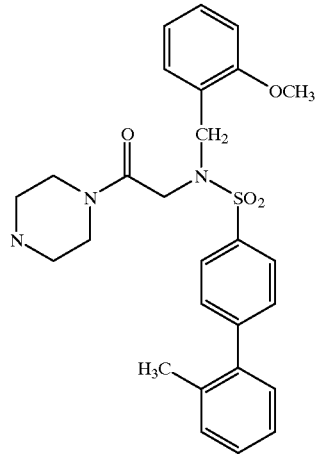

A. Preparation of Piperazino Carbamate Resin

Wang p-nitrophenylcarbonate resin (4.0 millimole) was swelled in DMF (200 mL). To the suspension was added piperazine (3.446 g, 40.0 millimole) dissolved in DMF (75 mL). The mixture was shaken for 24 hours. The solvent was removed by filtration. The resin was washed with 3 portions of DMF, 3 portions of methanol, 3 portions of DCM/5% acetic acid, 3 portions of methanol, 3 portions of DCM/10% TEA, and 3 portions of methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 2-methoxybenzylamine (5.226 mL, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The resin-bound secondary amine resin (from C) was swelled in DCM (200 mL). To the suspension was added pyridine (3.19 g) followed by 4-bromophenylsulfonyl chloride (5.1 g, 20.0 millimole) and shaken overnight. The resin was filtered and washed with 3 portions of DCM, 3 portions of methanol, 3 portions of DCM, and 3 portions of methanol. The resin was dried in vacuo overnight.

E. Preparation of Substituted Phenylsulfonamide Resin

The 4-bromophenylsulfonamide resin (from D) was split into 23 portions, each containing 0.174 millimole of resin. To one portion was added 2-methylbenzeneboronic acid (0.071 g, 0.522 millimole). To the solution was then added palladium tetrakistriphenylphosphine (0.020, 0.0174 millimole), DME (2.5 mL) and 2 M sodium carbonate solution in water (1.086 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 175–196 were prepared according to the procedure above with appropriate selection and substitution of substituted boronic acid in step E.

EXAMPLE 18

COMPOUND #367

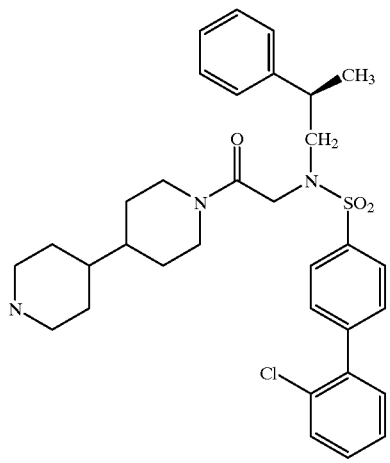

A. Preparation of Bipiperidino Resin

Wang p-nitrophenylcarbonate resin (4.0 millimoles) was swelled in DMF (approximately 200 ml). To the suspension was added 4,4'-bipiperdine (6.73 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenylsulfonamide resin (from D) was split into 10 portions, each containing 0.133 millimole of resin. To one portion was 2-chlorobenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 366 and 368–371 were prepared according to the procedure above with appropriate selection and substitution optically pure methylphenethylamine in Step C and appropriate selection and substitution of a suitably substituted benzeneboronic acid in Step E.

EXAMPLE 19

COMPOUND #320

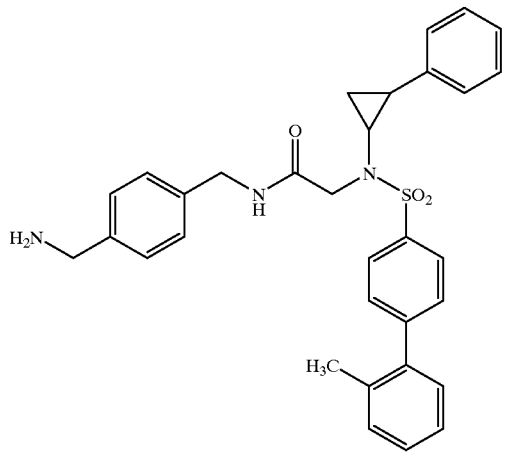

A. Preparation of Amino Carbamate Resin

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from B) was swelled in DMSO (150 mL). To the suspension was added 1-amino-2-phenyl-cyclopropane (5.33 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The 4-bromophenyl-sulfonamide resin (from D) was split into 10 portions, each containing 0.133 millimole of resin. To one portion was 2-methylbenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 321 and 322 were prepared according to the above procedure with appropriate selection and substitution of a suitably substituted benzeneboronic acid in Step E.

EXAMPLE 20

COMPOUND #405

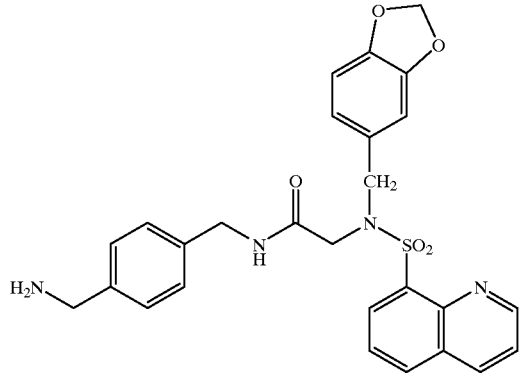

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine
(Displacement of Bromide by 2-methoxybenzylamine)

The 2-bromoacetylated resin (from B) was swelled in DMSO (approximately 150 ml). To the suspension was added 3,4-methylenedioxy-benzylamine (6.05 g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Sulfonamide Resin

The resin bound secondary amine (from C) was split into 36 portions each containing 0.111 millimole of resin. One portion was swelled in DCM (1.5 ml). To the suspension was added pyridine (0.089 g), followed by 8-quinolinylsulfonyl chloride (9.70 g, 0.556 millimoles) and shaken overnight. The resin was filtered and washed with 3 portions of DCM, 3 portions of methanol, 3 portions of DCM, and 3 portions of methanol. The resin was dried in vacuo overnight.

E. Cleavage of the Resin Support

The product was cleaved from the resin using a cleaving cocktail solution of 90:10 TFA:water. The cleavage solution was evaporated. The product was purified by semi-preparative reversed phase HPLC on a 20×100 mm J'sphere H-80 YMC column using a gradient of 90:10:0.1 water:acetonitrile:TFA to 10:90:0.1 water:acetonitrile:TFA. The product wa lyophilized and analyzed by ES/MS and reversed phase HPLC.

Compounds 403, 408, 409 and 411 were prepared according the above procedure with appropriate selection and substitution of a suitable diamine in Step A.

carbodiimide (2.53 g) and shaken overnight. The solvent was removed by filtration. The resin was then washed with 3 portions DMF, 3 portions methanol, and 3 portions DCM.

C. Preparation of the Secondary Amine
(Displacement of Bromide by 2-methoxybenzylamine)

The 2-bromoacetylated resin (from B) was swelled in DMSO (approximately 150 ml). To the suspension was added 2-methoxybenzylamine (5.226 mL g, 40 millimoles) and shaken overnight. The resin was filtered and washed with 3 portions of DMSO, 3 portions methanol, 3 portions DCM/5% acetic acid, 3 portions methanol, 3 portions DCM/10% TEA, and 3 portions methanol. The resin was dried in vacuo overnight.

D. Preparation of Sulfonamide Resin

The resin bound secondary amine (from C) was split into 36 portions each containing 0.111 millimole of resin. One portion was swelled in DCM (1.5 ml). To the suspension was added pyridine (0.089 g), followed by 2,3-dichlorobenzene sulfonyl chloride (0.137 g, 0.556 millimoles) and shaken overnight. The resin was filtered and washed with 3 portions of DCM, 3 portions of methanol, 3 portions of DCM, and 3 portions of methanol. The resin was dried in vacuo overnight.

E. Cleavage of the Resin Support

The product was cleaved from the resin using a cleaving cocktail solution of 90:10 TFA:water. The cleavage solution was evaporated. The product was purified by semi-preparative reversed phase HPLC on a 20×100 mm J'sphere H-80 YMC column using a gradient of 90:10:0.1 water:acetonitrile:TFA to 10:90:0.1 water:acetonitrile:TFA. The product wa lyophilized and analyzed by ES/MS and reversed phase HPLC.

Compounds 402, 406, 407 and 410 were prepared according the above procedure with appropriate selection and substitution of a suitable diamine in Step A.

EXAMPLE 21

COMPOUND #404

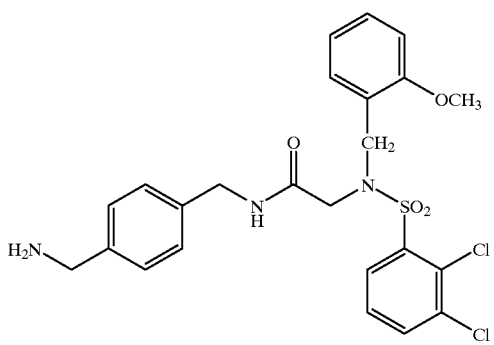

A. Preparation of Amino Carbamate Resin.

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid.

The carbamate resin (from A) was swelled in DMF (approximately 200 ml). To the suspension was added bromoacetic acid (2.77 g, 20 millimoles) and diisopropyl-

Example 22

COMPOUND #471

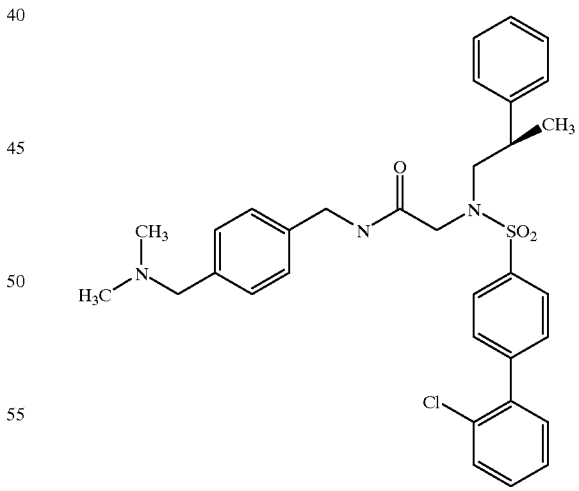

A. Dimethylation of Compound #198.

Compound #198, prepared as in Example 1 (100 mg, 0.178 millimoles) was dissolved in an equal mixture of TMOF and DCE (3.0 mL). To the solution were then added formaldehyde (16 mg, 0.534 millimoles), $NaBH_3CN$ (34 mg, 0.534 millimoles), and acetic acid (45 µL, 1.5%). The mixture was stirred for 16 h, and then the reaction was stopped by adding water. The crude product was extracted with chloroform, and the solvent removed under vacuum, to yield the product.

B. Purification of Product.

The crude product prepared in Step A was purified by semi-preparative reverse phase HPLC on a 20×100 mm J'sphere H-80 YMC column using a gradient of 90:10:0:0.1 water:acetonitrile:TFA to 10:90:0.1 water:acetonitrile:TFA. The product was lyophillized and analyzed by ES+/MS and reverse phase HPLC.

Compounds 472, 474, 475 were similarly prepared according to the procedure above with appropriate selection and substitution of reagents (Compound 472 was prepared by replacing the formaldehyde in Step A with acetaldehyde; Compound 474 was prepared by replacing compound 198 in Step A with compound 215; and Compound 475 by substituting compound 198 and formaldehde were in Step A with compound 215 and acetaldehyde, respectively).

EXAMPLE 23

COMPOUND #473

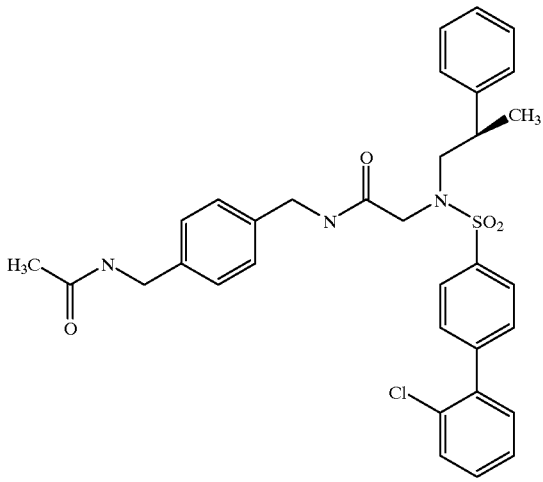

A. Acetylation of Compound #198.

Compound #198, prepared as in Example 1, (100 mg, 0.178 millimoles) was dissolved in chloroform (3.0 mL). To the solution were added acetyl chloride (19 45 µL, 0.267 millimoles), and TEA (37 45 µL, 0.267 millimoles), and the mixture stirred for 16. The reaction was then stopped by adding water. The crude product was washed twice by 10% NaHCO$_3$ aqueous solution.

B. Purification of Product.

The crude product from Step A was purified by semi-preparative reverse phase HPLC on a 20×100 mm J'sphere H-80 YMC column using a gradient of 90:10:0:0.1 water:acetonitrile:TFA to 10:90:0.1 water:acetonitrile:TFA. The product was lyophillized and analyzed by ES+/MS and reverse phase HPLC.

Compound 476 was similarly prepared according to the procedure above, with substitution of compound 198 in Step A with compound 215.

EXAMPLE 24

COMPOUND #497

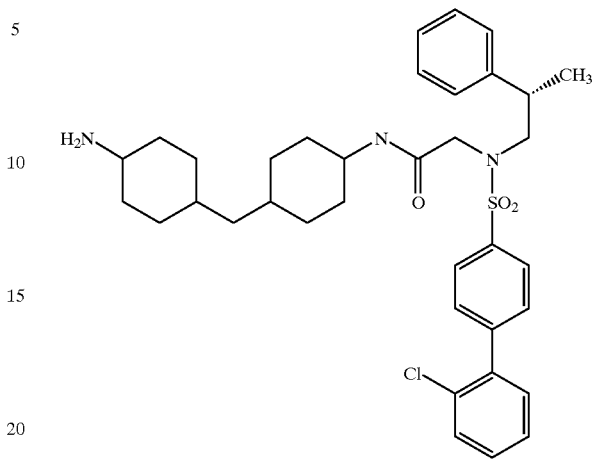

A. Preparation of Amino Carbamate Resin

Wang p-nitrophenylcarbonate resin (4.0 millimoles) was swelled in DMF (approximately 200 ml). To the suspension was added 4,4-methylenebis(cyclohexanamine) (8.41 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from Step A) was swelled in DMF (approximately 200 ml). To the suspension was added bromoacetic acid (2.77 g, 20 millimoles) and diisopropylcarbodiimide (2.53 g) and the mixture shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from Step B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from Step C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenylsulfonamide resin (from Step D) was split into 10 portions, each containing 0.133 millimole of resin. To one portion was added 2-chlorobenzeneboronic acid (0.076 g, 0.399 millimole). To the solution were then added palladium tetrakistriphenylphosphine (0.0154, 0.0133 millimole), DME (2.5 mL) and 2M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product from Step E was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 498 through 501 were similarly prepared according to the procedure above with appropriate selection and substitution the desired optically pure phenethylamine in Step C and appropriate selection and substitution of suitably substituted benzeneboronic acid in Step E.

EXAMPLE 25

COMPOUND # 502

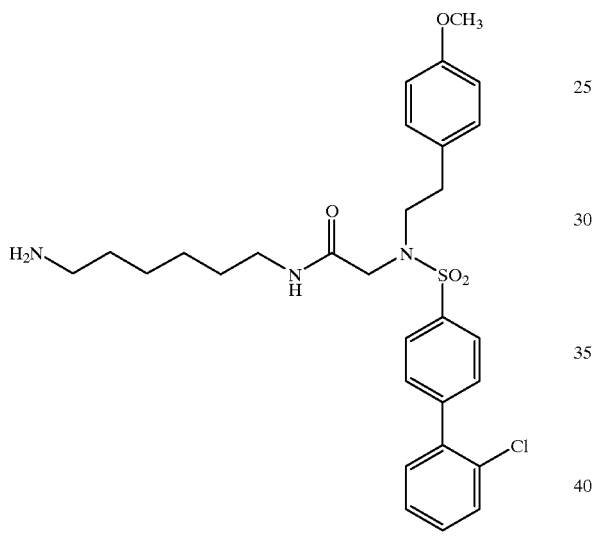

A. Preparation of Amino Carbamate Resin

Wang p-nitrophenylcarbonate resin (4.0 millimoles) was swelled in DMF (approximately 200 ml). To the suspension was added 1,6-hexanediamine (4.65 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from Step A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Secondary Amine on Resin

The 2-bromoacetylated resin (from Step B) was swelled in DMSO (150 mL). To the suspension was added 4-methoxyphenethylamine (6.05 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Bromophenylsulfonamide Resin

The optically pure resin-bound secondary amine resin (from Step C) was swelled in DCM (200 mL). To the suspension was added pyridine (3.19 g) and then 4-bromophenylsulfonyl chloride (5.1 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

The N-(R)-β-methylphenthyl-4-bromophenyl-sulfonamide resin (from Step D) was split into 10 portions, each containing 0.133 millimole of resin. To one portion was added 2-chlorobenzeneboronic acid (0.076 g, 0.399 millimole). To the solution was then added palladium tetrakistriphenylphosphine (0.0154, 0.0133 millimole), DME (2.5 mL) and 2M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product from Step E was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 501 through 515 and 572 through 589 may be similarly prepared according to the procedure above with suitably substituted phenethylamines in Step C.

EXAMPLE 26

COMPOUND #590

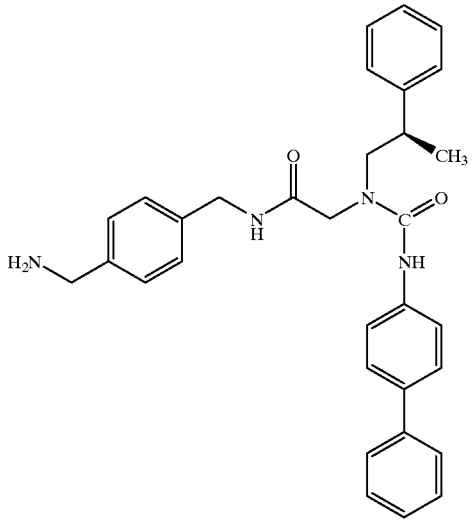

A. Preparation of Amino Carbamate Resin

Wang p-nitrophenylcarbonate resin (4.0 millimoles) was swelled in DMF (approximately 200 ml). To the suspension was added 1,4-xylenediamine (5.44 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from Step A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from Step B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Biphenylurea Resin

The optically pure resin-bound secondary amine resin from Step C (0.150 mmol) was swelled in DCE (2.0 mL). To the suspension was added 4-biphenylisocyanate (0.146 g, 0.750 mmol). The suspension was shaken overnight. The resin was filtered and washed with 3 portions of DCM, 3 portions of methanol, 3 portions of DCM, and 3 portions of methanol. The resin was dried in vacuo overnight.

E. Cleavage of the Resin Support

The product from Step D was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compound #591 was similarly prepared according to the procedure described above with appropriate substitution of (S)-β-methylphenethylamine in Step C.

EXAMPLE 27

COMPOUND # 477

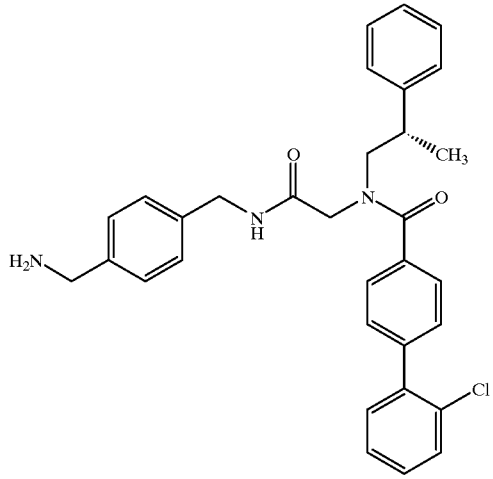

A. Preparation of Amino Carbamate Resin

Wang p-nitrophenylcarbonate resin (4.0 millimoles) was swelled in DMF (approximately 200 ml). To the suspension was added 4,4-methylenebis(cyclohexanamine) (8.41 g, 40 millimoles) dissolved in DMF (75 ml). The mixture was shaken for 24 h. The solvent was removed by filtration. The resin was then washed with 3 portions DMF, 3 portions methanol, 3 portions DCM/5% acetic acid, 3 portions methanol, 3 portions DCM/10% TEA, and 3 portions methanol. The resin was dried in vacuo overnight.

B. Coupling of Bromoacetic Acid

The carbamate resin (from A) was swelled in DMF (approximately 200 ml). To the suspension was added bromoacetic acid (2.77 g, 20 millimoles) and diisopropylcarbodiimide (2.53 g) and shaken overnight. The solvent was removed by filtration. The resin was then washed with 3 portions DMF, 3 portions methanol, and 3 portions DCM.

C. Preparation of the Optically Pure Secondary Amine on Resin

The 2-bromoacetylated resin (from B) was swelled in DMSO (150 mL). To the suspension was added (R)-β-methylphenethylamine (5.408 g, 40.0 millimole) and shaken overnight. The resin was filtered and washed with 3 portions of DMSO, 3 portions of methanol, 3 portions of DCM/5% acetic acid, 3 portions of methanol, 3 portions of DCM/10% TEA, and 3 portions of methanol. The resin was dried in vacuo overnight.

D. Preparation of 4-Iodobenzamide Resin

The optically pure resin-bound secondary amine resin (from C) was swelled in DCM (200 mL). To the suspension was added pyridine (3.19 g) and then 4-iodobenzoyl chloride (5.3 g, 20.0 millimole). The suspension was shaken overnight. The resin was filtered and washed with 3 portions of DCM, 3 portions of methanol, 3 portions of DCM, and 3 portions of methanol. The resin was dried in vacuo overnight.

E. Preparation of Sulfonamide Resin

Five portions of the N-(R)-β-methylphenthyl-4-iodobenzamide resin (from D), each containing 0.133 millimole of resin, were used for the next reaction. To one portion was added 2-chlorobenzeneboronic acid (0.076 g, 0.399 millimole). To the solution was then added palladium tetrakistriphenylphosphine (0.0154, 0.0133 millimole), DME (2.5 mL) and 2 M sodium carbonate solution in water (0.830 mL). The mixture was shaken at 80° C. overnight. The resin was filtered and washed with 3 portions DMF, 3 portions methanol and 3 portions DCM. The resin was dried in vacuo overnight.

F. Cleavage of the Resin Support

The product was cleaved from the resin with a solution of 90:10 TFA/water. The cleavage solution was evaporated. The product was purified by semi-preparative reverse phase HPLC on a 20×100 mm J'sphere H-80 YMC column using a gradient of 90:10:0.1 water:acetonitrile:TFA to 10:90:0.1 water:acetonitrile:TFA. The product was lyophillized and analyzed by ES/MS and reverse phase HPLC.

Compounds 478–481 were similarly prepared according to the procedure above, with appropriate selection and substitution of suitably substituted benzeneboronic acid in Step E.

EXAMPLE 28

IN VITRO TESTING: hFSH-R CHO Cells

Preparation of Biological Materials

Minimum Essential Medium-Alpha (MEM-alpha), fetal bovine serum (FBS), penicillin, streptomycin, geneticin, trypsin-EDTA, Hanks' Balanced Salt Solution (no Calcium chloride, Magnesium chloride, Magnesium sulfate, or phenol red; Ca-Mg free HBSS) were purchased from Gibco BRL (Gaithersburg, Md.). The cells used for the FSH bioassay (rhFSHR-cLUC) were Chinese Hamster Ovary cells (K-1; ATCC) stably transformed with human FSH receptor (pSVK-FSHr) and a cAMP luciferase reporter gene (responsive CGα-180LUC). Follicle Stimulating Hormone (Metrodin; Fertinex) was purchased from Serono, Ltd. (Norwell, Mass.).

The rhFSHR-cLUC cell cultures were maintained in MEM-Alpha supplemented with 10% heat-inactivated FBS (HIFBS), 100 U/ml penicillin, 100 µg/mL streptomycin, and included 0.1 g/L geneticin for stable cell selection.

HFSHR Assay Procedure

Forty-eight hours after the cells were plated in sterile 96-well culture plates (Corning, Corning, N.Y.) the spent media was removed and 50 µl assay media (modified growth media with 2% HIFBS) containing 2 mM IBMX (3-isobutyl-1-methyl-xanthine) was added to the cells. Compounds (25 µl) in the appropriate concentration were added followed 5 minutes later by an $EC_{70}$ dose of FSH (25 µl; 160 ng/ml; 4.85 nM). After 10 minutes @ 22.5° C. (room temperature) the reaction was terminated by addition of 25 µL 0.5 N hydrochloric acid to each well. The amount of cAMP produced was measured by radioimmunoassay in a FlashPlate (DuPont, Boston, Mass.). To each flash plate 60 µL flash plate buffer was added followed by 40 µL acidified cell sample or cAMP standard, followed with the addition of 100 µl $^{125}$I-cAMP trace. The FlashPlates were sealed, incubated overnight @ room temperature, and counted in a Packard TopCount (Packard Instrument Co., Meriden, Conn.). The cAMP radioimmunoassay results were calculated using DPM conversion and log-logit transformation of % binding (Excel program).

Preparation of Test Compound

Test compounds were solubilized in 30% dimethyl sulfoxide (DMSO) at a concentration of 10 mM before diluting to appropriate concentrations in assay medium. The final DMSO concentration in the treated cells and in the control cells was 0.75%. The compounds were tested in the assay at a maximum final concentration of 50 µM (primary assay) and compounds that demonstrated greater than 50% inhibition or greater than 200% stimulation of cAMP production were retested in dose-ranging experiments to calculate an $EC_{50}$.

Derivation and Analysis of Data

For individual experiments, a set of samples were tested including a vehicle control (assay buffer), a reference compound (hFSH) at a range of concentrations designed to elicit a minimal to maximal response, and several concentrations of test compounds together with an $EC_{70}$ concentration of standard (hFSH challenge). Each compound was performed in duplicates for the primary evaluation and quadruplicates for the dose-ranging experiments. The cAMP radioimmunoassay raw data (pmol) were calculated to provide average pmol cAMP produced/ml and the percent inhibition was calculated as shown below.

$$\% \text{Inh} = [1 - (\text{Avg.pmol}_{test\ compound+standard})/(\text{Avg.pmol}_{standard})] \times 100$$

$EC_{50}$ values were calculated from an analysis of the concentration-inhibition data using a linear analysis of the data transformed to a log-logit format.

TABLE 5

| Cmpd # | $EC_{50}$ hFSHR CHO cAMP (µM) |
|---|---|
| 1 | 1.16 |
| 2 | 0.93 |
| 3 | 0.6 |
| 4 | 0.65 |
| 5 | 0.96 |
| 6 | 1.59 |
| 7 | 1.81 |
| 8 | 1.38 |
| 9 | 1.06 |
| 10 | 3.71 |
| 11 | 0.63 |
| 12 | 0.68 |
| 13 | 0.56 |
| 14 | 0.74 |
| 15 | 0.84 |
| 16 | 1.13 |
| 17 | 0.57 |
| 18 | 1.82 |
| 19 | 3.37 |
| 20 | 6.31 |
| 21 | 3.29 |
| 22 | 5.03 |
| 23 | 1.41 |
| 24 | 2.33 |
| 25 | 1.41 |
| 26 | 1.46 |
| 27 | 2.3 |
| 28 | 2.23 |
| 29 | 3.09 |
| 30 | 1.33 |
| 31 | 0.91 |
| 32 | 0.31 |
| 33 | 0.42 |
| 34 | 0.31 |
| 35 | 0.83 |
| 36 | 0.66 |
| 37 | 0.67 |
| 38 | 0.5 |
| 39 | 1.69 |
| 40 | 22.13 |
| 41 | 12.69 |
| 42 | 6.46 |
| 43 | 9.88 |
| 44 | 8.92 |
| 45 | 3.92 |
| 46 | 28.85 |
| 47 | 4.37 |
| 48 | 3.62 |
| 49 | 31.3 |
| 50 | 26.24 |
| 51 | 25 |
| 52 | 28.49 |
| 53 | 29.02 |
| 54 | 33.45 |
| 55 | 50 |
| 56 | 23.32 |
| 57 | 19.52 |
| 58 | 6.24 |
| 59 | 28.48 |
| 60 | 40.02 |
| 61 | 50 |
| 62 | 6.76 |
| 63 | 33.61 |
| 64 | 38.47 |
| 65 | 4.82 |
| 66 | 12.67 |
| 67 | 50 |
| 68 | 37.66 |
| 69 | 5.99 |
| 70 | 18.78 |
| 71 | 11 |
| 72 | 7.85 |
| 73 | 4.95 |
| 74 | 10.68 |
| 75 | 5.09 |
| 76 | 10.21 |

TABLE 5-continued

| Cmpd # | EC$_{50}$ hFSHR CHO cAMP ($\mu$M) |
|---|---|
| 77 | 6.86 |
| 78 | 12.87 |
| 79 | 7.83 |
| 80 | 3.06 |
| 81 | 7.06 |
| 82 | 5.09 |
| 83 | 4.5 |
| 84 | 50 |
| 85 | 7.79 |
| 86 | 12.34 |
| 87 | 7.4 |
| 88 | 12.2 |
| 89 | 50 |
| 90 | 50 |
| 91 | 13.19 |
| 92 | 50 |
| 93 | 15.22 |
| 94 | 34.45 |
| 95 | 5.98 |
| 96 | 8.23 |
| 97 | 4.31 |
| 98 | 6.04 |
| 99 | 3.68 |
| 100 | 4.99 |
| 101 | 4.89 |
| 102 | 3.98 |
| 103 | 28.32 |
| 104 | 9.54 |
| 105 | 31.33 |
| 106 | 12.77 |
| 107 | 9.7 |
| 108 | 5.5 |
| 109 | 4.76 |
| 110 | 10.75 |
| 111 | 8.39 |
| 112 | 10.21 |
| 113 | 16.69 |
| 114 | 9.78 |
| 115 | 2.92 |
| 116 | 8.41 |
| 117 | 3.63 |
| 118 | 1.24 |
| 119 | 0.54 |
| 120 | 1.5 |
| 121 | 33.11 |
| 122 | 0.76 |
| 123 | 4.03 |
| 124 | 1.11 |
| 125 | 7.53 |
| 126 | 2.31 |
| 127 | 10.36 |
| 128 | 4.98 |
| 129 | 2.11 |
| 130 | 1.86 |
| 131 | 1.41 |
| 132 | 2.58 |
| 133 | 50 |
| 134 | 3.86 |
| 135 | 1.02 |
| 136 | 2.13 |
| 137 | 4.32 |
| 138 | 31.21 |
| 139 | 5.76 |
| 140 | 18.57 |
| 141 | 50 |
| 142 | 50 |
| 143 | 5 |
| 144 | 1.08 |
| 145 | 24.26 |
| 146 | 1.73 |
| 147 | 8.06 |
| 148 | 23.5 |
| 149 | 1.01 |
| 150 | 4.53 |
| 151 | 9.79 |
| 152 | 8.58 |
| 153 | 9.44 |
| 154 | 10.68 |
| 155 | 12.64 |
| 156 | 20.37 |
| 157 | 10.27 |
| 158 | 8.34 |
| 159 | 4.54 |
| 160 | 28.53 |
| 161 | 37.9 |
| 162 | 11.24 |
| 163 | 24.27 |
| 164 | 13.8 |
| 165 | 12.46 |
| 166 | 9.09 |
| 167 | 3.48 |
| 168 | 24.84 |
| 169 | 8.96 |
| 170 | 8.66 |
| 171 | 8.99 |
| 172 | 3.76 |
| 173 | 2.23 |
| 174 | 50 |
| 175 | 47.77 |
| 176 | 40.59 |
| 177 | 50 |
| 178 | 50 |
| 179 | 50 |
| 180 | 50 |
| 181 | 50 |
| 182 | 50 |
| 183 | 50 |
| 184 | 50 |
| 185 | 50 |
| 186 | 38.9 |
| 187 | 50 |
| 188 | 50 |
| 189 | 50 |
| 190 | 38.23 |
| 191 | 50 |
| 192 | 32.3 |
| 193 | 50 |
| 194 | 50 |
| 195 | 50 |
| 196 | 50 |
| 197 | 0.36 |
| 198 | 0.04 |
| 199 | 0.83 |
| 200 | 0.32 |
| 201 | 0.41 |
| 202 | 0.21 |
| 203 | 0.08 |
| 204 | 0.54 |
| 205 | 0.22 |
| 206 | 0.35 |
| 207 | 0.35 |
| 208 | 0.06 |
| 209 | 0.77 |
| 210 | 0.23 |
| 211 | 0.49 |
| 212 | 0.16 |
| 213 | 0.07 |
| 214 | 0.15 |
| 215 | 0.08 |
| 216 | 0.62 |
| 217 | 1.2 |
| 218 | 1.2 |
| 219 | 1.77 |
| 220 | 2.1 |
| 221 | 5.86 |
| 222 | 13.52 |
| 223 | 6.51 |
| 224 | 9.81 |
| 225 | 12.8 |
| 226 | 5.5 |
| 227 | 5.5 |
| 228 | 3.65 |

TABLE 5-continued

| Cmpd # | EC$_{50}$ hFSHR CHO cAMP ($\mu$M) |
|---|---|
| 229 | 3.76 |
| 230 | 31.12 |
| 231 | 5.82 |
| 232 | 4.46 |
| 233 | 8.9 |
| 234 | 27.85 |
| 235 | 8.66 |
| 236 | 3.13 |
| 237 | 50 |
| 238 | 10.49 |
| 239 | 7.99 |
| 240 | 6.83 |
| 241 | 7.45 |
| 242 | 3.51 |
| 243 | 5.17 |
| 244 | 2.88 |
| 245 | 5.63 |
| 246 | 4.11 |
| 247 | 6.27 |
| 248 | 5.33 |
| 249 | 6.86 |
| 250 | 17.11 |
| 251 | 5.85 |
| 252 | 8.27 |
| 253 | 8.43 |
| 254 | 4.33 |
| 255 | 2.63 |
| 256 | 2.39 |
| 257 | 1.64 |
| 258 | 2.44 |
| 259 | 2.98 |
| 260 | 3.93 |
| 261 | 5.65 |
| 262 | 2.46 |
| 263 | 31.99 |
| 264 | 5.62 |
| 265 | 2.69 |
| 266 | 3.43 |
| 267 | 2.08 |
| 268 | 50 |
| 269 | 6.76 |
| 270 | 4.19 |
| 271 | 0.96 |
| 272 | 0.55 |
| 273 | 1.16 |
| 274 | 2.08 |
| 275 | 1.6 |
| 276 | 5.1 |
| 277 | 31.89 |
| 278 | 1.09 |
| 279 | 2.45 |
| 280 | 7.63 |
| 281 | 6.95 |
| 282 | 9.4 |
| 283 | 1.27 |
| 284 | 3.51 |
| 285 | 7.89 |
| 286 | 3.88 |
| 287 | 7.52 |
| 288 | 19.51 |
| 289 | 5.68 |
| 290 | 0.67 |
| 291 | 8.94 |
| 292 | 0.68 |
| 293 | 7.36 |
| 294 | 1.54 |
| 295 | 2.18 |
| 296 | 50 |
| 297 | 6.88 |
| 298 | 34.38 |
| 299 | 2.22 |
| 300 | 3.18 |
| 301 | 0.15 |
| 302 | 0.2 |
| 303 | 0.44 |
| 304 | 0.3 |
| 305 | 0.58 |
| 306 | 0.35 |
| 307 | 0.19 |
| 308 | 0.45 |
| 309 | 0.34 |
| 310 | 0.22 |
| 311 | 0.05 |
| 312 | 0.22 |
| 313 | 0.43 |
| 314 | 0.69 |
| 315 | 0.31 |
| 316 | 0.96 |
| 317 | 16.92 |
| 318 | 16.97 |
| 319 | 1.1 |
| 320 | 2.57 |
| 321 | 11.3 |
| 322 | 4.36 |
| 323 | 0.29 |
| 324 | 0.37 |
| 325 | 16.96 |
| 336 | 0.98 |
| 337 | 0.31 |
| 338 | 0.44 |
| 339 | 1.1 |
| 340 | 0.65 |
| 341 | 0.57 |
| 342 | 0.37 |
| 343 | 0.53 |
| 344 | 0.7 |
| 345 | 18.22 |
| 346 | 0.65 |
| 347 | 0.9 |
| 348 | 2.24 |
| 349 | 0.79 |
| 350 | 17.47 |
| 351 | 3.15 |
| 352 | 0.11 |
| 353 | 0.14 |
| 354 | 0.37 |
| 355 | 0.4 |
| 356 | 0.89 |
| 357 | 0.3 |
| 358 | 1.04 |
| 359 | 0.36 |
| 366 | 0.78 |
| 367 | 1.02 |
| 368 | 1.08 |
| 369 | 0.75 |
| 370 | 0.57 |
| 371 | 1.84 |
| 372 | 0.19 |
| 373 | 0.11 |
| 374 | 0.34 |
| 375 | 0.13 |
| 376 | 0.17 |
| 377 | 0.34 |
| 378 | 0.25 |
| 379 | 50 |
| 380 | 1.2 |
| 381 | 0.45 |
| 382 | 0.61 |
| 383 | 2.9 |
| 384 | 0.27 |
| 385 | 0.33 |
| 386 | 1.17 |
| 387 | 1.07 |
| 388 | 0.9 |
| 389 | 1.93 |
| 390 | 0.23 |
| 391 | 0.31 |
| 392 | 0.26 |
| 393 | 0.09 |
| 394 | 0.72 |
| 395 | 2.64 |
| 396 | 0.09 |

TABLE 5-continued

| Cmpd # | EC$_{50}$ hFSHR CHO cAMP ($\mu$M) |
|---|---|
| 397 | 0.05 |
| 398 | 0.22 |
| 399 | 0.23 |
| 400 | 0.16 |
| 401 | 1.36 |
| 402 | 5.36 |
| 412 | 0.32 |
| 413 | 0.08 |
| 414 | 0.35 |
| 415 | 0.72 |
| 416 | 0.51 |
| 417 | 0.44 |
| 418 | 0.85 |
| 419 | 2.07 |
| 420 | 0.64, 0.21 |
| 421 | 0.55 |
| 422 | 0.52 |
| 423 | 1.38 |
| 424 | 18.85 |
| 425 | 0.42 |
| 426 | 0.7 |
| 427 | 4.75 |
| 428 | >50 |
| 429 | 3.03, 0.77 |
| 430 | >50 |
| 431 | 5.98 |
| 432 | >50 |
| 433 | 23.5 |
| 434 | 0.2 |
| 435 | 0.21 |
| 436 | 50 |
| 437 | 32.5 |
| 438 | 0.73 |
| 439 | >50 |
| 440 | 0.9 |
| 441 | 0.12 |
| 442 | >50 |
| 443 | 0.85 |
| 444 | 1.89 |
| 445 | 1.54 |
| 446 | >50 |
| 447 | >50 |
| 448 | >50 |
| 449 | 0.64 |
| 450 | 0.21 |
| 451 | 0.29, 0.52 |
| 452 | 0.58 |
| 453 | 0.37 |
| 454 | 0.86 |
| 455 | 0.23 |
| 456 | 3.35 |
| 457 | 0.58 |
| 458 | 20.9 |
| 459 | 9.05 |
| 460 | 0.17 |
| 461 | 16.3 |
| 462 | 1.22 |
| 463 | 2.14, 0.58 |
| 464 | 0.73 |
| 465 | 2.19 |
| 466 | 1 |
| 467 | 0.07 |
| 468 | 0.51 |
| 469 | 20.01 |
| 470 | 50 |
| 471 | 49.95 |
| 472 | >50 |
| 473 | >50 |
| 474 | >50 |
| 475 | 9.46 |
| 476 | 50 |
| 477 | 7.7 |
| 478 | >50 |
| 479 | 13.25 |
| 480 | 0.62 |
| 481 | 0.67 |
| 483 | 0.46 |
| 484 | 0.14 |
| 485 | 0.11 |
| 486 | 2.33 |
| 487 | 0.11 |
| 488 | 0.22 |
| 489 | 0.35 |
| 490 | 0.59 |
| 491 | 0.11 |
| 492 | 1.08 |
| 493 | 0.99 |
| 494 | 0.45 |
| 495 | 0.62 |
| 496 | 0.13 |
| 497 | 4.04 |
| 498 | 1.33 |
| 499 | 3.46 |
| 500 | 2.55 |
| 501 | 0.79 |
| 502 | 0.3 |
| 503 | 0.39 |
| 504 | >50 |
| 505 | 0.14 |
| 506 | 1.2 |
| 507 | 0.08 |
| 508 | 0.28 |
| 509 | 0.2 |
| 510 | 1.02 |
| 511 | 0.09 |
| 512 | 1.37 |
| 513 | 0.62 |
| 514 | 0.41 |
| 515 | 3.18 |
| 521 | 0.12 |
| 522 | 0.41 |
| 523 | 0.37 |
| 524 | 0.21 |
| 525 | 0.76 |
| 526 | 2.36 |
| 527 | 0.15 |
| 528 | 0.61 |
| 529 | 0.72 |
| 530 | 20 |
| 531 | >50 |
| 532 | 21.9 |
| 533 | 0.92 |
| 534 | 1 |
| 535 | 4.77 |
| 536 | >50 |
| 537 | 0.29 |
| 538 | 0.12 |
| 539 | 4.62 |
| 540 | 50 |
| 541 | 0.21 |
| 542 | 0.1 |
| 543 | 0.77 |
| 544 | 0.82 |
| 545 | 0.19 |
| 546 | 14.8 |
| 547 | 2.5 |
| 548 | 0.23 |
| 549 | 0.29 |
| 550 | 0.36 |
| 551 | 1.27 |
| 552 | 4.2 |
| 553 | 1 |
| 554 | 0.24 |
| 555 | 1.93 |
| 556 | 0.87 |
| 557 | 0.42 |
| 558 | 0.41 |
| 559 | 0.74 |
| 560 | 0.84 |
| 561 | 0.13 |
| 562 | 3 |
| 563 | 1.38 |

TABLE 5-continued

| Cmpd # | EC$_{50}$ hFSHR CHO cAMP ($\mu$M) |
|---|---|
| 564 | 0.87 |
| 572 | 0.13 |
| 573 | 0.04 |
| 574 | 0.21 |
| 575 | 0.87 |
| 576 | 0.1 |
| 577 | 0.14 |
| 578 | 50 |
| 579 | 5.29 |
| 580 | 0.35 |
| 581 | 0.1 |
| 582 | 0.43 |
| 583 | 1.94 |
| 584 | 0.11 |
| 585 | >50 |
| 586 | 1.24 |
| 587 | 0.29 |
| 588 | 1.06 |
| 589 | 0.25 |
| 590 | 2.6 |
| 591 | 50 |

EXAMPLE 29

IN VITRO TESTING: Rat Granulosa Cells

Preparation of Biological Materials

Insulin, diethylstilbesterol, androstenedione, forskolin and DMSO were purchased from Sigma (St. Louis, Mo.). Fungizone, penicillin/streptomycin, charcoal-treated heat inactivated fetal bovine serum (CT-HI-FBS) and Dulbecco's Modified Eagle Medium:Hams F12 medium containing 15 mM Hepes and L-glutamine (DMEM:F12), were purchased from GIBCO BRL (Grand Island, N.Y.).

Ovine FSH (NIADDK-oFSH-17; FSH potency=20 NIH-FSH-S1 U/mg; LH contamination=0.04 times NIH-LH-S1) was received from Ogden Bioservices Corporation, Rockville, Md. Human FSH (Fertinex), was purchased from Serono Pharmaceutical (Framingham, Mass.). Human chorionic gonadotropin (hCG) was purchased from Sigma (St Louis, Mo.).

Granulosa Cell Culture

Immature intact female rats (Wistar-derived strain; 21–23 days old) were implanted with a single pellet (Innovative Research of America, Sarasota, Fla.) containing 2.5 mg diethylstilbesterol (DES) for 3 days. On the third day, the animals were sacrificed, the ovaries were removed, and the granulosa cells were isolated essentially as described in Haynes-Johnson et al., *Biol. Reprod.,* 61 (1), 147–153, (1999). Granulosa cells were plated at a density of 300,000 cells per ml with 0.2 ml added to each well of 96 well culture dishes (Corning, N.Y.). Cultures were incubated at 37° C. in a humidified incubator (95% air, 5% CO2) overnight (18 hours).

For determination of LH-stimulated estrogen production, immature female rats, about 28 days of age, were treated with 75 IU pregnant mares serum gonadotropin (PMSG) and sacrificed 48 hours later. The granulosa cells from large follicles (not corpora lutea) were expressed into media following the procedure outlined above. Granulosa cells were plated at a density of 300,000 cells/ml with 0.2 ml of cell suspension added to each well of a 96-well plate.

Test Procedure

Androstenedione (100,000X) was prepared by dissolving the steroid in 100% ethanol, and was subsequently diluted to a final concentration of $10^{-7}$M containing 0.1% ethanol in assay media. The assay media was serum-free, DES-free, insulin-free media, prepared by adding 5 mL pen-strep,1.5 mL fungizone and 5 $\mu$L androstenedione to 493.5 mL DMEM F-12 media.

Test compounds were solubilized in 30% dimethyl sulfoxide (DMSO) at a concentration of 10 mM before diluting to appropriate concentrations in assay medium. The final DMSO concentration in the treated cells and in the control cells was 0.75%. The compounds were tested in the assay at a maximum final concentration of 50 $\mu$M (primary assay) and compounds that demonstrated greater than 50% inhibition or greater than 200% stimulation of cAMP production were retested in dose-ranging experiments to calculate an $EC_{50}$.

Test plates containing the granulosa cells were preincubated for 18 hours at 37° C. with 95% air, 5% $CO_2$, 100% humidity. The spent media was removed and 50 $\mu$l assay media (DMEM:F12) containing 2 mM IBMX (3-isobutyl-1-methyl-xanthine) was added to the cells. Compounds (25 $\mu$l) in the appropriate concentration were added followed 5 minutes later by an $EC_{70}$ dose of FSH (25 $\mu$l; 50 ng/ml; 1.4 nM). After 30 minutes @ 22.5° C. (room temperature) the reaction was terminated by addition of 25 $\mu$L 0.5 N hydrochloric acid to each well. The amount of cAMP produced was measured by radioimmunoassay in a FlashPlate (DuPont, Boston, Mass.). To each flash plate 60 $\mu$L flash plate buffer was added followed by 40 $\mu$L acidified cell sample or cAMP standard, followed with the addition of 100 $\mu$l $^{125}$I-cAMP trace. The FlashPlates were sealed, incubated overnight @ room temperature, and counted in a Packard TopCount (Packard Instrument Co., Meriden, Conn.). The cAMP radioimmunoassay results were calculated using DPM conversion and log-logit transformation of % binding (Excel program).

Progesterone and Estradiol Production

The effects of the FSH antagonist on steroid production from rat granulosa cells was used to confirm that the effects on cAMP production also caused changes in progesterone and estradiol production, the biologically relevant steroids in vivo. Granulosa cells prepared as described above were incubated in the absence or presence of test compounds for intervals between 12 and 48 hours to determine the effects of compound on FSH-stimulated progesterone and estradiol production. At the end of incubation the media was aspirated (using a multichannel pipettor) into corresponding microtiter plates, and were stored at −20° C. until the concentration of estradiol and progesterone were measured by radioimmunoassay.

Radioimmunoassay of Estradiol and Progesterone

Concentrations of E and P in media from the same culture wells were measured using [$^{125}$I]-progesterone and [$^{125}$I]-estradiol Coat-A-Count radioimmunoassay kits (Diagnostic Products Corp., Los Angeles, Calif.). According to the manufacturers specification sheets, the anti-progesterone antibody cross-reacts 2% with 20a-dihydroprogesterone, 2.4% with 11-deoxycortisol, 1.7% with 11-deoxycorticosterone, and 1.3% with 5b-pregnan-3,20-dione. The cross-reactivity of pregnenolone, 17a-hydroxyprogesterone, and testosterone was less than 0.4%. The assay detection limit was 0.03 ng/ml. The anti-estradiol antibody cross-reacts 10% with estrone, 4.4% with equilenin, 1.8% with estrone glucuronide, 0.3% with estriol, and less than 0.1% with other estrogens and androgens. The assay detection limit was 8 pg/ml.

TABLE 6

| Cmpd # | Rat Granulosa Cell EC$_{50}$ cAMP ($\mu$M) |
|---|---|
| 1 | 2.42 |
| 2 | 0.34 |
| 3 | 0.21 |
| 4 | 0.29 |
| 5 | 0.27 |
| 6 | 0.29 |
| 7 | 0.83 |
| 8 | 0.31 |
| 9 | 0.47 |
| 10 | 1.39 |
| 11 | 0.40 |
| 12 | 0.28 |
| 13 | 0.48 |
| 14 | 1.56 |
| 15 | 5.55 |
| 16 | 0.51 |
| 17 | 0.49 |
| 18 | 0.36 |
| 19 | 1.67 |
| 20 | 0.64 |
| 21 | 5.30 |
| 22 | 0.85 |
| 24 | 1.07 |
| 25 | 1.33 |
| 26 | 4.30 |
| 27 | 1.01 |
| 28 | 1.81 |
| 29 | 2.06 |
| 30 | 0.49 |
| 31 | 1.97 |
| 32 | 0.16 |
| 33 | 0.18 |
| 34 | 0.17 |
| 35 | 0.20 |
| 36 | 0.49 |
| 37 | 0.28 |
| 38 | 1.07 |
| 39 | 0.52 |
| 40 | 1.92 |
| 41 | 0.26 |
| 42 | 1.45 |
| 43 | 0.88 |
| 44 | 0.72 |
| 45 | 2.85 |
| 46 | 6.37 |
| 47 | 0.55 |
| 48 | 1.08 |
| 49 | 2.06 |
| 50 | 1.20 |
| 51 | 3.01 |
| 52 | 3.50 |
| 53 | 3.52 |
| 54 | 3.22 |
| 55 | 12.48 |
| 56 | 5.16 |
| 57 | 1.92 |
| 58 | 2.15 |
| 59 | 2.07 |
| 60 | 29.35 |
| 61 | 7.51 |
| 62 | 1.27 |
| 63 | 3.70 |
| 64 | 1.46 |
| 65 | 1.07 |
| 66 | 4.58 |
| 67 | 25.68 |
| 68 | 3.89 |
| 69 | 5.86 |
| 70 | 5.01 |
| 71 | 3.21 |
| 72 | 2.19 |
| 73 | 1.45 |
| 74 | 8.23 |
| 75 | 0.20 |
| 76 | 0.94 |
| 77 | 0.44 |
| 78 | 0.57 |
| 79 | 1.60 |
| 80 | 0.23 |
| 81 | 25.23 |
| 82 | 0.12 |
| 83 | 0.12 |
| 84 | 7.66 |
| 85 | 0.35 |
| 86 | 2.64 |
| 87 | 0.19 |
| 88 | 0.14 |
| 89 | 1.88 |
| 90 | 0.90 |
| 91 | 0.40 |
| 92 | 3.08 |
| 93 | 0.17 |
| 94 | 8.91 |
| 95 | 0.32 |
| 96 | 3.09 |
| 97 | 0.55 |
| 98 | 0.43 |
| 99 | 0.59 |
| 100 | 0.32 |
| 101 | 25.08 |
| 102 | 0.17 |
| 103 | 0.55 |
| 104 | 32.88 |
| 105 | 8.00 |
| 106 | 10.22 |
| 107 | 1.90 |
| 108 | 1.45 |
| 109 | 3.16 |
| 110 | 4.89 |
| 111 | 1.32 |
| 112 | 8.63 |
| 113 | 0.60 |
| 114 | 8.97 |
| 115 | 1.02 |
| 117 | 1.16 |
| 118 | 2.47 |
| 119 | 2.95 |
| 120 | 1.63 |
| 122 | 1.53 |
| 123 | 10.00 |
| 124 | 1.01 |
| 125 | 2.80 |
| 126 | 25.11 |
| 129 | 1.29 |
| 131 | 1.35 |
| 135 | 1.44 |
| 197 | 0.06 |
| 198 | 0.02 |
| 199 | 0.06 |
| 200 | 0.05 |
| 201 | 0.15 |
| 202 | 0.15 |
| 203 | 0.06 |
| 204 | 0.19 |
| 205 | 0.05 |
| 206 | 0.91 |
| 208 | 0.04 |
| 214 | 0.05 |
| 215 | 0.01 |
| 257 | 1.65 |
| 271 | 2.80 |
| 272 | 0.60 |
| 275 | 2.15 |
| 278 | 0.47 |
| 358 | 0.11 |
| 370 | 0.22 |
| 373 | 0.11 |
| 375 | 0.08 |
| 377 | 0.09 |
| 384 | 0.08 |
| 400 | 0.03 |

EXAMPLE 30

IN VIVO TESTING

Inhibition of FSH-Stimulated Ovarian Proliferation

Twenty-one day old immature female Wistar rats (Charles River) are implanted with Alzet pumps (Alza Corp.,) containing human FSH at a concentration calculated to deliver 4–8IU hFSH per day. The animals are given vehicle or test compound at a dosage level of 20 mg/kg compound (BID) dissolved in hydroxypropyl methylcellulose (HPMC). On the third or fourth day, blood samples are obtained by orbital puncture for the measurement of serum estrogen and progesterone, and immediately afterwards, ovaries and uterus are collected, weighed and prepared for histological examination. The effect of test compound is determined by measuring the weight of ovaries and uterus collected from animals treated with the test compound as compared with the weight of ovaries and uterus collected from animals treated with vehicle.

Interruption of 4-day Estrus Cycle

The estrus cycles of mature cycling female Wistar rats (250 g) were monitored for 2 consecutive estrus cycles to select animals with regular 4-day estrus cycles. The animals were randomly assigned to treatment groups on the morning of estrus. Starting on the morning of estrus and continuing through 2 estrus cycles, the animals orally dosed with vehicle or test compound at a concentration of 20 mg/kg; BID. At the end of the second estrus cycle, blood samples were collected by orbital puncture on the morning of estrus. The animals were then sacrificed, and the number of ovulated eggs in the oviduct were counted.

TABLE 7

| Cmpd. # | Estradiol Concentration | Progesterone Concentration | # Ovulated Eggs |
| --- | --- | --- | --- |
| 198 | 20.1 ± 4.4 | 3.6 ± 0.9 | 14.0 |
| 215 | 22.2 ± 4.2 | 2.6 ± 0.6 | 16.3 |
| Vehicle | 23.8 ± 3.1 | 8.0 ± 2.7 | 16.3 |

Effects on Spermatogenesis in Immature Male Rats

Twenty-one day old immature male Wistar rats (Charles River) were treated with FSH antagonist at a concentration of 20 mg/kg BID for 25 days. On the penultimate day of treatment, blood samples were collected by orbital puncture immediately prior to oral dosing, and 3 hours after dosing into Vacutainers containing EDTA. On the last day of treatment, blood samples were again collected prior to time of compound administration. The concentrations of LH, FSH and testosterone were measured in the plasma. Testosterone was measured using a Coat-A-Count kit (Diagnostic Products Corp.) and luteinizing hormone and follicle stimulating hormone concentrations were measured following previously established. At the end of the treatment period, the animals were sacrificed, testes and prostates were collected and weighed, and the testes were prepared for histological examination. The presence of sperm in testes were evaluated by hematoxylin and eosin staining, and in separate slides with a BERG stain (REF, 1963).

TABLE 8

| Cmpd. # | Serum Testosterone (t = 3 hr, d = 25) | Testes Weight | Prostate Weight | Mating Sperm |
| --- | --- | --- | --- | --- |
| 198 | 3.6 ± 0.6 | 8.8 ± 0.2 | 1.6 ± 0.2 | 3/4 |
| 215 | 4.9 ± 0.7 | 8.7 ± 0.5 | 1.8 ± 0.1 | 1/4 |
| Vehicle | 3.2 0.6 | 7.5 ± 1.6 | 1.6 ± 0.1 | 4/6 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of the formula:

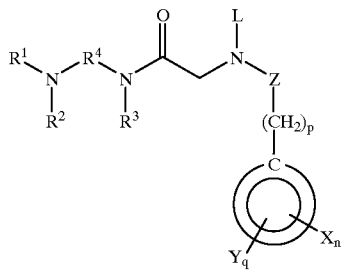

wherein
$R^1$ and $R^2$ are independently selected from the group consisting of hydrogen, $C_1$–$C_6$alkyl, $C_1$–$C_6$alkylcarbonyl, $C_1$–$C_6$perhaloalkyl, phenyl, phenyl $C_1$–$C_6$alkyl-, phenylcarbonyl-, pyridyl, pyridyl $C_1$–$C_6$alkyl-, pyridylcabonyl-, thienyl, thienyl $C_1$–$C_6$alkyl- and thienylcarbonyl, wherein the phenyl, pyridyl or thienyl is optionally substituted with one to three substituents independently selected from halogen, $C_1$–$C_6$alkyl, $C_1$–$C_6$alkoxy, trifluoromethyl, trifluoromethoxy or $NO_2$;

$R^3$ is selected from the group consisting of hydrogen, $C_1$–$C_6$alkyl, $C_2$–$C_4$alkenyl and $C_2$–$C_4$alkynyl, where the $C_1$–$C_6$alkyl is optionally substituted with a phenyl, pyridyl, thienyl or furyl, wherein the phenyl, pyridyl, thienyl or furyl is optionally substituted with one to three substituents independently selected from halogen, $C_1$–$C_6$alkyl, $C_1$–$C_6$alkoxy, trifluoromethyl, trifluoromethoxy or $NO_2$;

$R^4$ is selected from the group consisting of —$C_2$–$C_6$alkyl-, -cyclopentyl-, -cylcohexyl-, -cyclohexyl-$CH_2$—, —$CH_2$-cyclohexyl-$CH_2$—, —$CH_2$-phenyl-$CH_2$—, —C(O)—$CH_2$-phenyl-$CH_2$—, —C(O)—$C_1$–$C_6$alkyl- and -cyclohexyl-$CH_2$-cyclohexyl;

where the $R^4$ substituent is inserted into the compound of formula (I) from left to right, as defined;

alternately, $R^2$, $R^3$, and $R^4$ can be taken together with the two N atoms of the diamine portion of the molecule to form

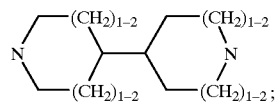

alternately, R³ can be taken together with R² as —C₂–C₃alkyl-, provided that R⁴ is —C₂–C₆alkyl-;

L is selected from the group consisting of —C₃–C₆cycloalkyl (wherein the cycloalkyl is substituted with R⁵ and R⁶), a bicyclic compound of the form

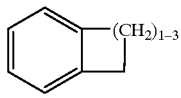

(wherein the point of the attachment of the bicyclic compound is any carbon atom of the alkyl portion and wherein the aromatic portion of the bicyclic compound is optionally substituted with one to three substituents independently selected from halogen, C₁–C₆alkyl, C₁–C₆alkoxy, trifluoromethyl, trifluoromethoxy, NO₂, acetamido, —NH₂, —NH(C₁–C₆alkyl) or —N(C₁–C₆alkyl)₂), and —(CH₂)$_m$—CR⁸R⁵R⁶;

m is 0 to 3;

R⁵ is selected from the group consisting of phenyl, naphthyl, (wherein the phenyl and naphthyl may be optionally substituted with one to three substituents independently selected from halogen, C₁–C₆alkyl, C₁–C₆alkoxy, trifluoromethyl, trifluoromethoxy, NO₂, acetamido, —NH₂, —NH(C₁–C₆alkyl), —N(C₁–C₆alkyl)₂, C₁–C₆alkylcarbonylamino or C₁–C₆alkylsulfonylamino), bicyclo[4.2.0]octa-1,3,5-trienyl, 2,3-dihydro-1H-indolyl, N-methylpyrrolidinyl, 3,4-methylenedioxyphenyl, C₃–C₆cyloalkenyl, (wherein the cycloalkenyl group contains one or two double bonds), a six membered heteroaryl (wherein the six membered heteroaryl contains one to three N atoms), and a five membered heteroaryl (wherein the five membered heteroaryl contains one sulfur, oxygen or nitrogen, optionally contains one to three additional nitrogen atoms); wherein the point of the attachment for the five or six membered heteroaryl is a carbon atom; and wherein the five or six membered heteroaryl is optionally substituted with one to three substituents independently selected from halogen, C₁–C₆alkyl, C₁–C₆alkoxy, trifluoromethyl, trifluoromethoxy or NO₂;

R⁶ is selected from the group consisting of hydrogen, C₁–C₆alkyl, C₃–C₆cycloalkyl, C₁–C₆alkoxy, hydroxy and phenyl, (wherein the phenyl may be optionally substituted with one to three substituents independently selected from halogen, C₁–C₆alkyl, C₁–C₆alkoxy, trifluoromethyl or trifluoromethoxyl); provided that R⁶ may be phenyl only when R⁵ is phenyl;

R⁸ is selected from the group consisting of hydrogen and C₁–C₆alkyl;

Z is selected from the group consisting of —SO₂—, —C(=O)—, and —C(=O)NH—;

p is 0 to 1;

is selected from the group consisting of phenyl and napthyl;

X is selected from the group consisting of halogen, C₁–C₆alkyl, C₁–C₆alkoxy, trifluoromethyl, trifluoromethoxy, NO₂, acetamido, —NH₂, —NH(C₁–C₆alkyl) and —N(C₁–C₆alkyl)₂;

n is 0 to 3;

Y is selected from the group consisting of phenyl, —O-phenyl, —NH-phenyl, naphthyl, (wherein the phenyl or naphthyl is optionally substituted with one to three substituents selected from halogen, C₁–C₆alkyl, C₁–C₆alkoxy, trifluoromethyl, trifluoromethoxy, NO₂, cyano, methylthio, acetamido, formyl, -amino, -aminocarbonyl, —NH C₁–C₆alkyl, —N(C₁–C₆alkyl)₂, —COOH, —COO(C₁–C₆alkyl), —COO(C₁–C₆alkylphenyl), C₁–C₆alkylcarbonylamino, C₁–C₆alkylaminocarbonyl, di(C₁–C₆alkyl)aminocarbonyl, aminosulfonyl, C₁–C₆akylaminosulfonyl or di(C₁–C₆alkyl)aminosulfonyl)), biphenyl, 3,4-methylenedioxyphenyl, dianthrenyl, dibenzothienyl, phenoxathiinyl, a six membered heteroaryl (wherein the six membered heteroaryl contains one to three nitrogen atoms), and a five membered heteroaryl (wherein the five membered heteroaryl contains one sulfur, oxygen or nitrogen atom, optionally contains one to three additional nitrogen atoms); wherein the point of attachment for the five or six membered heteroaryl is a carbon atom; and wherein the five or six membered heteroaryl is optionally substituted with one to three substituents selected from halogen, C₁–C₆alkyl, C₁–C₆alkoxy, trifluoromethyl, trifluoromethoxy, formyl, NO₂, cyano, methylthio, acetamido, -amino, -aminocarbonyl, —NH C₁–C₆alkyl, —N(C₁–C₆alkyl)₂, —COOH, —COO (C₁–C₆alkyl), or —COO(C₁–C₆alkylphenyl));

q is 0 to 1;

provided that when q is 1, n is 0;

and stereoisomers and pharmaceutically acceptable salts or esters thereof.

2. The compound of claim 1 wherein
R¹ and R² are independently selected from the group consisting of hydrogen, methyl, ethyl, methylcarbonyl, trifluoromethyl, phenyl, benzyl, phenylcarbonyl, pyridyl, pyridylcarbonyl, thienyl, thienylmethyl and thienylcarbonyl (where the phenyl, pyridyl or thienyl is optionally substituted with one to two substituents independently selected from halogen, C₁–C₃alkyl, C₁–C₃alkoxy, trifluoromethyl, trifluoromethoxy or nitro); and
R³ is selected from the group consisting of hydrogen and methyl.

3. The compound of claim 1 wherein R¹, R², and R³ are the same and are hydrogen.

4. The compound of claim 1 wherein one of R¹ or R² is other than hydrogen.

5. The compound of claim 1 wherein R² and R³ are taken together as C₂–C₃alkyl and R⁴ is C₂–C₆alkyl.

6. The compound of claim 1 wherein R², R³, and R⁴ are taken together with the two N atoms of the diamine portion of the molecule to form

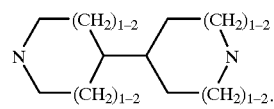

7. The compound of claim 1 wherein R⁴ is selected from the group consisting of —C₂–C₆alkyl, -cyclohexyl, —CH₂-cyclohexyl-CH₂, -cyclohexyl-CH₂-cyclohexyl- and —CH₂-phenyl-CH₂—.

8. The compound of claim 1 wherein L is selected from the group consisting of -cyclopropyl-, cyclohexyl-, (wherein the cyclopropyl or cyclohexyl is substituted with $R^5$ and $R^6$),

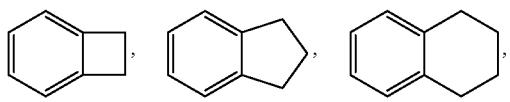

and $(CH_2)_m—CR^8R^5R^6$.

9. The compound of claim 1 wherein $R^5$ is selected from the group consisting of phenyl (wherein the phenyl is optionally substituted with one to two substituents independently selected from halogen, $C_1$–$C_3$alkyl, $C_1$–$C_3$alkoxy, trifluoromethyl, trifluoromethoxy, methylcarbonylamino, methylsulfonylamino, nitro, acetomido, amino, $C_1$–$C_3$alkylamino or di($C_1$–$C_3$alkyl)amino), N-methylpyrrolidinyl, 3,4-methylenedioxyphenyl, bicyclo[4.2.0]octa-1,3,5-trienyl, 2,3-dihydro-1H-indolyl, $C_3$–$C_6$cycloalkenyl (wherein the cycloalkenyl contains one or two double bonds), thienyl, furyl, pyrrolyl, oxazolyl, imidazolyl, pyrazolyl, triazolyl, pyridyl, pyrimidyl, pyrazinyl and triazinyl.

10. The compound of claim 1 wherein $R^6$ is selected from the group consisting of hydrogen, $C_1$–$C_3$alkyl, cyclopropyl, cyclobutyl, cyclohexyl, $C_1$–$C_3$alkoxy, hydroxy and phenyl (wherein the phenyl is optionally substituted with one to two substituents independently selected from halogen, $C_1$–$C_3$alkyl, $C_1$–$C_3$alkoxy, trifluoromethyl or trifluoromethoxy); provided that $R^6$ is phenyl only when $R^5$ is phenyl.

11. The compound of claim 1 wherein $R^8$ is selected from the group consisting of hydrogen and $C_1$–$C_3$alkyl.

12. The compound of claim 1 wherein X is selected from the group consisting of halogen, $C_1$–$C_6$alkyl, $C_1$–$C_4$alkoxy, trifluoromethyl, trifluoromethoxy, nitro, acetamido, amino, $C_1$–$C_3$alkylamino and di($C_1$–$C_3$alkyl)amino.

13. The compound of claim 1 wherein Y is selected from the group consisting of phenyl, naphthyl (wherein the phenyl or naphthyl is optionally substituted with one to three substituents independently selected from halogen, $C_1$–$C_3$alkyl, $C_1$–$C_3$alkoxy, trifluoromethyl, trifluoromethoxy, formyl, nitro, cyano, methylthio, acetamido, amino, aminocarbonyl, $C_1$–$C_3$alkylamino, di($C_1$–$C_3$alkyl)amino, carboxy, —COO($C_1$–$C_3$alkyl), —COO($C_1$–$C_3$alkylphenyl), $C_1$–$C_4$alkylaminosulfonyl or $C_1$–$C_4$alkylcarbonylamino), 3,4-methylenedioxyphenyl, dianthryl, dibenzothienyl, phenoxathiinyl, a five membered heteroaryl (wherein the five membered heteroaryl contains one nitrogen, oxygen or sulfur atom and optionally contains an additional nitrogen or oxygen atom) and a six membered heteroaryl (wherein the six membered heteroaryl contains one nitrogen atom and optionally contains an additional nitrogen or oxygen atom); wherein the five or six membered heteroaryl is optionally substituted with one to two substituents independently selected from halogen, $C_1$–$C_3$alkyl, $C_1$–$C_3$alkoxy, trifluoromethyl, trifluoromethoxy, formyl, nitro, cyano, methylthio, acetamido, amino, aminocarbonyl, $C_1$–$C_3$alkylamino or di($C_1$–$C_3$alkyl)amino; and wherein the point of attachment for the five or six membered heteroaryl is a carbon atom.

14. The compound of claim 1 of the formula

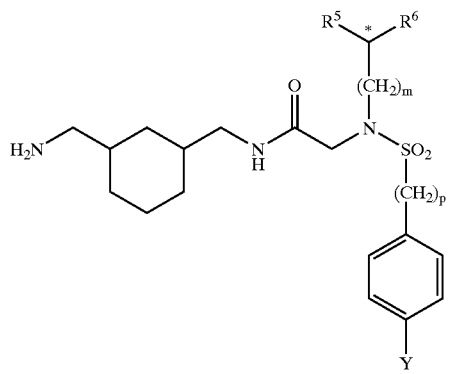

wherein m, $R^5$, $R^6$, p, Y and the stereospecificity are selected in concert from the group consisting of:

| m | $R^5$ | $R^6$ | Stereo | p | Y |
|---|---|---|---|---|---|
| 1 | 2-methoxyphenyl | H | — | 0 | 2-methylphenyl |
| 1 | 2-methoxyphenyl | H | — | 0 | 2-chlorophenyl |
| 1 | 2-methoxyphenyl | H | — | 0 | 2-methoxyphenyl |
| 1 | 2-methoxyphenyl | H | — | 0 | 2,4-dichlorophenyl |
| 0 | 2-methoxyphenyl | H | — | 0 | 2-methylphenyl |
| 0 | 2-methoxyphenyl | H | — | 0 | 2-chlorophenyl |
| 0 | 2-methoxyphenyl | H | — | 0 | 2-methoxyphenyl |
| 0 | 2-methoxyphenyl | H | — | 0 | 2,4-dichlorophenyl |
| 1 | phenyl | $CH_3$ | R | 0 | 2-methylphenyl |
| 1 | phenyl | $CH_3$ | R | 0 | 2-chlorophenyl |
| 1 | phenyl | $CH_3$ | R | 0 | 3-fluorophenyl |
| 1 | phenyl | $CH_3$ | S | 0 | 2-methylphenyl |
| 1 | phenyl | $CH_3$ | S | 0 | 2-chlorophenyl |
| 1 | phenyl | $CH_3$ | S | 0 | 3-fluorophenyl | and stereoisomers and pharmaceutically acceptable salts or esters thereof.

15. The compound of claim 1 of the formula

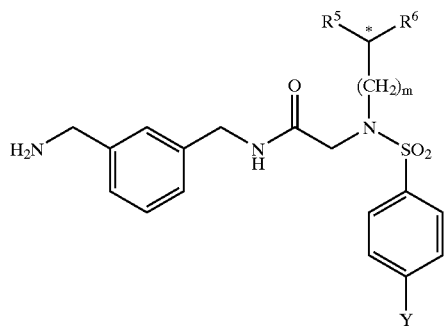

wherein m, $R^5$, $R^6$, p, Y and the stereospecificity are selected in concert from the group consisting of:

| m | $R^5$ | $R^6$ | Stereo | p | Y |
|---|---|---|---|---|---|
| 1 | 2-methoxyphenyl | H | — | 0 | 2-methylphenyl |
| 1 | 2-methoxyphenyl | H | — | 0 | 2-chlorophenyl |
| 1 | 2-methoxyphenyl | H | — | 0 | 2-methoxyphenyl |
| 1 | 2-methoxyphenyl | H | — | 0 | 2,4-dichlorophenyl |
| 0 | 2-methoxyphenyl | H | — | 0 | 2-methyl |
| 0 | 2-methoxyphenyl | H | — | 0 | 2-chlorophenyl |
| 0 | 2-methoxyphenyl | H | — | 0 | 2-methoxyphenyl |
| 0 | 2-methoxyphenyl | H | — | 0 | 2,4-dichlorophenyl |
| 1 | phenyl | $CH_3$ | R | 0 | 2-methylphenyl |
| 1 | phenyl | $CH_3$ | R | 0 | 2-chlorophenyl |
| 1 | phenyl | $CH_3$ | R | 0 | 3-fluorophenyl |

-continued

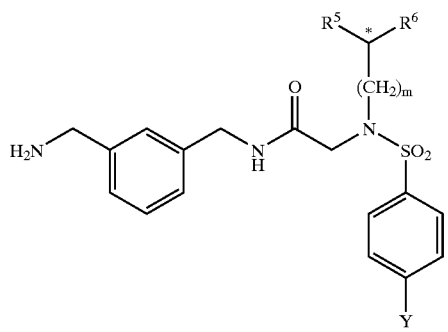

wherein m, R⁵, R⁶, p, Y and the stereospecificity are selected in concert from the group consisting of:

| m | R⁵ | R⁶ | Stereo | p | Y |
|---|---|---|---|---|---|
| 1 | phenyl | CH₃ | S | 0 | 2-methylphenyl |
| 1 | phenyl | CH₃ | S | 0 | 2-chlorophenyl |
| 1 | phenyl | CH₃ | S | 0 | 3-fluorophenyl | and stereoisomers and pharmaceutically acceptable salts or esters thereof.

16. The compound of claim 1 of the formula

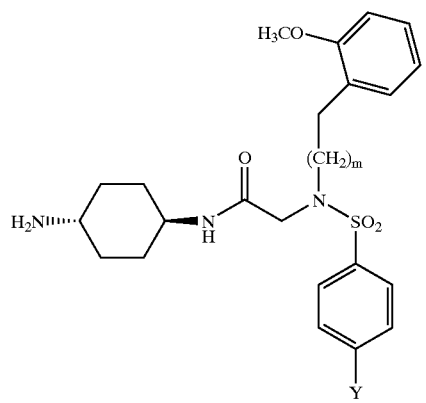

wherein m and Y are selected in concert from the group consisting of:

| m | Y |
|---|---|
| 0 | 2-methylphenyl |
| 0 | 3-thienyl |
| 0 | 2-methoxyphenyl |
| 0 | 4-fluorophenyl |
| 0 | 2,3-dimethoxyphenyl |
| 0 | 4-methoxyphenyl |
| 0 | 4-methylphenyl |
| 0 | 1-napthyl |
| 0 | 2-chlorophenyl |
| 0 | 3-pyridyl |
| 0 | 2-thienyl |
| 0 | 3-aminocarbonylphenyl |
| 0 | phenyl |
| 0 | 4-chlorophenyl |
| 0 | 4-[3,5-dimethylisoxazolyl] |
| 0 | 2-furyl |
| 0 | 4-cyanophenyl |
| 0 | 4-pyridyl |
| 0 | 3-methoxyphenyl |
| 0 | 4-aminophenyl |
| 1 | 2-methylphenyl |
| 1 | 3-thienyl |
| 1 | 2-methoxyphenyl |

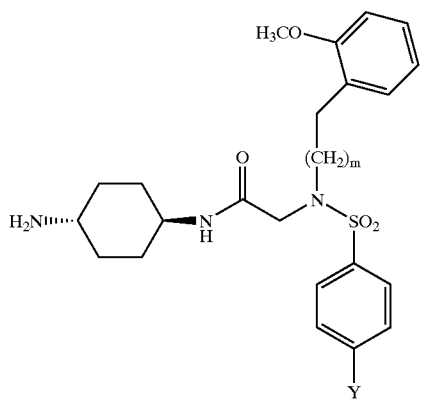

wherein m and Y are selected in concert from the group consisting of:

| m | Y |
|---|---|
| 1 | 4-fluorophenyl |
| 1 | 2,3-dimethyoxyphenyl |
| 1 | 4-methoxyphenyl |
| 1 | 4-methyiphenyl |
| 1 | 1-napthyl |
| 1 | 2-chlorophenyl |
| 1 | 3-pyridyl |
| 1 | 2-thienyl |
| 1 | 3-aminocarbonylphenyl |
| 1 | phenyl |
| 1 | 4-chlorophenyl |
| 1 | 4-[3,4-dimethylisoxazolyl] |
| 1 | 2-furyl |
| 1 | 4-cyanophenyl |
| 1 | 4-pyridyl |
| 1 | 3-methoxyphenyl |
| 1 | 4-aminophenyl | and stereoisomers and pharmaceutically acceptable salts or esters thereof.

17. The compound of claim 1 of the formula

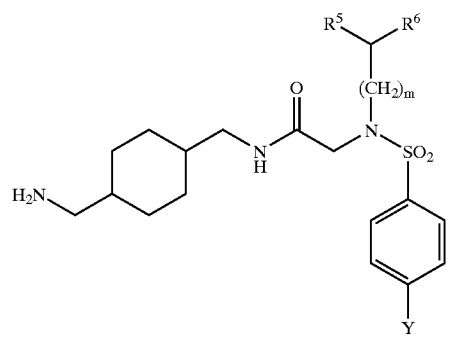

wherein m, R⁵, R⁶ and Y are selected in concert from the group consisting of:

| m | R⁵ | R⁶ | Y |
|---|---|---|---|
| 0 | 2-methoxyphenyl | H | 4-chlorophenyl |
| 0 | 2-methoxyphenyl | H | 3-trifluoromethylphenyl |
| 0 | 2-methoxyphenyl | H | 2-chlorophenyl |
| 0 | 2-methoxyphenyl | H | 2-methyiphenyl |
| 0 | 2-methoxyphenyl | H | 2-methoxyphenyl |
| 0 | 2-methoxyphenyl | H | 2,4-dichlorophenyl |
| 0 | 2-methoxyphenyl | H | 3,5-di(trifluoromethyl)phenyl |
| 0 | 2-methoxyphenyl | H | 3-chloro-4-fluorophenyl |
| 0 | 2-methoxyphenyl | H | 4-methoxyphenyl |

-continued

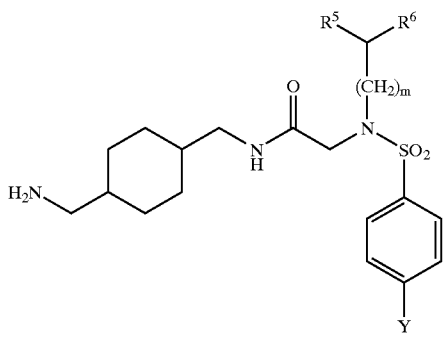

wherein m, R⁵, R⁶ and Y are selected in concert from the group consisting of:

| m | R⁵ | R⁶ | Y |
|---|---|---|---|
| 0 | 3-methoxyphenyl | H | 3-trifluoromethylphenyl |
| 0 | 3-methoxyphenyl | H | 2-methoxyphenyl |
| 0 | 3-methoxyphenyl | H | 2,4-dichlorophenyl |
| 0 | 3-methoxyphenyl | H | 3-fluorophenyl |
| 0 | 3-methoxyphenyl | H | 3-methoxyphenyl |
| 0 | 3-methoxyphenyl | H | 4-methylphenyl |
| 0 | 3-methoxyphenyl | H | 4-fluorophenyl |
| 0 | 3-methoxyphenyl | H | 3-chloro-4-fluorophenyl |
| 0 | 3-methoxyphenyl | H | 4-methoxyphenyl |
| 1 | 2-methoxyphenyl | H | 3-trifluoromethyl phenyl |
| 1 | 2-methoxyphenyl | H | 3-nitrophenyl |
| 1 | 2-methoxyphenyl | H | 2-chlorophenyl |
| 1 | 2-methoxyphenyl | H | 2-methylphenyl |
| 1 | 2-methoxyphenyl | H | 2-methoxyphenyl |
| 1 | 2-methoxyphenyl | H | 2,4-dichlorophenyl |
| 1 | 2-methoxyphenyl | H | phenyl |
| 1 | 2-methoxyphenyl | H | 3-chlorophenyl |
| 1 | 2-methoxyphenyl | H | 4-fluorophenyl |
| 1 | 2-methoxyphenyl | H | 2-trifluoromethyl phenyl | and stereoisomers and pharmaceutically acceptable salts or esters thereof.

18. The compound of claim 1 of the formula

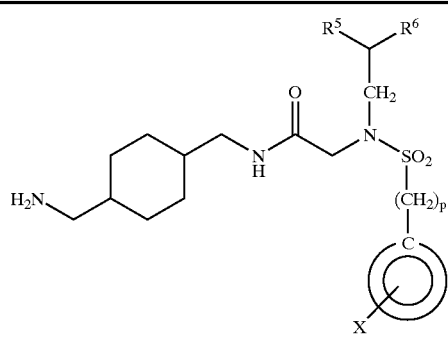

wherein R⁵, R⁶, p,  and X are selected in concert from the group consisting of;

| R⁵ | R⁶ | p | ⌬(C) | X |
|---|---|---|---|---|
| 2-methoxyphenyl | H | 0 | phenyl | — |
| 2-methoxyphenyl | H | 0 | 1-phenyl | 3-trifluoromethyl |
| 2-methoxyphenyl | H | 0 | 1-phenyl | 2-trifluoromethyl |
| 2-methoxyphenyl | H | 0 | 1-phenyl | 3-chloro |
| 2-methoxyphenyl | H | 0 | 1-phenyl | 3,4-dichloro |
| 2-methoxyphenyl | H | 0 | 2-napthyl | — |
| 2-methoxyphenyl | H | 0 | 1-phenyl | 2-chloro |
| 2-methoxyphenyl | H | 0 | 1-phenyl | 4-chloro |
| 2-methoxyphenyl | H | 0 | 1-phenyl | 2,4-dichloro |
| 2-methoxyphenyl | H | 0 | 1-phenyl | 2,6-dichloro |
| 2-methoxyphenyl | H | 0 | 1-phenyl | 3,5-dichloro |
| 2-methoxyphenyl | H | 0 | 1-phenyl | 2,5-dichloro |
| 2-methoxyphenyl | H | 0 | 1-phenyl | 2,3-dichloro |
| 2-methoxyphenyl | H | 1 | phenyl | — |
| 2-methoxyphenyl | H | 0 | 1-phenyl | 4-methyl |
| 2-methoxyphenyl | H | 0 | 1-phenyl | 4-methoxy |
| 2-methoxyphenyl | H | 0 | 1-napthyl | — |
| 2-methoxyphenyl | H | 0 | 1-phenyl | 4-fluoro |
| 2-methoxyphenyl | H | 0 | 1-phenyl | 3,4-dimethoxy |
| 2-methoxyphenyl | H | 0 | 1-phenyl | 2,5-dimethoxy |
| 2-methoxyphenyl | H | 0 | 1-phenyl | 2-nitro |
| 2-methoxyphenyl | H | 0 | 1-phenyl | 4-nitro |
| 2-methoxyphenyl | H | 0 | 1-phenyl | 3-nitro |
| 2-methoxyphenyl | H | 0 | 1-phenyl | 4-iodo |
| 2-methoxyphenyl | H | 0 | 1-phenyl | 4-tert-butyl |
| 2-methoxyphenyl | H | 0 | 1-phenyl | 2-nitro-4-methoxy |
| 2-methoxyphenyl | H | 0 | 1-phenyl | 3-methyl-4-methoxy |
| 2-methoxyphenyl | H | 0 | 1-phenyl | 2-nitro-4-trifluoromethyl |
| 2-methoxyphenyl | H | 0 | 1-phenyl | 3-fluoro |
| 2-methoxyphenyl | H | 0 | 1-phenyl | 2-fluoro |
| 2-methoxyphenyl | H | 0 | 1-phenyl | 4-trifluoromethyl |
| 2-methoxyphenyl | H | 0 | 1-phenyl | 4-trifluoromethoxy |
| 2-methoxyphenyl | H | 0 | 1-phenyl | 2,3-dichloro | and stereoisomers and pharmaceutically acceptable salts or esters thereof.

19. The compound of claim 1 of the formula

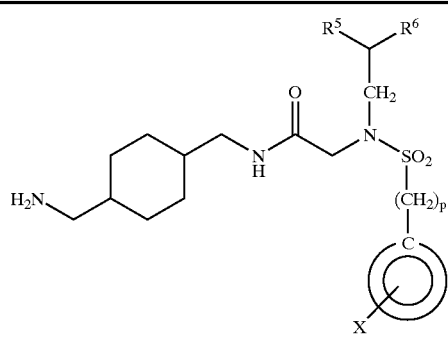

wherein the stereospecificity and Y are selected in concert from the group consisting of:

| Stereo | Y |
|---|---|
| R | 2-methylphenyl |
| R | 2-chlorophenyl |
| R | 3-fluorophenyl |
| S | 2-methylphenyl |
| S | 2-chlorophenyl |
| S | 3-fluorophenyl | and stereoisomers and pharmaceutically acceptable salts or esters thereof.

20. The compound of claim 1 of the formula

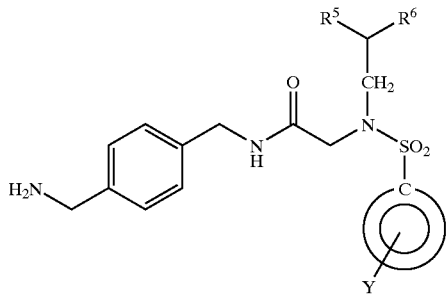

wherein R⁵, R⁶,

Y and stereospecificity are selected in concert from the group consisting of:

| R⁵ | R⁶ | Stereo |  | Y |
|---|---|---|---|---|
| 2-methoxyphenyl | H | — | 1,4-phenyl | 3-nitrophenyl |
| 2-methoxyphenyl | H | — | 1,4-phenyl | 2-chlorophenyl |
| 2-methoxyphenyl | H | — | 1,4-phenyl | 2-methylphenyl |
| 2-methoxyphenyl | H | — | 1,4-phenyl | 2-methoxyphenyl |
| 2-methoxyphenyl | H | — | 1,4-phenyl | 3-fluorophenyl |
| 2-methoxyphenyl | H | — | 1,4-phenyl | phenyl |
| 2-methoxyphenyl | H | — | 1,4-phenyl | 3-methoxy phenyl |
| 2-methoxyphenyl | H | — | 1,4-phenyl | 4-fluorophenyl |
| 2-methoxyphenyl | H | — | 1,4-phenyl | 2-trifluoromethylphenyl |
| 2-methoxyphenyl | H | — | 1,4-phenyl | 3-chloro-4-fluorophenyl |
| phenyl | CH₃ | R | 1,4-phenyl | phenyl |
| phenyl | CH₃ | S | 1,4-phenyl | phenyl |
| phenyl | CH₃ | S | 1,4-phenyl | 2-chlorophenyl |
| phenyl | CH₃ | S | 1,4-phenyl | 3-chlorophenyl |
| phenyl | CH₃ | S | 1,4-phenyl | 2-methoxyphenyl |
| phenyl | CH₃ | S | 1,4-phenyl | 3-methoxyphenyl |
| phenyl | CH₃ | S | 1,4-phenyl | 4-methoxyphenyl |
| phenyl | CH₃ | S | 1,4-phenyl | 3-fluorophenyl |
| phenyl | CH₃ | S | 1,4-phenyl | 4-fluorophenyl |
| phenyl | CH₃ | S | 1,4-phenyl | 2-methylphenyl |
| phenyl | CH₃ | S | 1,4-phenyl | 4-methylphenyl |
| 2-methoxyphenyl | H | — | 1,2-phenyl | 2-thienyl |
| 2-methoxyphenyl | H | — | 1,2-phenyl | 2-methylphenyl |
| 2-methoxyphenyl | H | — | 1,2-phenyl | 3-thienyl |
| 2-methoxyphenyl | H | — | 1,2-phenyl | 2-methoxyphenyl |
| 2-methoxyphenyl | H | — | 1,2-phenyl | 4-fluorophenyl |
| 2-methoxyphenyl | H | — | 1,2-phenyl | 4-methoxyphenyl |
| 2-methoxyphenyl | H | — | 1,2-phenyl | 4-methylphenyl |
| 2-methoxyphenyl | H | — | 1,2-phenyl | 1-napthyl |
| 2-methoxyphenyl | H | — | 1,2-phenyl | 4-chlorophenyl |
| 2-methoxyphenyl | H | — | 1,2-phenyl | 3-methoxy phenyl |
| 2-methoxyphenyl | H | — | 1,2-phenyl | 3-aminophenyl |
| 2-methoxyphenyl | H | — | 1,2-phenyl | 3-fluorophenyl |
| 2-methoxyphenyl | H | — | 1,2-phenyl | 2-fluorophenyl |
| 2-methoxyphenyl | H | — | 1,2-phenyl | 1-(3,4-methylene dioxyphenyl) |
| 2-methoxyphenyl | H | — | 1,2-phenyl | phenyl |
| 2-methoxyphenyl | H | — | 1,2-phenyl | 4-(3,5-dimethyl isoxazole) |
| 2-methoxyphenyl | H | — | 1,2-phenyl | 4-cyanophenyl |
| 2-methoxyphenyl | H | — | 1,2-phenyl | 4-pyridyl |
| 2-methoxyphenyl | H | — | 1,2-phenyl | 2,3,4-trimethoxyphenyl |

-continued

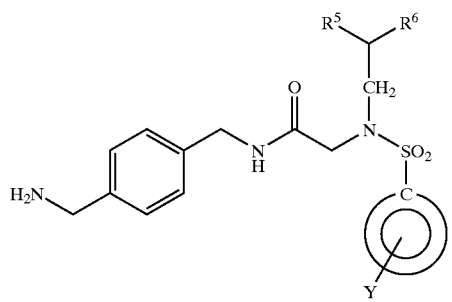

wherein R⁵, R⁶,

Y and stereospecificity are selected in concert from the group consisting of:

| R⁵ | R⁶ | Stereo |  | Y |
|---|---|---|---|---|
| 2-methoxyphenyl | H | — | 1,2-phenyl | 3-cyanophenyl |
| 2-methoxyphenyl | H | — | 1,2-phenyl | 2,5-dimethoxyphenyl |
| 2-methoxyphenyl | H | — | 1,2-phenyl | 2,4-dichlorophenyl |
| 2-methoxyphenyl | H | — | 1,2-phenyl | 3-trifluoromethylphenyl |
| 2-methoxyphenyl | H | — | 1,2-phenyl | 4-trifluoromethylphenyl |
| 2-methoxyphenyl | H | — | 1,2-phenyl | 2-trifluoromethylphenyl |
| 2-methoxyphenyl | H | — | 1,2-phenyl | 3-methylphenyl |
| 2-methoxyphenyl | H | — | 1,3-phenyl | 2-methylphenyl |
| 2-methoxyphenyl | H | — | 1,3-phenyl | 3-thienyl |
| 2-methoxyphenyl | H | — | 1,3-phenyl | 2-methoxyphenyl |
| 2-methoxyphenyl | H | — | 1,3-phenyl | 4-fluorophenyl |
| 2-methoxyphenyl | H | — | 1,3-phenyl | 4-methoxyphenyl |
| 2-methoxyphenyl | H | — | 1,3-phenyl | 4-methoxyphenyl |
| 2-methoxyphenyl | H | — | 1,3-phenyl | 1-napthyl |
| 2-methoxyphenyl | H | — | 1,3-phenyl | 3-pyridyl |
| 2-methoxyphenyl | H | — | 1,3-phenyl | 4-chlorophenyl |
| 2-methoxyphenyl | H | — | 1,3-phenyl | 3-methoxyphenyl |
| 2-methoxyphenyl | H | — | 1,3-phenyl | 3-aminophenyl |
| 2-methoxyphenyl | H | — | 1,3-phenyl | 3-fluorophenyl |
| 2-methoxyphenyl | H | — | 1,3-phenyl | 2-fluorophenyl |
| 2-methoxyphenyl | H | — | 1,3-phenyl | 1-(3,4-methylene dioxyphenyl) |
| 2-methoxyphenyl | H | — | 1,3-phenyl | 3-chlorophenyl |
| 2-methoxyphenyl | H | — | 1,3-phenyl | phenyl |
| 2-methoxyphenyl | H | — | 1,3-phenyl | 4-(3,5-dimethyl isoxazole) |
| 2-methoxyphenyl | H | — | 1,3-phenyl | 4-cyanophenyl |
| 2-methoxyphenyl | H | — | 1,3-phenyl | 4-pyridyl |
| 2-methoxyphenyl | H | — | 1,3-phenyl | 2,3,4-trimethoxyphenyl |
| 2-methoxyphenyl | H | — | 1,3-phenyl | 4-cyanophenyl |
| 2-methoxyphenyl | H | — | 1,3-phenyl | 2,5-dimethoxyphenyl |
| 2-methoxyphenyl | H | — | 1,3-phenyl | 3-trifluoromethylphenyl |

-continued

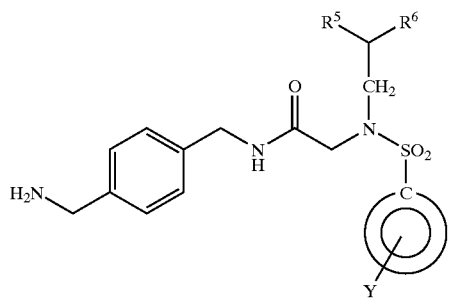

wherein R⁵, R⁶,

Y and stereospecificity are selected in concert from the group consisting of:

| R⁵ | R⁶ | Stereo | | Y |
|---|---|---|---|---|
| 2-methoxyphenyl | H | — | 1,3-phenyl | 4-trifluoromethylphenyl |
| 2-methoxyphenyl | H | — | 1,3-phenyl | 2-trifluoromethytphenyl |
| 2-methoxyphenyl | H | — | 1,3-phenyl | 3-methylphenyl | and stereoisomers and pharmaceutically acceptable salts or esters thereof.

21. The compound of claim 1 of the formula

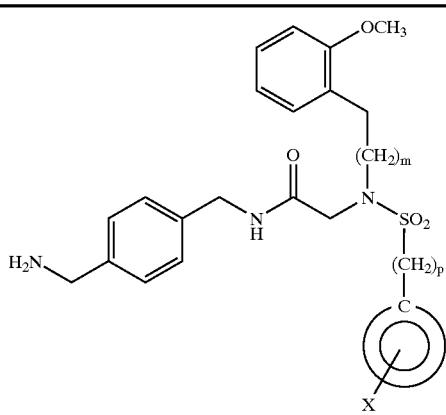

wherein p, m,

and X are selected in concert from the group consisting of:

| p | m | | X |
|---|---|---|---|
| 0 | 1 | phenyl | 3-trifluoromethyl |
| 0 | 1 | phenyl | 2-trifluoromethyl |
| 0 | 1 | phenyl | 3-chloro |
| 0 | 1 | phenyl | 3,4-dichloro |
| 0 | 1 | 2-napthyl | — |
| 0 | 1 | phenyl | 2-chloro |

-continued

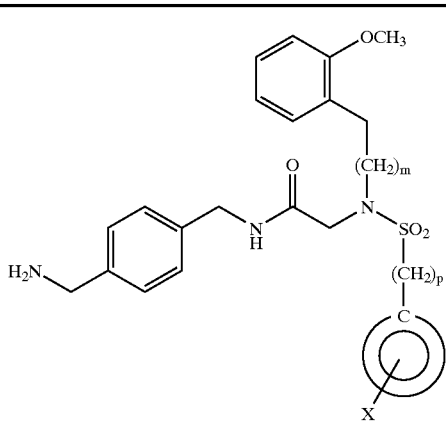

wherein p, m,

and X are selected in concert from the group consisting of:

| p | m | | X |
|---|---|---|---|
| 0 | 1 | phenyl | 2,5-dimethoxy |
| 0 | 1 | phenyl | 2,4-dichloro |
| 0 | 1 | phenyl | 2,6-dichloro |
| 0 | 1 | phenyl | 2,5-dichloro |
| 0 | 1 | phenyl | 3,5-dichloro |
| 1 | 1 | phenyl | — |
| 0 | 1 | phenyl | 4-methoxy |
| 0 | 1 | 1-napthyl | — |
| 0 | 1 | phenyl | 4-fluoro |
| 0 | 1 | phenyl | 3-fluoro |
| 0 | 1 | phenyl | 2-fluoro |
| 0 | 1 | phenyl | 3,4-dimethoxy |
| 0 | 1 | phenyl | 2-nitro |
| 0 | 1 | phenyl | 3-nitro |
| 0 | 1 | phenyl | 4-nitro |
| 0 | 1 | phenyl | 4-iodo |
| 0 | 1 | phenyl | 4-t-butyl |
| 0 | 1 | phenyl | 2-nitro-4-methoxy |
| 0 | 1 | phenyl | 2-methoxy-5-methyl |
| 0 | 1 | phenyl | 2-nitro-4-trifluoro methyl |
| 0 | 1 | phenyl | 4-trifluoromethyl |
| 0 | 1 | phenyl | 4-trifluoromethoxy |
| 0 | 1 | phenyl | 4-methyl |
| 0 | 1 | phenyl | 4-chloro |
| 0 | 1 | phenyl | — |
| 0 | 0 | 1-phenyl | 2,3-dichloro | and stereoisomers and pharmaceutically acceptable salts or esters thereof.

22. The compound of claim 1 of the formula

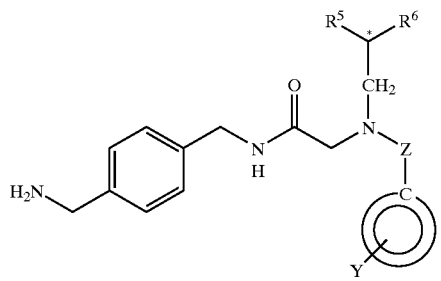

wherein $R^5$, $R^6$, Z,

Y and the stereospecificity are selected in concert from the group consisting of:

| $R^5$ | $R^6$ | Stereo | Z | | Y |
|---|---|---|---|---|---|
| phenyl | CH$_3$ | R | SO$_2$ | 1,4-phenyl | 2-chlorophenyl |
| phenyl | CH$_3$ | R | SO$_2$ | 1,4-phenyl | 3-chlorophenyl |
| phenyl | CH$_3$ | R | SO$_2$ | 1,4-phenyl | 2-methoxyphenyl |
| phenyl | CH$_3$ | R | SO$_2$ | 1,4-phenyl | 3-methoxyphenyl |
| phenyl | CH$_3$ | R | SO$_2$ | 1,4-phenyl | 4-methoxyphenyl |
| phenyl | CH$_3$ | R | SO$_2$ | 1,4-phenyl | 3-fluorophenyl |
| phenyl | CH$_3$ | R | SO$_2$ | 1,4-phenyl | 4-fluorophenyl |
| phenyl | CH$_3$ | R | SO$_2$ | 1,4-phenyl | 2-methylphenyl |
| phenyl | CH$_3$ | R | SO$_2$ | 1,4-phenyl | 4-methylphenyl |
| 2-methoxyphenyl | H | — | SO$_2$ | 1,2-phenyl | 3-chlorophenyl |
| 2-methoxyphenyl | H | — | SO$_2$ | 1,3-phenyl | 2-chlorophenyl |
| phenyl | CH$_3$ | R | SO$_2$ | 1,4-phenyl | 2-fluorophenyl |
| phenyl | CH$_3$ | R | SO$_2$ | 1,4-phenyl | 2,6-dichlorophenyl |
| phenyl | CH$_3$ | R | SO$_2$ | 1,4-phenyl | 2,4-dichlorophenyl |
| phenyl | CH$_3$ | R | SO$_2$ | 1,4-phenyl | 2-trifluoromethylphenyl |
| phenyl | CH$_3$ | R | SO$_2$ | 1,4-phenyl | 2,4,6-trimethylphenyl |
| phenyl | CH$_3$ | S | SO$_2$ | 1,4-phenyl | 2-fluorophenyl |
| phenyl | CH$_3$ | S | SO$_2$ | 1,4-phenyl | 2,6-difluorophenyl |
| phenyl | CH$_3$ | S | SO$_2$ | 1,4-phenyl | 2,4-dichlorophenyl |
| phenyl | CH$_3$ | S | SO$_2$ | 1,4-phenyl | 2-trifluoromethylphenyl |
| phenyl | CH$_3$ | S | SO$_2$ | 1,4-phenyl | 2,4,6-trimethylphenyl |
| phenyl | CH$_3$ | Mix | SO$_2$ | 1,4-phenyl | 2-methylphenyl |
| phenyl | CH$_3$ | Mix | SO$_2$ | 1,4-phenyl | 2-chlorophenyl |
| phenyl | CH$_3$ | Mix | SO$_2$ | 1,4-phenyl | 3-fluorophenyl |
| 4-chlorophenyl | CH$_3$ | Mix | SO$_2$ | 1,4-phenyl | 2-methylphenyl |
| 4-chlorophenyl | CH$_3$ | Mix | SO$_2$ | 1,4-phenyl | 2-chlorophenyl |
| 4-chlorophenyl | CH$_3$ | Mix | SO$_2$ | 1,4-phenyl | 3-fluorophenyl |
| 4-chlorophenyl | cyclopropyl | — | SO$_2$ | 1,4-phenyl | 2-methylphenyl |
| 4-chlorophenyl | cyclopropyl | — | SO$_2$ | 1,4-phenyl | 2-chlorophenyl |
| 4-chlorophenyl | cyclopropyl | — | SO$_2$ | 1,4-phenyl | 3-fluorophenyl |
| phenyl | H | — | SO$_2$ | 1,4-phenyl | 2-methylphenyl |
| phenyl | H | — | SO$_2$ | 1,4-phenyl | 2-chlorophenyl |
| phenyl | H | — | SO$_2$ | 1,4-phenyl | 3-fluorophenyl |
| phenyl | CH$_3$ | R | SO$_2$ | 1,4-phenyl | phenyl |
| phenyl | CH$_3$ | R | SO$_2$ | 1,4-phenyl | 3-nitrophenyl |
| phenyl | CH$_3$ | R | SO$_2$ | 1,4-phenyl | 4-fluorophenyl |
| phenyl | CH$_3$ | R | SO$_2$ | 1,4-phenyl | 2-methylphenyl |
| phenyl | CH$_3$ | R | SO$_2$ | 1,4-phenyl | 3-trifluoromethylphenyl |
| phenyl | CH$_3$ | R | SO$_2$ | 1,4-phenyl | 4-trifluoromethylphenyl |

-continued

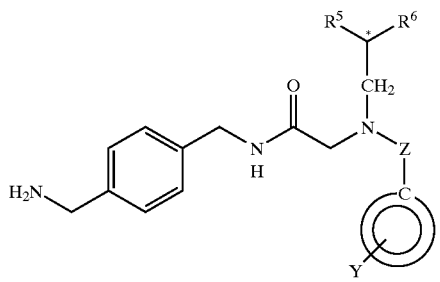

wherein $R^5$, $R^6$, Z,

Y and the stereospecificity are selected in concert from the group consisting of:

| $R^5$ | $R^6$ | Stereo | Z | C (ring) | Y |
|---|---|---|---|---|---|
| phenyl | CH₃ | R | SO₂ | 1,4-phenyl | 3-chlorophenyl |
| phenyl | CH₃ | R | SO₂ | 1,4-phenyl | 3-methoxy phenyl |
| phenyl | CH₃ | R | SO₂ | 1,4-phenyl | 2-trifluoromethyl phenyl |
| phenyl | CH₃ | R | SO₂ | 1,4-phenyl | 2-methoxy phenyl |
| phenyl | CH₃ | R | SO₂ | 1,4-phenyl | 4-trifluoro methoxyphenyl |
| phenyl | CH₃ | R | SO₂ | 1,4-phenyl | 3-fluorophenyl |
| phenyl | CH₃ | R | SO₂ | 1,4-phenyl | 2-naphthyl |
| phenyl | CH₃ | R | SO₂ | 1,4-phenyl | 3-chloro-4-fluorophenyl |
| phenyl | CH₃ | R | SO₂ | 1,4-phenyl | 3-bromophenyl |
| phenyl | CH₃ | R | SO₂ | 1,4-phenyl | 4-chlorophenyl |
| phenyl | CH₃ | R | SO₂ | 1,4-phenyl | 3,5-dichloro phenyl |
| phenyl | CH₃ | R | SO₂ | 1,4-phenyl | 2,4-dichloro phenyl |
| phenyl | CH₃ | R | SO₂ | 1,4-phenyl | 3,5-ditrifluoro methylphenyl |
| phenyl | CH₃ | R | SO₂ | 1,4-phenyl | 2-benzofuryl |
| phenyl | CH₃ | R | SO₂ | 1,4-phenyl | 2-(t-butylamino sulfonyl)phenyl |
| phenyl | CH₃ | R | SO₂ | 1,4-phenyl | 4-cyanophenyl |
| phenyl | CH₃ | R | SO₂ | 1,4-phenyl | 3-cyanophenyl |
| phenyl | CH₃ | R | SO₂ | 1,4-phenyl | 3-carboxyphenyl |
| phenyl | CH₃ | R | SO₂ | 1,4-phenyl | 2[(di-i-propyl) aminocarbonyl] phenyl |
| phenyl | CH₃ | R | SO₂ | 1,4-phenyl | 4-(3,5-dimethyl) isoxazolyl |
| phenyl | CH₃ | R | SO₂ | 1,4-phenyl | 2-methoxy-5-formylphenyl |
| phenyl | CH₃ | R | SO₂ | 1,4-phenyl | 4-pyridyl |
| phenyl | CH₃ | R | SO₂ | 1,4-phenyl | 2,3,4-tri methoxyphenyl |
| phenyl | CH₃ | R | SO₂ | 1,4-phenyl | phenoxathiinyl |
| phenyl | CH₃ | R | SO₂ | 1,4-phenyl | 2-(5-formyl)furyl |
| phenyl | CH₃ | R | SO₂ | 1,4-phenyl | 2-(4-methyl) thienyl |
| phenyl | CH₃ | R | SO₂ | 1,4-phenyl | dibenzothienyl |
| phenyl | CH₃ | R | SO₂ | 1,4-phenyl | dianthrenyl |
| phenyl | CH₃ | R | SO₂ | 1,4-phenyl | dibenzothienyl |
| phenyl | CH₃ | R | SO₂ | 1,4-phenyl | 3-benzothienyl |
| phenyl | CH₃ | R | SO₂ | 1,4-phenyl | 3,4-dimethoxy phenyl |
| phenyl | CH₃ | R | SO₂ | 1,4-phenyl | 2-fluorophenyl |
| phenyl | CH₃ | R | SO₂ | 1,4-phenyl | 1-naphthyl |
| phenyl | CH₃ | R | SO₂ | 1,4-phenyl | 4-methoxy phenyl |
| phenyl | CH₃ | R | SO₂ | 1,4-phenyl | 3-fluoro-4-chlorophenyl |
| phenyl | CH₃ | R | SO₂ | 1,4-phenyl | 2-nitrophenyl |
| phenyl | CH₃ | R | SO₂ | 1,4-phenyl | 3-biphenyl |
| phenyl | CH₃ | R | SO₂ | 1,4-phenyl | 2-(t-butylcarbonyl amino)-3-methoxy |

-continued

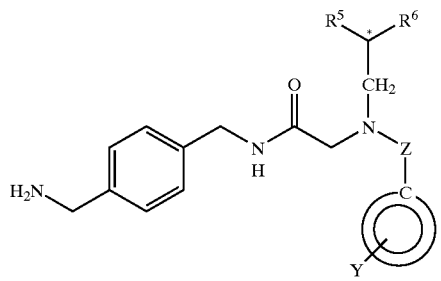

wherein $R^5$, $R^6$, Z,

Y and the stereospecificity are selected in concert from the group consisting of:

| $R^5$ | $R^6$ | Stereo | Z | | Y |
|---|---|---|---|---|---|
| phenyl | CH₃ | R | SO₂ | 1,4-phenyl | phenyl |
| phenyl | CH₃ | R | SO₂ | 1,4-phenyl | 2-(t-butyl carbonyl amino)-5-methoxy phenyl |
| phenyl | CH₃ | R | SO₂ | 1,4-phenyl | 2-(5-formyl)furyl |
| phenyl | CH₃ | R | SO₂ | 1,4-phenyl | 2,5-dimethoxy phenyl |
| phenyl | CH₃ | R | SO₂ | 1,4-phenyl | 2-(di(i-propyl) aminocarbonyl)-3-methoxyphenyl |
| phenyl | CH₃ | R | SO₂ | 1,4-phenyl | 4-methylthio phenyl |
| phenyl | CH₃ | R | SO₂ | 1,4-phenyl | 2,4,6-tri methylphenyl |
| phenyl | CH₃ | R | SO₂ | 1,4-phenyl | 3-methylphenyl |
| phenyl | CH₃ | R | SO₂ | 1,4-phenyl | 4-methylphenyl |
| phenyl | CH₃ | R | SO₂ | 1,4-phenyl | 3-pyridyl |
| phenyl | CH₃ | R | SO₂ | 1,4-phenyl | 3-aminophenyl |
| phenyl | CH₃ | R | SO₂ | 1,4-phenyl | 3-methylcarbonyl aminophenyl |
| phenyl | CH₃ | R | C(O) | 1,4-phenyl | 2-chlorophenyl |
| phenyl | CH₃ | R | C(O) | 1,4-phenyl | 2-methylphenyl |
| phenyl | CH₃ | R | C(O) | 1,4-phenyl | 3-fluorophenyl |
| phenyl | CH₃ | R | C(O) | 1,4-phenyl | 2-bromophenyl |
| phenyl | CH₃ | R | C(O) | 1,4-phenyl | 2,5-dichlorophenyl |
| phenyl | CH₃ | R | SO₂ | 1,4-phenyl | 2-methyl-3-chlorophenyl |
| phenyl | CH₃ | R | SO₂ | 1,4-phenyl | 2-chloro-5-methylphenyl |
| phenyl | CH₃ | R | SO₂ | 1,4-phenyl | 2-methyl-5-chlorophenyl |
| phenyl | CH₃ | R | SO₂ | 1,4-phenyl | 3-chloro-4-methylphenyl |
| phenyl | CH₃ | R | SO₂ | 1,4-phenyl | 2-chloro-6-methylphenyl |
| phenyl | CH₃ | R | SO₂ | 1,4-phenyl | 2-chloro-4-methylphenyl |
| 3-trifluoro methylphenyl | H | — | SO₂ | 1,4-phenyl | phenyl |
| phenyl | CH₃ | R | C(O)NH | 1,4-phenyl | phenyl |
| phenyl | CH₃ | S | C(O)NH | 1,4-phenyl | phenyl | and stereoisomers and pharmaceutically acceptable salts or esters thereof.

23. The compound of claim 1 of the formula

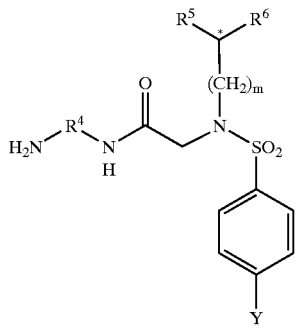

wherein R⁴, m, R⁵, R⁶, Y and the stereospecificity are selected in concert from the group consisting of:

| R⁴ | m | R⁵ | R⁶ | Stereo | Y |
|---|---|---|---|---|---|
| 1,5-n-pentyl | 1 | phenyl | CH₃ | R | 2-methylphenyl |
| 1,5-n-pentyl | 1 | phenyl | CH₃ | R | 2-chlorophenyl |
| 1,5-n-pentyl | 1 | phenyl | CH₃ | R | 3-fluorophenyl |
| 1,5-n-pentyl | 1 | phenyl | CH₃ | S | 2-methylphenyl |
| 1,5-n-pentyl | 1 | phenyl | CH₃ | S | 2-chlorophenyl |
| 1,5-n-pentyl | 1 | phenyl | CH₃ | S | 3-fluorophenyl |
| 1,5-n-pentyl | 1 | 2-methoxyphenyl | H | — | 2-methylphenyl |
| 1,6-n-hexyl | 1 | 2-methoxyphenyl | H | — | 2-chlorophenyl |
| 1,6-n-hexyl | 1 | 2-methoxyphenyl | H | — | 2-methoxyphenyl |
| 1,6-n-hexyl | 1 | 2-methoxyphenyl | H | — | 2,4-dichlorophenyl |
| 1,6-n-hexyl | 0 | 2-methoxyphenyl | H | — | 2-methylphenyl |
| 1,6-n-hexyl | 0 | 2-methoxyphenyl | H | — | 2-chlorophenyl |
| 1,6-n-hexyl | 0 | 2-methoxyphenyl | H | — | 2-methoxyphenyl |
| 1,6-n-hexyl | 0 | 2-methoxyphenyl | H | — | 2,4-dichlorophenyl |
| 1,6-n-hexyl | 1 | phenyl | CH₃ | R | 2-methylphenyl |
| 1,6-n-hexyl | 1 | phenyl | CH₃ | R | 2-chlorophenyl |
| 1,6-n-hexyl | 1 | phenyl | CH₃ | R | 3-fluorophenyl |
| 1,6-n-hexyl | 1 | phenyl | CH₃ | S | 2-methylphenyl |
| 1,6-n-hexyl | 1 | phenyl | CH₃ | S | 2-chlorophenyl |
| 1,6-n-hexyl | 1 | phenyl | CH₃ | S | 3-fluorophenyl | and stereoisomers and pharmaceutically acceptable salts or esters thereof.

24. The compound of claim 1 of the formula

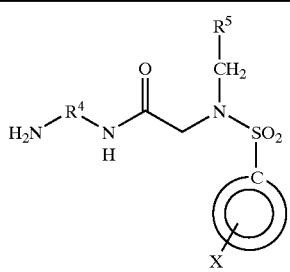

wherein R⁴, R⁵,

and X are selected in concert from the group consisting of:

| R⁴ | R⁵ | | X |
|---|---|---|---|
| 1,4-n-butyl | 2-methoxyphenyl | 1-phenyl | 2,3-dichloro |
| 1,6-n-hexyl | 2-methoxyphenyl | 1-phenyl | 2,3-dichloro | and stereoisomers and pharmaceutically acceptable salts or esters thereof.

25. The compound of claim 1 of the formula

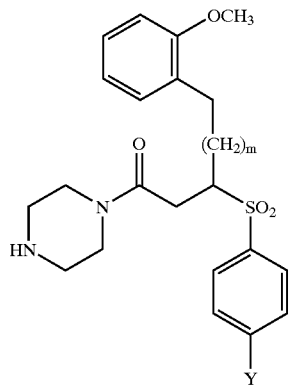

wherein m and Y are selected in concert from the group consisting of:

| m | Y |
|---|---|
| 1 | 2-methylphenyl |
| 1 | 3-thienyl |
| 1 | 2-methoxyphenyl |
| 1 | 4-fluorophenyl |
| 1 | 2,4-dimethoxyphenyl |
| 1 | 4-methoxyphenyl |
| 1 | 4-methylphenyl |
| 1 | 1-napthyl |
| 1 | 2-chlorophenyl |
| 1 | 3-pyridyl |
| 1 | 2-thienyl |
| 1 | 3-acetamidophenyl |
| 1 | phenyl |
| 1 | 4-chlorophenyl |
| 1 | 4-[3,5-dimethylisoxazolyl] |
| 1 | 3-chlorophenyl |
| 1 | 4-cyanophenyl |
| 1 | 4-pyridyl |
| 1 | 3-methoxyphenyl |
| 1 | 3-aminophenyl |
| 1 | 3-fluorophenyl |
| 1 | 2-fluorophenyl |
| 1 | 3,4-methylenedioxyphenyl |
| 0 | 2-methylphenyl |
| 0 | 3-thienyl |
| 0 | 2-methoxyphenyl |
| 0 | 4-fluorophenyl |
| 0 | 2,4-dimethoxyphenyl |
| 0 | 4-methoxyphenyl |
| 0 | 4-methylphenyl |
| 0 | 1-napthyl |
| 0 | 2-chlorophenyl |
| 0 | 3-pyridyl |
| 0 | 2-thienyl |
| 0 | 3-acetamidophenyl |
| 0 | phenyl |
| 0 | 4-chlorophenyl |
| 0 | 4-[3,5-dimethylisoxazolyl] |
| 0 | 3-chlorophenyl |
| 0 | 4-cyanophenyl |
| 0 | 4-pyridyl |
| 0 | 3-methoxyphenyl |
| 0 | 3-aminophenyl |
| 0 | 3-fluorophenyl |
| 0 | 2-fluorophenyl |
| 0 | 3,4-methylenedioxyphenyl | and stereoisomers and pharmaceutically acceptable salts or esters thereof.

26. The compound of claim 1 of the formula

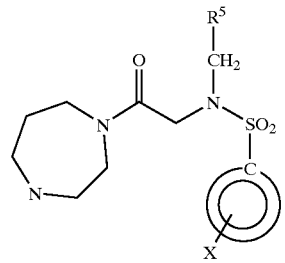

wherein R⁵,

and X are selected in concert from the group consisting of:

| R⁵ |  | X |
|---|---|---|
| 2-methoxyphenyl | 1-phenyl | 2,3-dichloro | and stereoisomers and pharmaceutically acceptable salts or esters thereof.

27. The compound of claim 1 of the formula

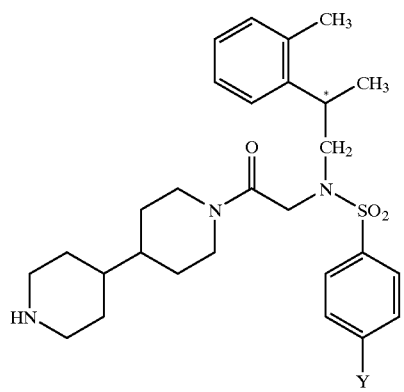

wherein Y and the stereospecificity are selected in concert from the group consisting of:

| Stereo | Y |
|---|---|
| R | 2-methylphenyl |
| R | 2-chlorophenyl |
| R | 3-fluorophenyl |
| S | 2-methylphenyl |
| S | 2-chlorophenyl |
| S | 3-fluorophenyl | and stereoisomers and pharmaceutically acceptable salts or esters thereof.

28. The compound of claim 1 of the formula

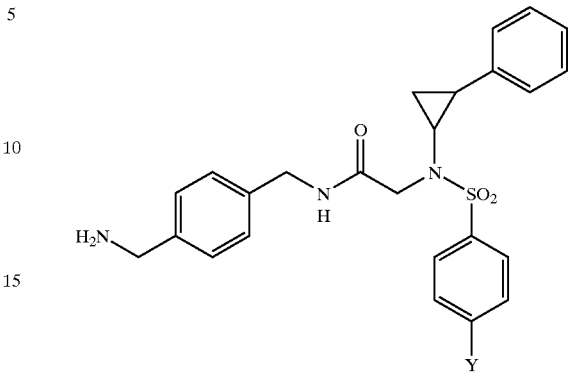

wherein Y is from the group consisting of:

| Y |
|---|
| 2-methylphenyl |
| 2-chlorophenyl |
| 3-fluorophenyl | and stereoisomers and pharmaceutically acceptable salts or esters thereof.

29. The compound of claim 1 of the formula

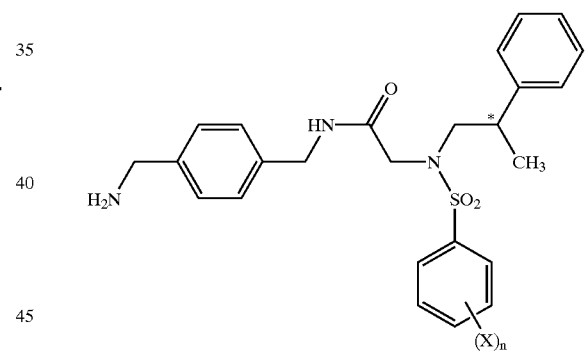

wherein X and n and the stereospecificity are selected in concert from the group consisting of:

| Stereo | n | X |
|---|---|---|
| R | 1 | 4-n-butyl |
| R | 0 | — |
| R | 1 | 4-bromo |
| S | 1 | 4-bromo |
| R | 1 | 4-methoxy |
| R | 1 | 4-trifluoromethyl |
| R | 1 | 4-isopropyl |
| R | 1 | 4-n-propyl |
| R | 1 | 4-t-butyl |
| R | 1 | 4-n-pentyl |
| R | 1 | 3-methoxy |
| S | 1 | 4-methoxy |
| S | 1 | 4-trifluoromethyl |
| S | 1 | 4-isopropyl |
| S | 1 | 4-n-propyl |
| S | 1 | 4-t-butyl |
| S | 1 | 4-n-pentyl |
| S | 1 | 3-methoxy | and stereoisomers and pharmaceutically acceptable salts or esters thereof.

30. The compound of claim 1 of the formula

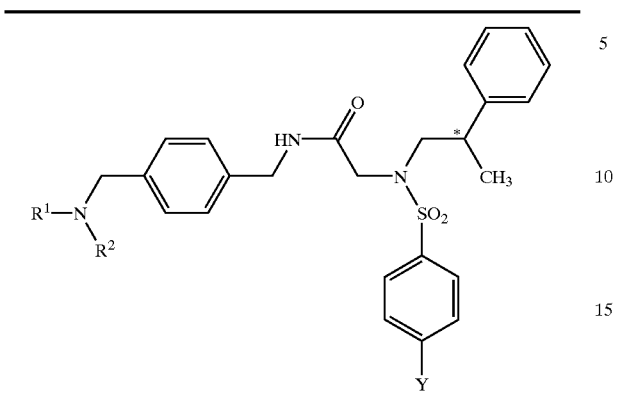

wherein $R^1$, $R^2$, Y and the stereospecificity are selected in concert from the group consisting of:

| $R^1$ | $R^2$ | Stereo | Y |
|---|---|---|---|
| methyl | methyl | R | 2-chlorophenyl |
| ethyl | ethyl | R | 2-chlorophenyl |
| H | methylcarbonyl | R | 2-chlorophenyl |
| methyl | methyl | S | 2-methylphenyl |
| ethyl | ethyl | S | 2-methylphenyl |
| H | methylcarbonyl | S | 2-methylphenyl | and stereoisomers and pharmaceutically acceptable salts or esters thereof.

31. The compound of claim 1 of the formula

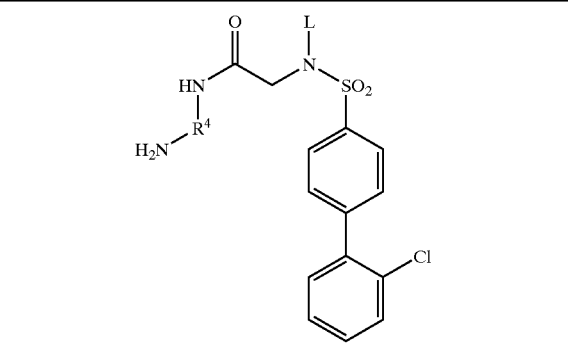

wherein $R^4$ and L are selected in concert from the group consisting of

| $R^4$ | L |
|---|---|
| —CH$_2$-(1,4-phenyl)-CH$_2$— | 4-methyloxyphenylethyl |
| —CH$_2$-(1,4-phenyl)-CH$_2$— | 3,6-dimethoxyphenylethyl |
| —CH$_2$-(1,4-phenyl)-CH$_2$— | 2,3-dimethoxyphenylethyl |
| —CH$_2$-(1,4-phenyl)-CH$_2$— | 1-cyclohexenylethyl |
| —CH$_2$-(1,4-phenyl)-CH$_2$— | 3-bromo-4,5-dimethylphenylethyl |
| —CH$_2$-(1,4-phenyl)-CH$_2$— | 2-chlorphenylethyl |
| —CH$_2$-(1,4-phenyl)-CH$_2$— | 3-chlorophenylethyl |
| —CH$_2$-(1,4-phenyl)-CH$_2$— | 2,4-dichlorophenylethyl |
| —CH$_2$-(1,4-phenyl)-CH$_2$— | 2,6-dichlorophenylethyl |
| —CH$_2$-(1,4-phenyl)-CH$_2$— | 2-trifluoromethylphenylethyl |
| —CH$_2$-(1,4-phenyl)-CH$_2$— | 3,4-dimethylphenylethyl |
| —CH$_2$-(1,4-phenyl)-CH$_2$— | 3,5-dimethylphenylethyl |
| —CH$_2$-(1,4-phenyl)-CH$_2$— | 3-methoxyphenylethyl |
| —CH$_2$-(1,4-phenyl)-CH$_2$— | 3-(2-chlorophenyl)-4,5-dimethoxyphenylethyl |
| n-hexyl | 3,4-dimethoxyphenylethyl |
| n-hexyl | 4-methoxyphenylethyl |
| n-hexyl | 2,3-dimethoxyphenylethyl |
| n-hexyl | 3-bromo-4,5-dimethoxyphenylethyl |
| n-hexyl | 2-chlorophenylethyl |
| n-hexyl | 3-chlorophenylethyl |
| n-hexyl | 2,4-dichlorophenylethyl |
| n-hexyl | 2,6-dichlorophenylethyl |
| n-hexyl | 3,5-dimethoxyphenylethyl |
| n-hexyl | 3-methoxyphenylethyl |
| n-hexyl | 2,5-dimethoxyphenylethyl |
| n-hexyl | 1-cyclohexenylethyl |
| n-hexyl | 3-(2-chlorophenyl)-3,4-dimethoxyphenylethyl |
| n-hexyl | 2-fluorophenylethyl |
| n-hexyl | 2-trifluoromethylphenylethyl |
| —CH$_2$-(1,4-phenyl)-CH$_2$— | 2-nitrophenylethyl |
| —CH$_2$-(1,4-phenyl)-CH$_2$— | 2-aminophenylethyl |
| —CH$_2$-(1,4-phenyl)-CH$_2$— | 2-dimethylaminophenylethyl |
| —CH$_2$-(1,4-phenyl)-CH$_2$— | 2-(methylcarbonylamino)phenylethyl |
| —CH$_2$-(1,4-phenyl)-CH$_2$— | 2-(methytsulfonylamino)phenylethyl |
| —CH$_2$-(1,4-phenyl)-CH$_2$— | CH$_2$—(CH$_3$)2-phenyl |
| —CH$_2$-(1,4-phenyl)-CH$_2$— | CH$_2$—C(OCH$_3$)-phenyl |
| —CH$_2$-(1,4-phenyl)-CH$_2$— | CH$_2$—CH(CH$_3$)-(2-methoxyphenyl) |
| —CH$_2$-(1,4-phenyl)-CH$_2$— | bicyclo[4.2.0]octa-1,3,5-triene |
| —CH$_2$-(1,4-phenyl)-CH$_2$— | CH$_2$—CH(cyclohexyl)-phenyl |
| —CH$_2$-(1,4-phenyt)-CH$_2$— | CH$_2$—CH(cyclobutyl)-phenyl |
| —CH$_2$-(1,4-phenyl)-CH$_2$— | CH$_2$—CH(ethyl)-phenyl |
| —CH$_2$-(1,4-phenyl)-CH$_2$— | 2,3-dihydro-1H-indene |
| —CH$_2$-(1,4-phenyl)-CH$_2$— | CH(phenyl)$_2$ |
| —CH$_2$-(1,4-phenyl)-CH$_2$— | 2-methylphenylethyl |
| —CH$_2$-(1,4-phenyl)-CH$_2$— | 3-fluorophenylethyl |
| —CH$_2$-(1,4-phenyl)-CH$_2$— | 3,4-methylenedioxy phenyl |
| —CH$_2$-(1,4-phenyl)-CH$_2$— | 2-pyridylethyl |
| —CH$_2$-(1,4-phenyl)-CH$_2$— | 2-thienylethyl |
| —CH$_2$-(1,4-phenyl)-CH$_2$— | 2-(N-methyl)-pyrrotidinylethyl |
| —CH$_2$-(1,4-phenyl)-CH$_2$— | phenylpropyl |
| —CH$_2$-(1,4-phenyl)-CH$_2$— | 2-ethoxyphenylethyl |
| —CH$_2$-(1,4-phenyl)-CH$_2$— | 3,4-dichlorophenylethyl |
| n-hexyl | CH$_2$—CH(OCH$_3$)-phenyl |
| n-hexyl | CH$_2$—CH(CH$_3$)-(2-methoxyphenyl) |
| n-hexyl | bicyclo[4.2.0]octa-1,3,5-triene |
| n-hexyl | CH$_2$—CH(cyclohexyl)-phenyl |
| n-hexyl | CH$_2$—CH(cyclobutyl)-phenyl |
| n-hexyl | CH$_2$—CH(ethyl)-phenyl |
| n-hexyl | 2,3-dihydro-1H-indene |
| n-hexyl | CH$_2$—CH(phenyl)$_2$ |
| n-hexyl | 2-methylphenylethyl |
| n-hexyl | 3-fluorophenylethyl |
| n-hexyl | 3,4-methylenedioxyphenyl |
| n-hexyl | 2-pyridylethyl |
| n-hexyl | 2-thienylethyl |
| n-hexyl | 2-(N-methytpyrrolidinyl)ethyl |
| n-hexyl | phenylpropyl |
| n-hexyl | 2-ethoxyphenylethyl |
| n-hexyl | 3,4-dichlorophenylethyl |
| n-hexyl | 3-trifluoromethylphenylethyl | and stereoisomers and pharmaceutically acceptable salts or esters thereof.

32. The compound of claim 1 of the formula
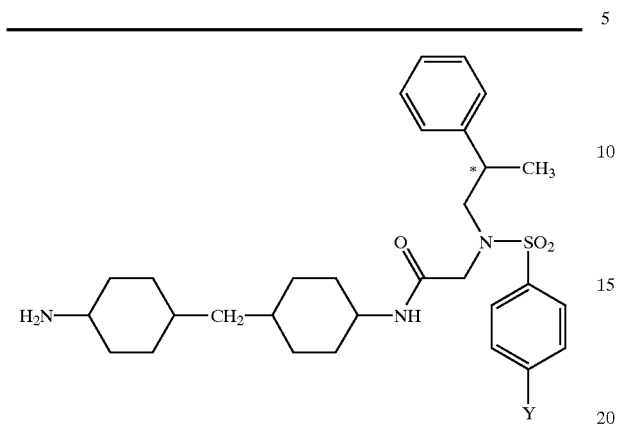
wherein Y and the stereospecificity are selected in concert from the group consisting of:
| Stereo | Y |
|---|---|
| R | 2-chlorophenyl |
| R | 2-methylphenyl |
| R | 3-fluorophenyl |
| S | 2-chlorophenyl |
and stereoisomers and pharmaceutically acceptable salts or esters thereof.
33. The compound of claim 1, selected from the group consisting of
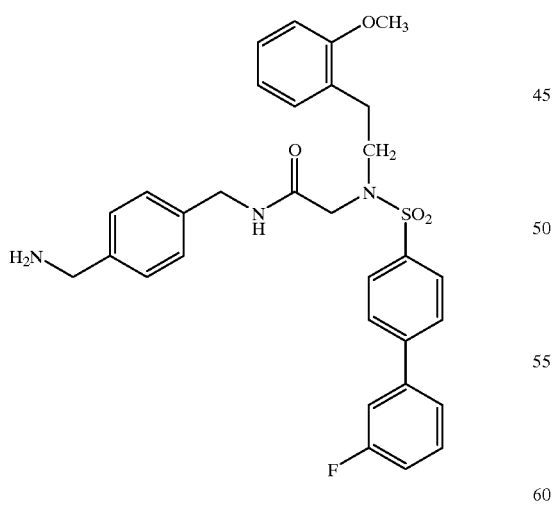
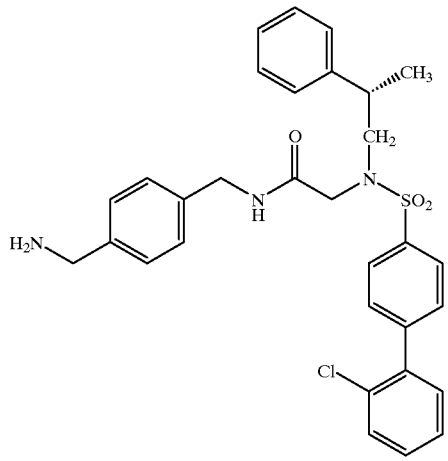
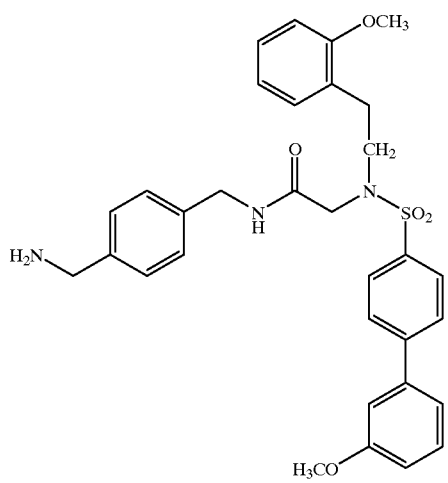
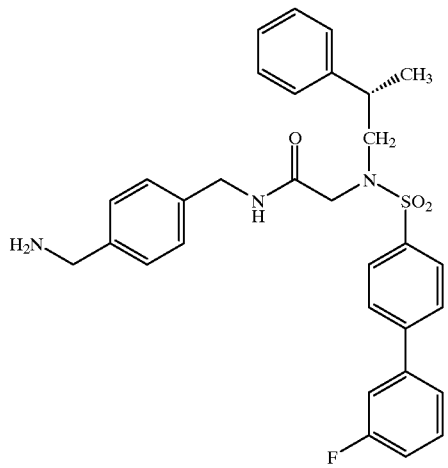

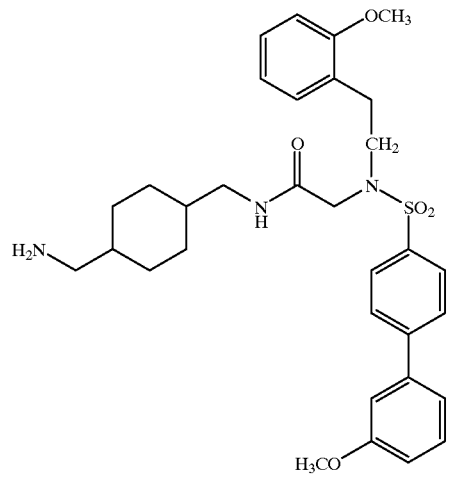
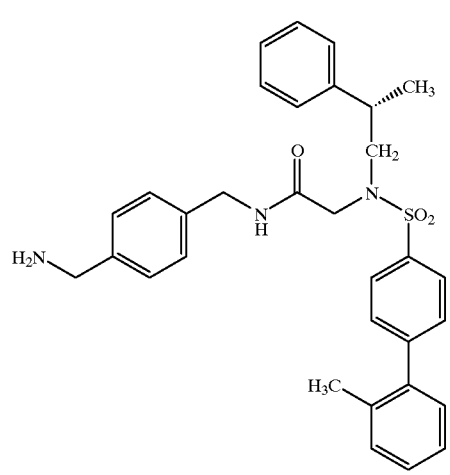
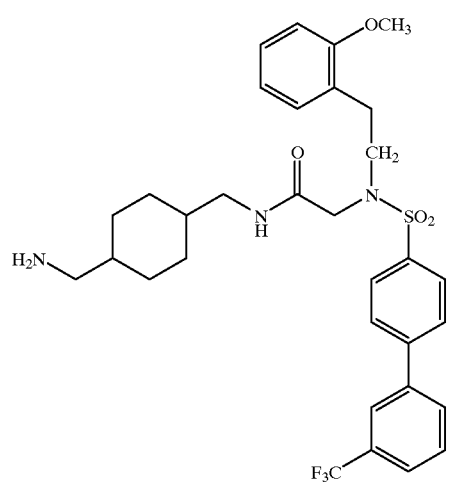
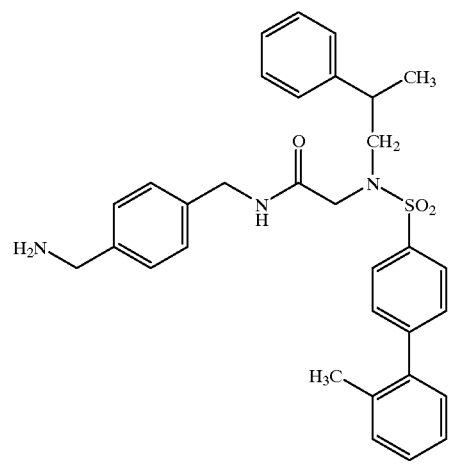
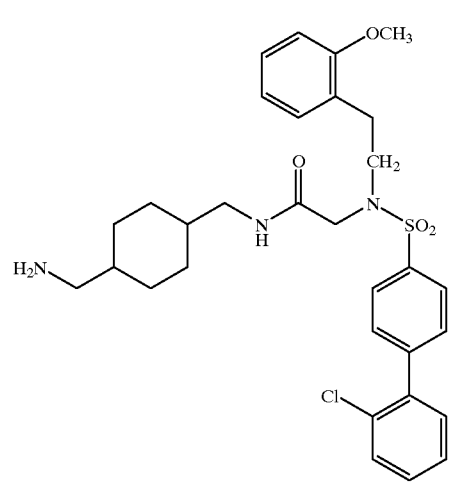
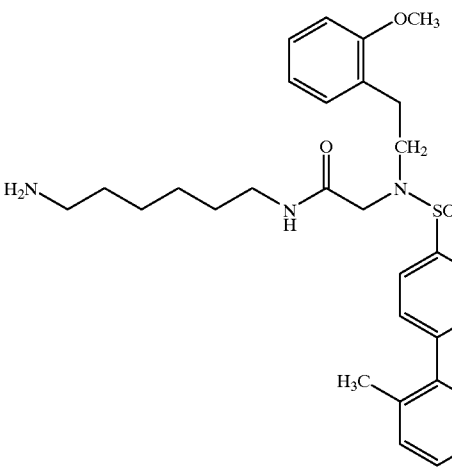

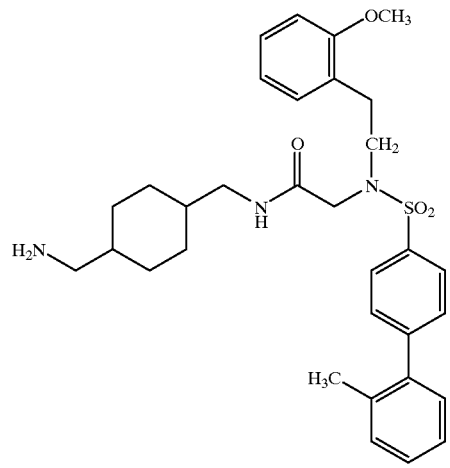
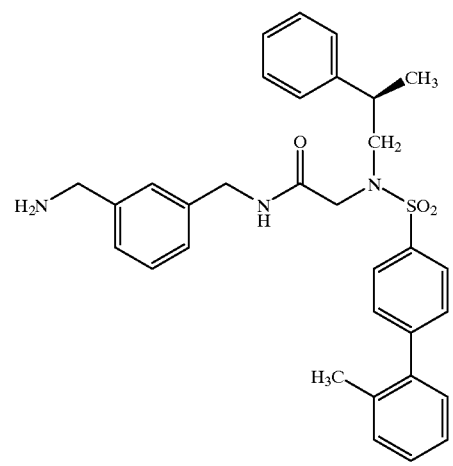
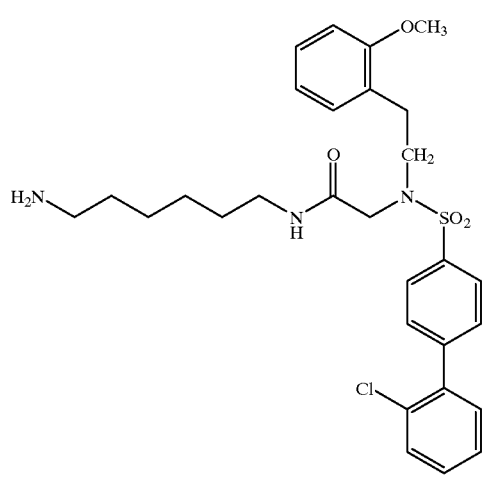
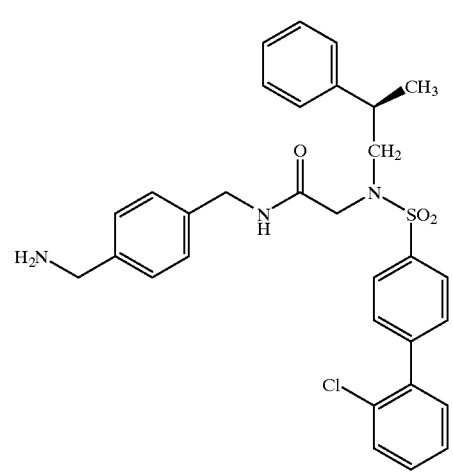
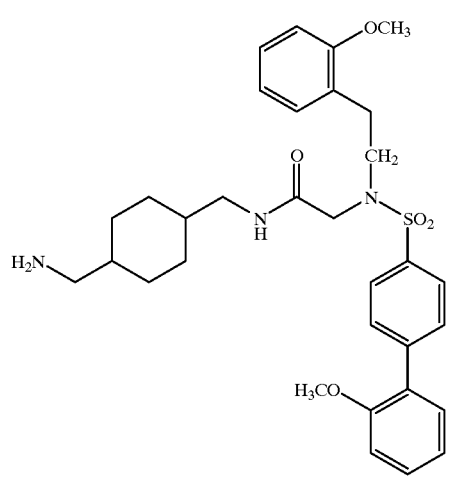
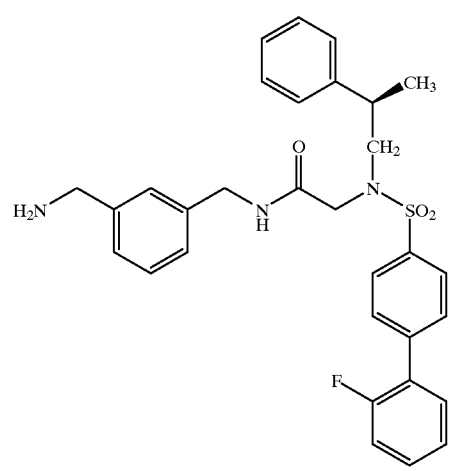

-continued

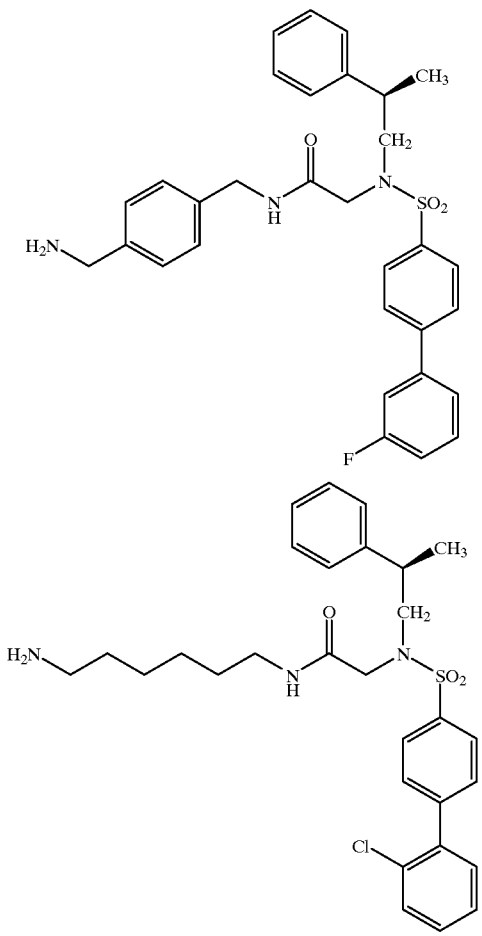

and stereoisomers and pharmaceutically acceptable salts or esters thereof.

34. A pharmaceutical composition comprising a pharmaceutically acceptable carrier and a compound of claim 1.

35. A process for making a pharmaceutical composition comprising mixing a compound of claim 1 and a pharmaceutically acceptable carrier.

36. A method of treating a condition or disorder mediated by the FSH receptor, in a subject in need thereof comprising administering to the subject a therapeutically effective amount of the compound of claim 1.

37. A method of treating a condition or disorder selected from the group consisting of uterine fibroids, endometriosis, polycystic ovarian disease, dysfunctional uterine bleeding, breast cancer and ovarian cancer; depletion of oocytes; spermatocyte depletion; or for female and male contraception, in a subject in need thereof, comprising administering to the subject a therapeutically effective amount of the compound of claim 1.

38. A pharmaceutical composition comprising a pharmaceutically acceptable carrier and a compound of claim 1, for the preparation of a medicament for the treatment of a condition or disorder selected from the group consisting of uterine fibroids, endometriosis, polycystic ovarian disease, dysfunctional uterine bleeding, breast cancer and ovarian cancer; depletion of oocytes; spermatocyte depletion; or for female and male contraception.

* * * * *